(12) United States Patent
Allec et al.

(10) Patent No.: US 10,687,718 B2
(45) Date of Patent: Jun. 23, 2020

(54) SYSTEMS AND METHODS FOR NON-PULSATILE BLOOD VOLUME MEASUREMENTS

(71) Applicant: Apple Inc., Cupertino, CA (US)

(72) Inventors: Nicholas Paul Joseph Allec, Menlo Park, CA (US); Rui Peterson, San Jose, CA (US); Ueyn L. Block, Menlo Park, CA (US); Vivek Venugopal, San Jose, CA (US)

(73) Assignee: Apple Inc., Cupertino, CA (US)

( * ) Notice: Subject to any disclaimer, the term of this patent is extended or adjusted under 35 U.S.C. 154(b) by 300 days.

(21) Appl. No.: 15/592,016

(22) Filed: May 10, 2017

(65) Prior Publication Data

US 2017/0325698 A1 Nov. 16, 2017

Related U.S. Application Data

(60) Provisional application No. 62/334,363, filed on May 10, 2016.

(51) Int. Cl.
  *A61B 5/026* (2006.01)
  *A61B 5/00* (2006.01)
  (Continued)

(52) U.S. Cl.
  CPC .......... *A61B 5/0261* (2013.01); *A61B 5/0205* (2013.01); *A61B 5/0295* (2013.01);
  (Continued)

(58) Field of Classification Search
  CPC ... A61B 5/026; A61B 5/14552; A61B 5/7264; A61B 5/721; A61B 5/6898;
  (Continued)

(56) References Cited

U.S. PATENT DOCUMENTS

| 4,227,091 A | 10/1980 | Sick |
| 4,880,304 A | 11/1989 | Jaeb |

(Continued)

FOREIGN PATENT DOCUMENTS

| EP | 2 992 821 A1 | 3/2016 |
| JP | 2000-163031 A | 6/2000 |

(Continued)

OTHER PUBLICATIONS

Non-Final Office Action dated Jun. 13, 2019, for U.S. Appl. No. 15/592,020, filed May 10, 2017, 8 pages.

(Continued)

*Primary Examiner* — Oommen Jacob
(74) *Attorney, Agent, or Firm* — Brownstein Hyatt Farber Schreck, LLP

(57) ABSTRACT

This relates to systems and methods for determining one or more of a user's physiological signals. The one or more of the user's physiological signals can be determined by measuring pulsatile blood volume changes. Motion artifacts included in the signals can be canceled or reduced by measuring non-pulsatile blood volume changes and adjusting the signal to account for the non-pulsatile blood information. Non-pulsatile blood volume changes can be measured using at least one set of light emitter-light sensor. The light emitter can be located in close proximity (e.g., less than or equal to 1 mm away) to the light sensor, thereby limiting light emitted by the light emitter to blood volume without interacting with one or more blood vessels and/or arterioles. In some examples, the systems can further include an accelerometer configured to measure the user's acceleration, and the acceleration signal can be additionally be used for compensating for motion artifacts.

12 Claims, 42 Drawing Sheets

(51) Int. Cl.
*A61B 5/024* (2006.01)
*A61B 5/1455* (2006.01)
*A61B 5/0205* (2006.01)
*A61B 5/0295* (2006.01)
*A61B 5/11* (2006.01)

(52) U.S. Cl.
CPC ...... *A61B 5/02427* (2013.01); *A61B 5/02438* (2013.01); *A61B 5/11* (2013.01); *A61B 5/14552* (2013.01); *A61B 5/681* (2013.01); *A61B 5/6843* (2013.01); *A61B 5/6898* (2013.01); *A61B 5/721* (2013.01); *A61B 5/7214* (2013.01); *A61B 5/7264* (2013.01); *A61B 5/02433* (2013.01); *A61B 2562/0219* (2013.01); *A61B 2562/0238* (2013.01); *A61B 2562/046* (2013.01); *A61B 2562/146* (2013.01); *A61B 2562/185* (2013.01)

(58) Field of Classification Search
CPC ......... A61B 5/6843; A61B 5/681; A61B 5/11; A61B 5/0295; A61B 5/0261; A61B 5/7214; A61B 5/02427; A61B 5/02438; A61B 2562/046; A61B 2562/0238; A61B 2562/0219; A61B 5/02433; A61B 2562/146; A61B 2562/185
USPC .......................................... 600/473, 476–480
See application file for complete search history.

(56) References Cited

U.S. PATENT DOCUMENTS

| | | | |
|---|---|---|---|
| 5,483,261 A | 1/1996 | Yasutake | |
| 5,488,204 A | 1/1996 | Mead et al. | |
| 5,695,520 A | 12/1997 | Bruckner et al. | |
| 5,825,352 A | 10/1998 | Bisset et al. | |
| 5,835,079 A | 11/1998 | Shieh | |
| 5,880,411 A | 3/1999 | Gillespie et al. | |
| 6,188,391 B1 | 2/2001 | Seely et al. | |
| 6,263,222 B1* | 7/2001 | Diab | A61B 5/14551 600/310 |
| 6,310,610 B1 | 10/2001 | Beaton et al. | |
| 6,323,846 B1 | 11/2001 | Westerman et al. | |
| 6,341,116 B1* | 1/2002 | Lee | G11B 7/123 369/110.01 |
| 6,475,153 B1 | 11/2002 | Khair et al. | |
| 6,558,335 B1 | 5/2003 | Thede | |
| 6,605,045 B2 | 8/2003 | Ohsaki et al. | |
| 6,690,387 B2 | 2/2004 | Zimmerman et al. | |
| 7,015,894 B2 | 3/2006 | Morohoshi | |
| 7,184,064 B2 | 2/2007 | Zimmerman et al. | |
| 7,616,110 B2 | 11/2009 | Crump et al. | |
| 7,663,607 B2 | 2/2010 | Hotelling et al. | |
| 7,738,935 B1 | 6/2010 | Turcott | |
| 8,279,441 B2 | 10/2012 | Brown | |
| 8,378,811 B2 | 2/2013 | Crump et al. | |
| 8,442,608 B2* | 5/2013 | Pav | A61B 5/1455 600/310 |
| 8,479,122 B2 | 7/2013 | Hotelling et al. | |
| 8,618,930 B2 | 12/2013 | Papadopoulos et al. | |
| 8,649,839 B2* | 2/2014 | Chin | A61B 5/14552 600/324 |
| 9,339,235 B2* | 5/2016 | Rodriguez-Llorente | A61B 5/7203 |
| 9,804,027 B2 | 10/2017 | Fish | |
| 9,883,824 B2 † | 2/2018 | Tiao | |
| 10,098,555 B2* | 10/2018 | Yamaji | A61B 5/6826 |
| 2002/0097400 A1 | 7/2002 | Jung | |
| 2002/0169381 A1* | 11/2002 | Asada | A61B 5/14552 600/485 |
| 2004/0255318 A1* | 12/2004 | Braitberg | G11B 7/08576 720/736 |
| 2006/0197753 A1 | 9/2006 | Hotelling | |
| 2008/0013887 A1 | 1/2008 | Sappey | |
| 2008/0208020 A1 | 8/2008 | Cinbis et al. | |
| 2010/0010326 A1* | 1/2010 | Dalvi | A61B 5/14532 600/322 |
| 2010/0249557 A1* | 9/2010 | Besko | A61B 5/14553 600/340 |
| 2010/0317943 A1 | 12/2010 | Kuhn et al. | |
| 2013/0292571 A1 | 11/2013 | Mukherjee | |
| 2014/0049155 A1 | 2/2014 | Kurtin | |
| 2014/0107493 A1* | 4/2014 | Yuen | A61B 5/0205 600/473 |
| 2014/0155705 A1 | 6/2014 | Papadopoulos et al. | |
| 2014/0361147 A1 | 12/2014 | Fei | |
| 2015/0190063 A1 | 7/2015 | Zakharov et al. | |
| 2015/0335232 A1 | 11/2015 | Ito | |
| 2016/0058312 A1 | 3/2016 | Han et al. | |
| 2016/0183813 A1 | 6/2016 | Naima | |
| 2016/0184019 A1 | 6/2016 | Griffin | |
| 2016/0252458 A1 | 9/2016 | Yu | |
| 2016/0296173 A1 | 10/2016 | Culbert | |
| 2017/0005241 A1 | 1/2017 | Lotito | |
| 2017/0045450 A1 | 2/2017 | Lieber | |
| 2017/0249445 A1* | 8/2017 | Devries | G16H 10/60 |
| 2017/0311825 A1* | 11/2017 | Weekly | A61B 5/02433 |
| 2017/0325698 A1* | 11/2017 | Allec | A61B 5/0205 |
| 2017/0325744 A1 | 11/2017 | Allec et al. | |
| 2018/0138359 A1 | 5/2018 | Ulmer | |
| 2018/0242892 A1* | 8/2018 | Schie | A61B 5/14552 |

FOREIGN PATENT DOCUMENTS

| | | |
|---|---|---|
| JP | 2002-342033 A | 11/2002 |
| WO | WO 17/198033 | 11/2017 |

OTHER PUBLICATIONS

International Search Report dated Aug. 9, 2017, for PCT Application No. PCT/US2017/032028, filed May 10, 2017, four pages.

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

\* cited by examiner
† cited by third party

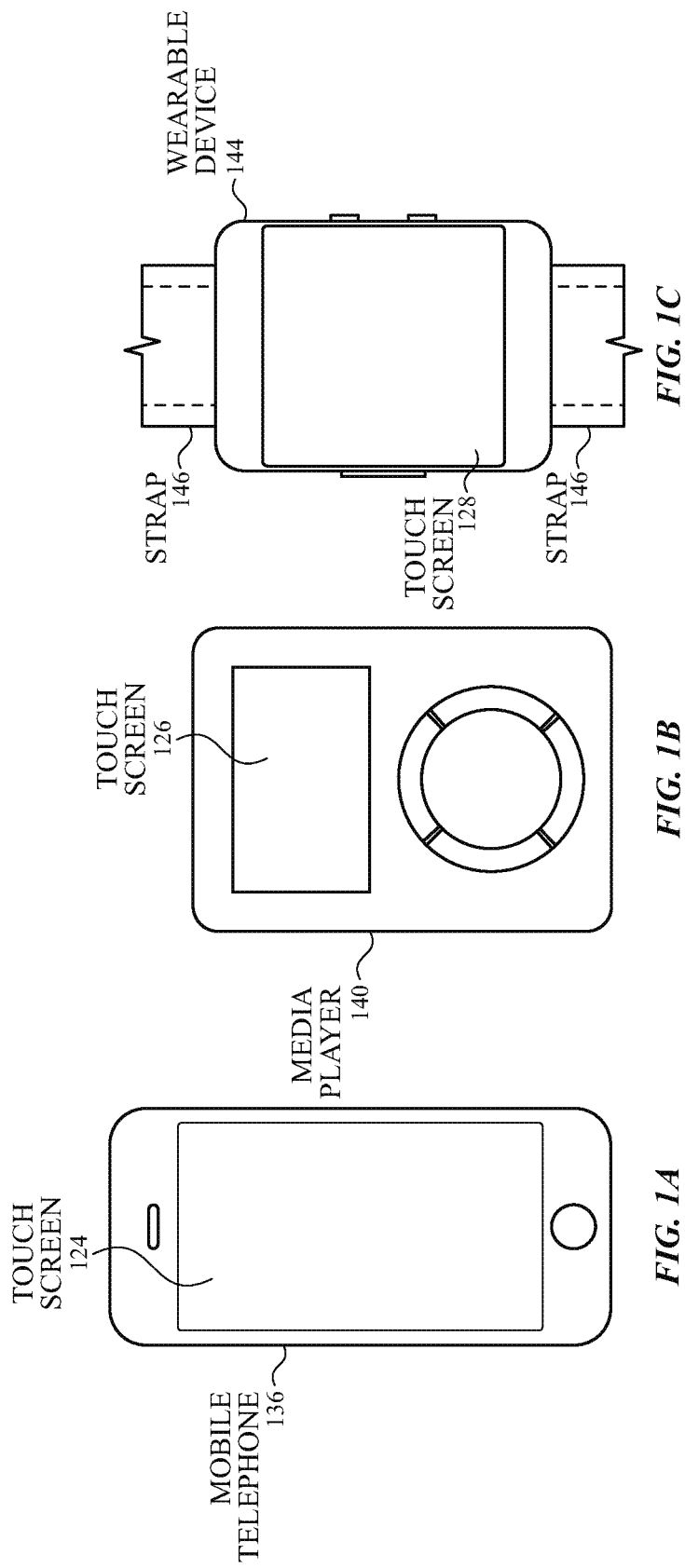

SYSTEMS AND METHODS FOR NON-PULSATILE BLOOD VOLUME MEASUREMENTS

CROSS-REFERENCE TO RELATED APPLICATIONS

This application claims priority to U.S. Provisional Patent Application Ser. No. 62/334,363, filed May 10, 2016, which is hereby incorporated by reference in its entirety.

FIELD

This relates generally to architectures for PPG systems, and, more particularly, to PPG systems capable of generating signals including little-to-no pulsatile blood information and capable of measuring non-pulsatile blood volume changes.

BACKGROUND

A user's physiological signals (e.g., pulse rate or arterial oxygen saturation) can be determined by photoplethysmogram (PPG) systems. In a basic form, PPG systems can employ one or more light sources that illuminate a user's tissue and one or more light detectors to receive light that enters and probes a subsurface volume of tissue. The light sources and light detectors can be in contact with the tissue or can be remote (i.e., not in contact) to the tissue surface. The received light can include light with an amplitude that can be modulated in time as a result of interaction with pulsatile blood flow and parasitic, non-signal light that can indirectly sample pulsatile tissue volumes with an amplitude that can be modulated (i.e., "noise" or "artifacts") and/or unmodulated (i.e., DC).

Although PPG systems measure the pulsatile blood flow to determine a user's physiological signals, these measurements may be corrupted by noise introduced by, for example, the user's motion, motions from within the user's body (e.g., tendon motion and/or muscle motions that can affect venous blood volume information), tilt and/or pull of the device, ambient light variations, or any combination thereof. While some PPG systems can utilize accelerometer measurements to correct for such noise, accelerometer measurements can be limited to the gross, periodic motion. Given that a user's motion may not be limited to gross, periodic motion, a PPG system capable of differentiating pulsatile blood volume changes from anatomical motion can be desired. In some examples, anatomical motion can be measured by measuring non-pulsatile blood volume changes.

SUMMARY

This relates to systems and methods for determining one or more of a user's physiological signals. The one or more of the user's physiological signals can be determined by measuring pulsatile blood volume changes. Motion artifacts included in the signals can be canceled or reduced by measuring non-pulsatile blood volume changes and adjusting the signal to account for the non-pulsatile blood information. Non-pulsatile blood volume changes can be measured using at least one set of light emitter-light sensor. The light emitter can be located in close proximity (e.g., less than or equal to 1 mm away) to the light sensor and/or emitting light at specific wavelengths (e.g., greater than 600 nm), thereby limiting light emitted by the light emitter to interaction to venous blood (non-pulsatile blood) volume changes. In some examples, the systems can further include an accelerometer configured to measure the user's acceleration, and the acceleration signal can be additionally be used for compensating of motion artifacts.

BRIEF DESCRIPTION OF THE DRAWINGS

FIGS. 1A-1C illustrate systems in which examples of the disclosure can be implemented

DETAILED DESCRIPTION

Figure 2A:
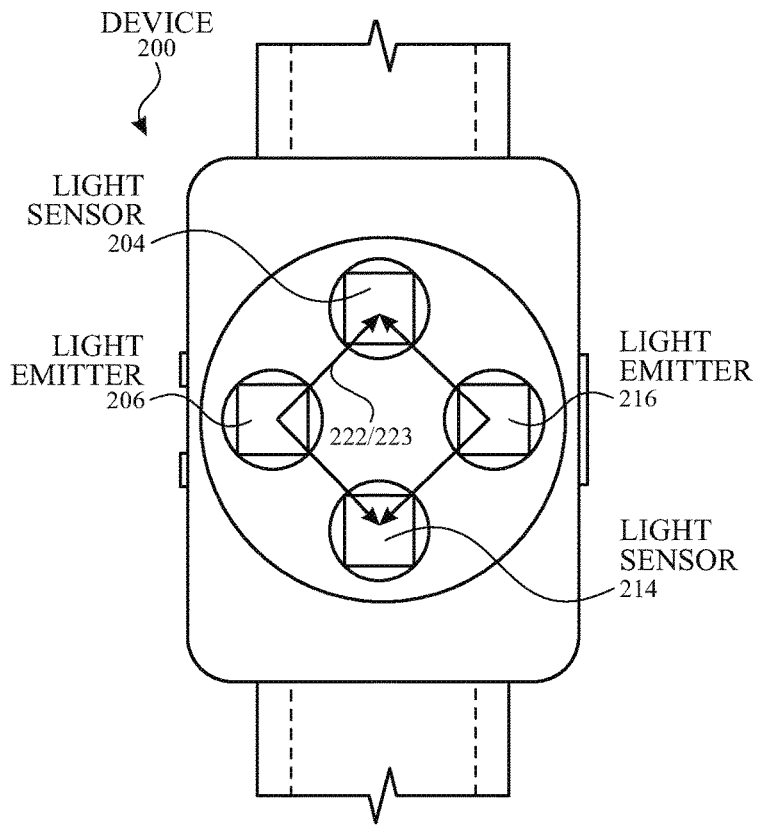
FIG. 2A illustrates a top view of an exemplary electronic device including light sensors and light emitters for measuring a user's physiological signal according to examples of the disclosure.

In the following description of examples, reference is made to the accompanying drawings in which it is shown by way of illustration specific examples that can be practiced. It is to be understood that other examples can be used and structural changes can be made without departing from the scope of the various examples.

This relates to systems and methods for determining one or more of a user's physiological signals. The one or more of the user's physiological signals can be determined by measuring pulsatile blood volume changes. Motion artifacts included in the signals can be canceled or reduced by measuring non-pulsatile blood volume changes and adjusting the signal to account for the non-pulsatile blood information. Deeper tissue of a user can be more susceptible to motion artifacts due to, for example, muscle movement, tendon movement, non-pulsatile blood movement, or a combination thereof. The effect of the motion artifacts can be less pronounced in the superficial layers of the user due to absence of the muscles and tendons. In some examples, non-pulsatile blood volume changes can be measured using at least one set of light emitter-light sensor. The light emitter can be located in close proximity (e.g., less than or equal to 1 mm away) to the light sensor to limit the depth within the tissue that is measured. Light can be emitted at one or more wavelengths (e.g., greater than 600 nm) less sensitive to oxy-hemoglobin, which can reduce the interaction of light to venous blood volume changes. In some examples, the systems can further include an accelerometer configured to measure the user's acceleration, and the acceleration signal can be additionally be used for compensating of motion artifacts.

Representative applications of methods and apparatus according to examples of the present disclosure are described in this section. These examples are being provided solely to add context and aid in the understanding of the described examples. It will thus be apparent to one skilled in the art that the described examples may be practiced without some or all of the specific details. In other instances, well-known process steps have been described in detail in order to avoid unnecessarily obscuring the described examples. Other applications are possible, such that the following examples should not be taken as limiting.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The systems of FIGS. 1A-1C can utilize the reconfigurable apertures and methods for detecting a PPG signal as will be disclosed.

Figure 2B:
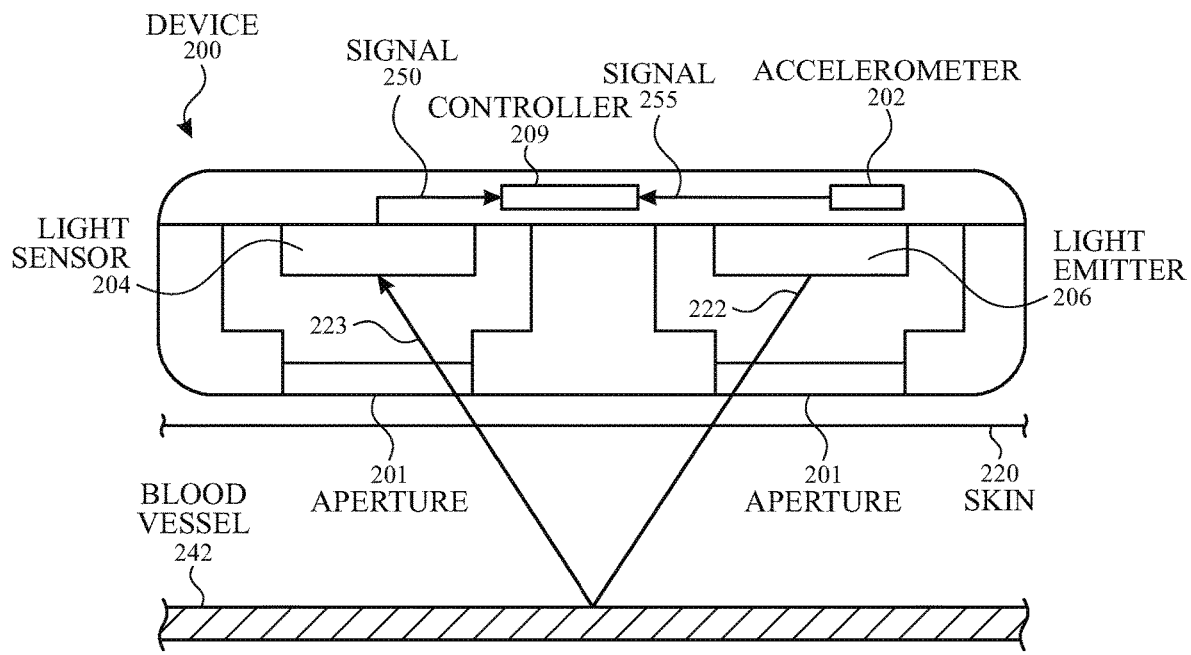
FIG. 2B illustrates a cross-sectional view of an exemplary electronic device including light sensors and light emitters for measuring a user's physiological signal according to examples of the disclosure.

FIG. 2A illustrates a top view and FIG. 2B illustrates a cross-sectional view of an exemplary electronic device including light sensors and light emitters for measuring a user's physiological signal according to examples of the disclosure. The top view in FIG. 2A can be viewed as the underside of wearable device 144 of FIG. 1C, for example. Device 200 can include light sensor 204, light sensor 214, light emitter 206, and light emitter 216. Light sensor 204 can be optically coupled to light emitter 206. Light sensor 214 can be optically coupled to light emitter 216. Device 200 can be situated such that light sensor 204, light sensor 214, light emitter 206, and light emitter 208 are proximate to a skin 220 of a user. For example, device 200 can be held in a user's hand or strapped to a user's wrist, among other possibilities.

Light emitter 206 can be configured to emit light (e.g., light 222). A portion of the one or more light paths can be absorbed by one or more blood vessels 242, and a portion of the one or more light paths can reflect back to be detected by a light sensor. For example, as illustrated in FIG. 2B, a portion of light 222 (emitted from light emitter 206) can be absorbed by blood vessel 242, and a portion of light (e.g., light 223) can reflect back for detection by light sensor 204. Light emitter 206 can also be configured to emit light, and a portion of the light can reflect back for detection by light sensor 214. Similarly, light emitter 216 can be configured to emit light towards light sensor 204 and light sensor 214.

Signal 250 can include the measured total signal (i.e., sum of the measured modulated light and unmodulated light) detected by the light sensor (e.g., light sensor 204). In some examples, the device or system can include an accelerometer 202. Accelerometer 202 can be any type of sensor capable of measuring acceleration. Signal 255 can include the measured acceleration signal detected by accelerometer 202. Device 200 can include a processor or controller 209 configured to determine the user's physiological signal from signal 250 and signal 255. The user's physiological signal can be determined using any number of algorithms or simple mathematical functions including, but not limited to, subtracting, multiplying, and/or scaling.

In some examples, the capabilities of the accelerometer included in the PPG system may be limited to measuring gross motion (e.g., the user waving his or her hand) and may not be capable of measuring anatomical motion (e.g., the user clenching his or her fist). In some examples, the capabilities of the accelerometer can be limited to periodic motion artifacts. As a result, signal 250 can include distortion from the anatomical motion, and the system may erroneously include the distortions in its determination of the user's physiological signal (due to the inability to distinguish anatomical motion). Examples of anatomical motion can include surface motion or motion induced by blood re-distribution (e.g., increases or decreases in venous blood caused by user motion). In some examples, the system can be capable of measuring solely non-pulsatile blood volume changes—where a system relying entirely on an accelerometer for noise correction may not be capable of measuring non-pulsatile blood volume changes. In some examples, the system can be capable of measuring non-periodic motion artifacts. By measuring the modulation of the optical signal from non-pulsatile blood volume changes, motion artifacts can be accurately determined.

Figure 3A:
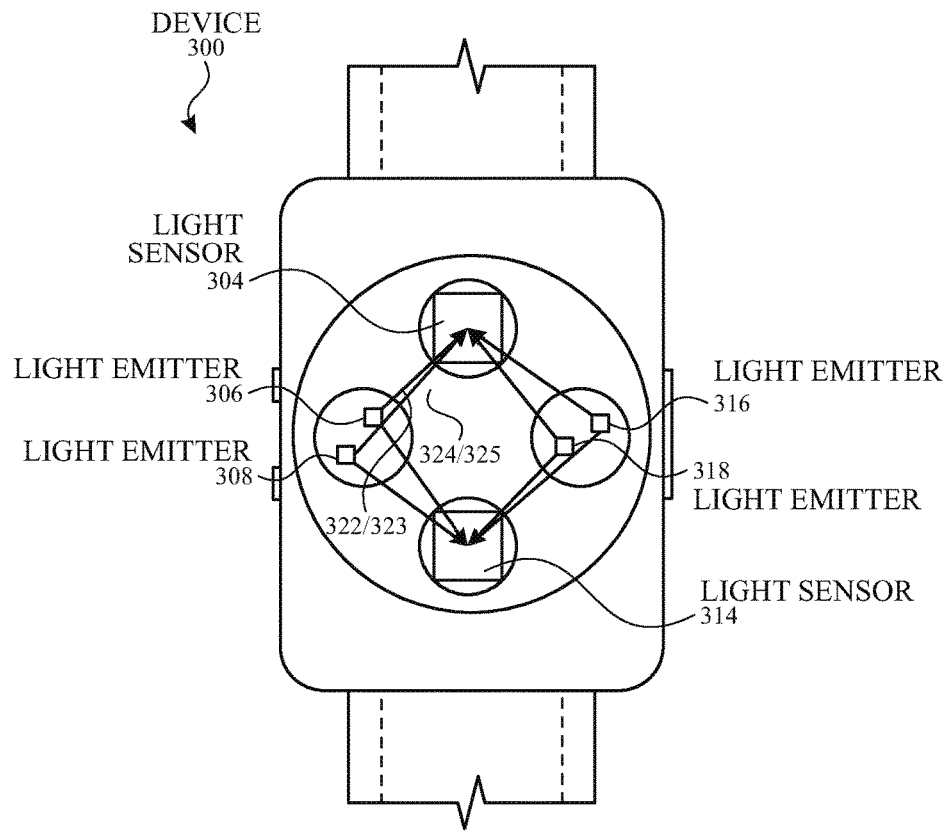
FIG. 3A illustrates a top view of an exemplary electronic device including light sensors and light emitters for measuring a user's physiological signal according to examples of the disclosure.
Figure 3B:
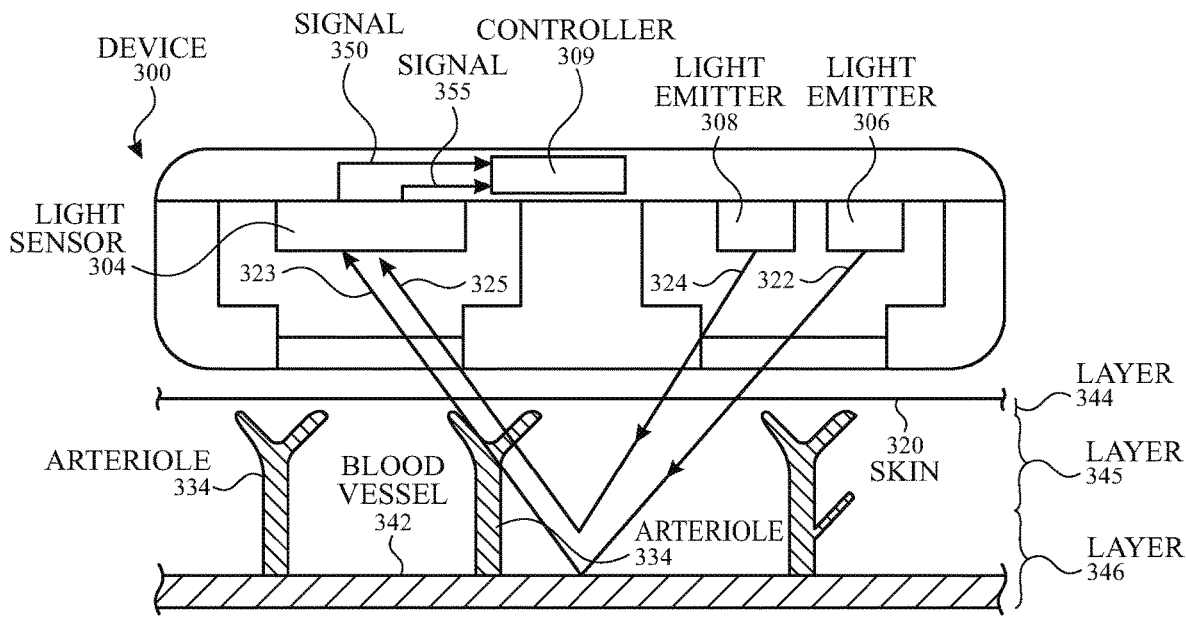
FIG. 3B illustrates a cross-sectional view of an exemplary electronic device including light sensors and light emitters for measuring a user's physiological signal according to examples of the disclosure.

FIG. 3A illustrates a top view and FIG. 3B illustrates a cross-sectional view of an exemplary electronic device including light sensors and light emitters for measuring a user's physiological signal according to examples of the disclosure. Device 300 can include light emitter 306, light emitter 308, light emitter 316, light emitter 318, light sensor 304, and light sensor 314. Each light emitter can be optically coupled to each light sensor. For example, light emitter 306 can be optically coupled to both light sensor 304 and light sensor 314. Similarly, light emitter 316 can be optically coupled to both light sensor 304 and light sensor 314. Device 300 can be situated such that light sensor 304, light sensor 314, light emitter 306, light emitter 308, light emitter 316, and light emitter 318 are proximate to a skin 320 of a user. For example, device 300 can be held in the user's hand or strapped to the user's wrist, among other possibilities.

Light emitter 306 can be configured to emit light and generate one or more light paths detected by light sensor 304 and one or more light paths detected by light sensor 314. Light emitter 308 can also be configured to emit light and generate one or more light paths detected by light sensor 304 and one or more light paths detected by light sensor 314.

Light emitter 316 can be configured to emit light and generate one or more light paths detected by light sensor 304 and one or more light paths detected by light sensor 314. Light emitter 318 can also be configured to emit light and generate one or more light paths detected by light sensor 304 and one or more light paths detected by light sensor 314.

Device 300 can include a controller 309 configured to utilize the signal(s) from one or more lights paths to correct the signal(s) from one or more other lights paths to determine the user's physiological signal. The correction can be performed to cancel out any noise due to, for example, the user's motion, motions from within the user's body (e.g., tendon motion and/or muscle motion), tilt and/or pull of the device, ambient light variations, or any combination thereof. Device 300 can be in close proximity to skin 320 of a user and configured such that light emitter 306, light emitter 308, light emitter 316, and light emitter 318 can emit light towards skin 320. A plurality of blood vessels can be located in skin 320. For example, as illustrated in the FIG. 3B, one or more blood vessels 342 can be located in one or more deeper layers, such as layer 346 (e.g., the subcutaneous tissue), in skin 320, and one or more arterioles 334 can be located in one or more shallower layers, such as layer 345 (e.g., the dermis tissue), in skin 320.

In some examples, light emitter 306 and light sensor 304 can be located such that light path 322 emitted by light emitter 306 can reach layer 346 (e.g., a layer including the subcutaneous tissue), which can be located deeper within skin 320 than layer 345 (e.g., a layer including dermis tissue). A portion of light 322 can be absorbed by one or more arterioles 334 and/or one or more blood vessels 342 located in layer 345 and layer 346, and a portion of light (i.e., light 323) can reflect back for detection by light sensor 304. Light sensor 304 can generate signal 350, which can be measured by controller 309. Light emitter 308 and light sensor 304 can be located such that light 324 emitted by light emitter 308 can be sensitive to arterial blood volume changes. A portion of light 324 can be absorbed by one or more arterioles 334 in layer 345, and a portion of light (i.e., light 325) can reflect back for detection by light sensor 304. Light sensor 304 can generate signal 355, which can be measured by controller 309.

Signal 350 can include measured total signal (i.e., sum of the measured modulated light and unmodulated light) representative of light 323 detected by light sensor 304. Signal 355 can be the measured signal representative of light 325 detected by light sensor 304. In some examples, the user's motion (and/or motions from within the user's body (e.g., tendon motion and/or muscle motion)), can distort light 323 and light 325, which can change both signal 350 and signal 355. Since light 324 can be sensitive to arterial blood volume changes, signal 355 can include both pulsatile blood information and motion artifacts (e.g., non-pulsatile blood information from either deep or shallow tissue structures). Controller 309 can utilize an algorithm or simple mathematical functions can be applied to signal 350 and signal 355 to determine the user's physiological signal (e.g., signal 360 illustrated in FIG. 3C). However, given that light 324 can be absorbed by one or more arterioles 334, a portion of signal 355 may include pulsatile blood information. Thus, signal 355 may not be entirely representative of motion artifacts.

In some examples, the signals from one or more sets of light emitter-light sensor can be utilized to perform other functions. For example, light emitter 308 and/or light emitter 316 can be configured for monitoring off-wrist detection. In some examples, light emitter 308 and/or light emitter 316 can be configured to measure the background user's physiological signal (e.g., heart rate) when the user may not be moving. The system can monitor the user's motion through an accelerometer to determine whether the user is moving.

Figure 3C:
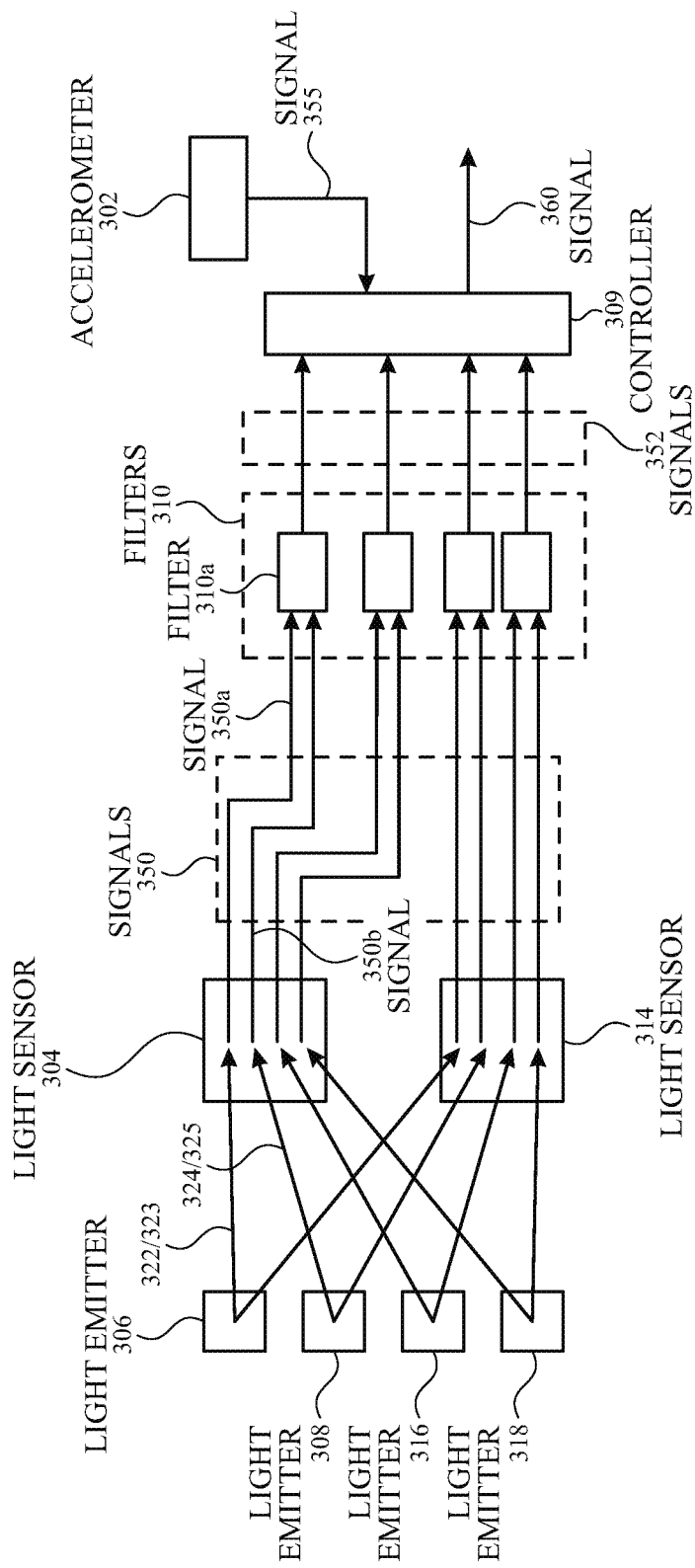
FIG. 3C illustrates exemplary circuitry coupled to the light sensors and light emitters and utilized for estimation of the user's physiological signals according to examples of the disclosure.
Figure 3D:
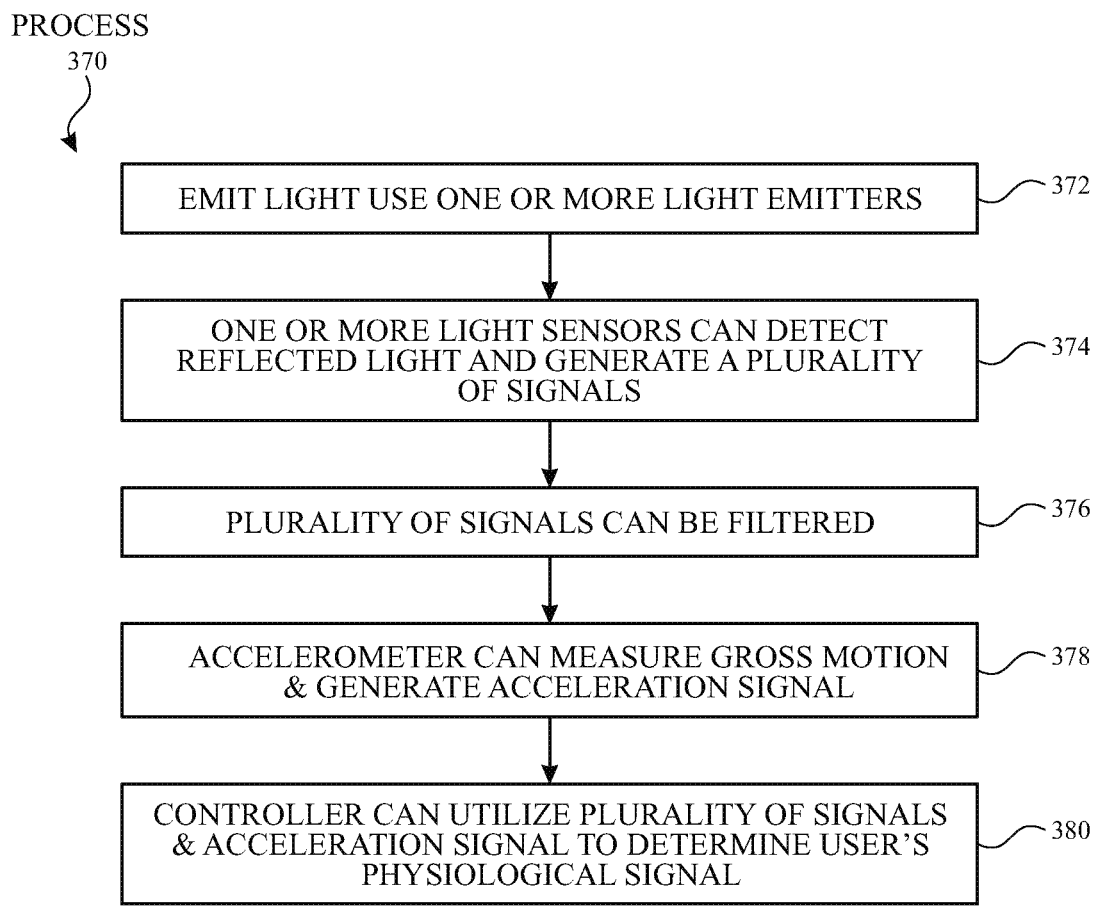
FIG. 3D illustrates an exemplary process flow for estimating the user's physiological signals according to example of the disclosure.

FIG. 3C illustrates exemplary circuitry coupled to the light sensors and light emitters and utilized for estimation of the user's physiological signals according to examples of the disclosure. FIG. 3D illustrates an exemplary corresponding process flow according to example of the disclosure. System 300 can include light emitter 306, light emitter 308, light emitter 316, and light emitter 318 configured to emit light (e.g., light 322 and light 324) towards the user (step 372 of process 370). A portion of the emitted light can reflect back (e.g., light 323 and light 325) towards one or more light sensors (e.g., light sensor 304 and/or light sensor 314). Light sensor 304 and light sensor 314 can be configured to generate a plurality of signals 350 in response to the detected reflected light (e.g., light 323 or light 325) (step 374 of process 370). System 300 can include a plurality of filters 310. Each filter 310 can be configured to receive a plurality of signals 350 from a light sensor and can filter the signals (step 376 of process 370). Plurality of filters 310 can be any type of filter capable of selection based on one or more properties, such as a bandpass filter capable of selecting a range of frequencies. In some examples, plurality of filters 310 can be adaptive filters. Each of the plurality of signals 350 generated from the light sensor can represent detected reflected light from different light emitters. For example, filter 310a can receive signal 350a and signal 350b. Signal 350a and signal 350b can be generated from light sensor 304, where signal 350a can represent detected reflected light from light emitter 306, and signal 350b can represent detected reflected light from light emitter 308. That is, signal 350a can represent signal information, and signal 350b can represent a noise reference channel. In some examples, for a given filter 310, the signal from one light emitter can represent the user's physiological signal and noise, and the signal from the other light emitter can represent noise. For example, light emitter 306 can be configured to emit light in the wavelength range of 495-570 nm, and signal 350a can represent the pulsatile blood volume changes of the user. Light emitter 308 can be configured to emit light in the wavelength range of 750-1400 nm, and the reflected light (e.g., light 325) can represent noise.

Plurality of signals 352 from plurality of filters 310 can be input into controller 309. System 300 can also include accelerometer 302. Accelerometer 302 can be configured to generate signal 355 indicative of the user's acceleration or gross motion (step 378 of process 370). Controller 309 can receive plurality of signals 352 from plurality of filters 310 and signal 355 from accelerometer 302 to determine the user's physiological signal 360 using one or more algorithms or simple mathematical functions (step 380 of process 370).

Figure 4A:
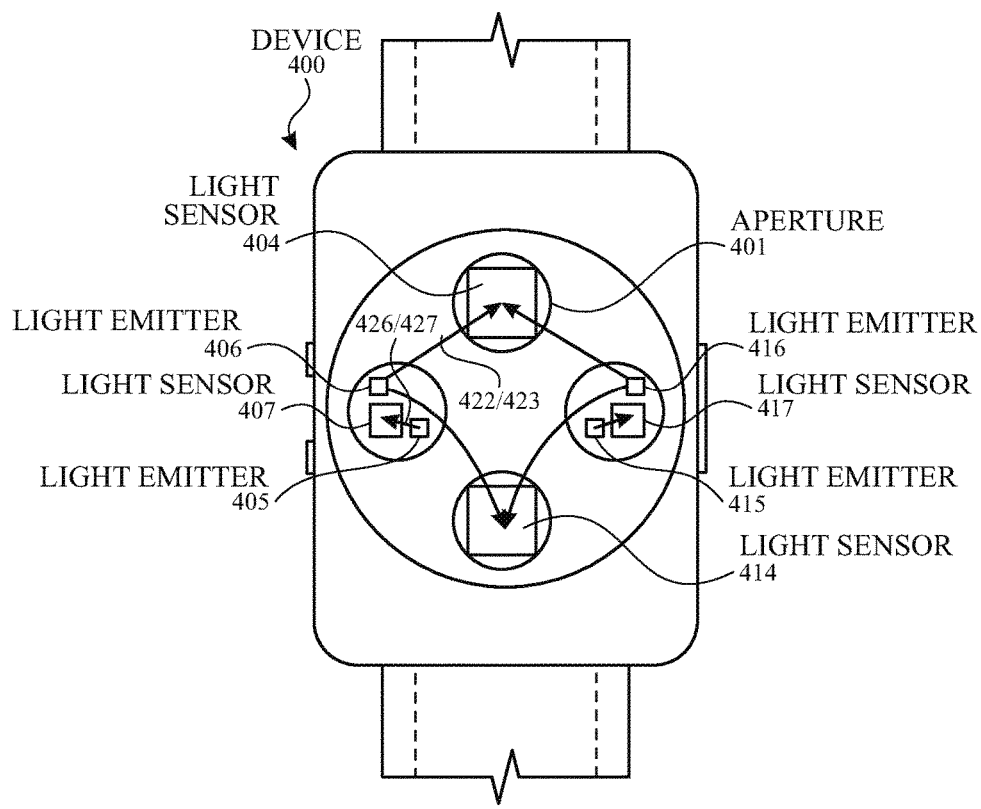
FIG. 4A illustrates a top view of an exemplary electronic device including a dedicated sensor and light emitter set for noise correction utilized in measuring a user's physiological signal according to examples of the disclosure.
Figure 4B:
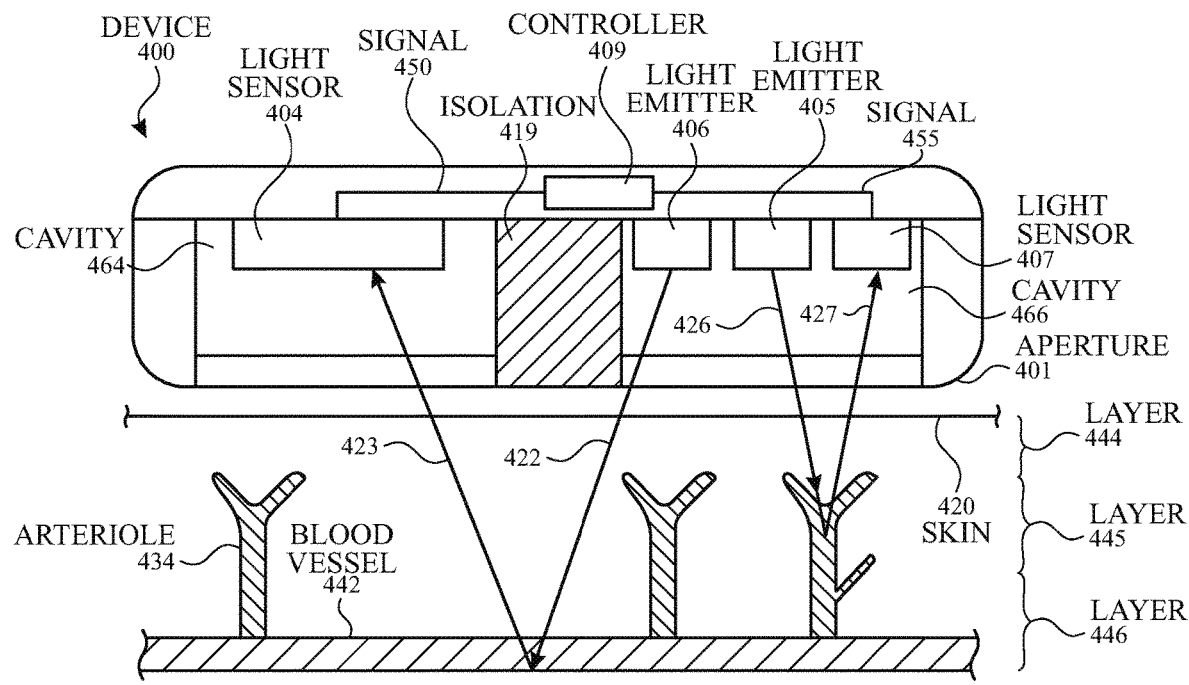
FIG. 4B illustrates a cross-sectional view of an exemplary electronic device including a dedicated light sensor and light emitter set for noise correction utilized in measuring a user's physiological signal according to examples of the disclosure.

FIG. 4A illustrates a top view and FIG. 4B illustrates a cross-sectional view of an exemplary electronic device including a dedicated light sensor and light emitter set for noise correction utilized in measuring a user's physiological signal according to examples of the disclosure. Device 400 can include light emitter 405, light emitter 406, light emitter 415, and light emitter 416. Device 400 can further include light sensor 404, light sensor 407, light sensor 414, and light sensor 417. Light emitter 406 can be configured to emit light towards light sensor 404 and light sensor 414. Light emitter 405 can be configured to emit light towards light sensor 407. Light emitter 416 can be configured to emit light towards light sensor 404 and light sensor 414. Light emitter 415 can be configured to emit light towards light sensor 414. In some examples, light emitter 406 and light emitter 416 can be located such that the path lengths to light sensor 404 are different from the path lengths to light sensor 414.

Device 400 can be configured such that one or more light emitters are optically coupled to one or more light sensors, where the one or more light emitters are located in a different cavity than the one or more light sensors. For example, light emitter 406 can be optically coupled to light sensor 404, where light emitter 406 can be located in cavity 466 and light sensor 404 can be located in cavity 464. In some examples, each cavity can be associated with a different aperture 401 (where light exits and enters device 400) and/or window. Device 400 can also be configured such that one or more light emitters can be optically coupled to one or more light sensors, where the one or more light emitters can be located in the same cavity as the one or more light sensors. For example, light emitter 405 can be optically coupled to light sensor 407, where both can be located in cavity 466. In some examples, the cavities included in device 400 can be separated by isolation 419.

In some examples, one or more sets of light emitter-light sensor located in different cavities can be configured to measure pulsatile blood volume changes. In some examples, one or more light emitter-light sensor sets located in the same cavity can be configured to measure non-pulsatile blood volume changes (from shallow tissues structures, deep tissue structures, or both) and/or serve as a noise reference channel. For example, the set comprising light emitter 406 and light sensor 404 can be configured to be sensitive to pulsatile blood volume changes. Light emitter 406 can emit light 422. Light 422 can be incident on blood vessel 442 located in layer 446, and a portion of the light can reflect back as light 423. Light sensor 404 can measure light 423 and can generate signal 450, where signal 450 can include both pulsatile blood volume changes and noise information. The set comprising light emitter 405 and light sensor 407 can be less sensitive to arterial blood volume changes (than the set comprising light emitter 406 and light sensor 404) and can be configured to generate a signal indicative of the non-pulsatile blood changes. Light emitter 405 can be located in close proximity (e.g., less than or equal to 1 mm away) to light sensor 407. Light emitter 405 can emit light 426. A portion of light 426 can penetrate through skin 420, and a portion of the light can reflect back as light 427. Light sensor 407 can detect light 427 and can generate signal 455, where signal 455 can include noise information. The spacing between light emitter 405 and light sensor 407 can prevent light 426 from reaching one or more deep layers (e.g., layer 446). Deeper tissue of a user can be more susceptible to motion artifacts due to, for example, muscle movement, tendon movement, non-pulsatile blood movement, or a combination thereof. The effect of the motion artifacts can be less pronounced in the superficial layers of the user due to absence of the muscles and tendons. In some examples, light 427 can be emitted at one or more wavelengths (e.g., greater than 600 nm) less sensitive to oxy-hemoglobin, which can reduce the interaction of light to venous blood volume changes. Controller 409 can receive signal 450 and signal 455 and can apply one or more algorithms to determine the user's physiological signal. Additional light paths formed between light sensors and light emitters can be included in examples of the disclosure and are not shown in the figure for clarity purposes.

Figure 4C:
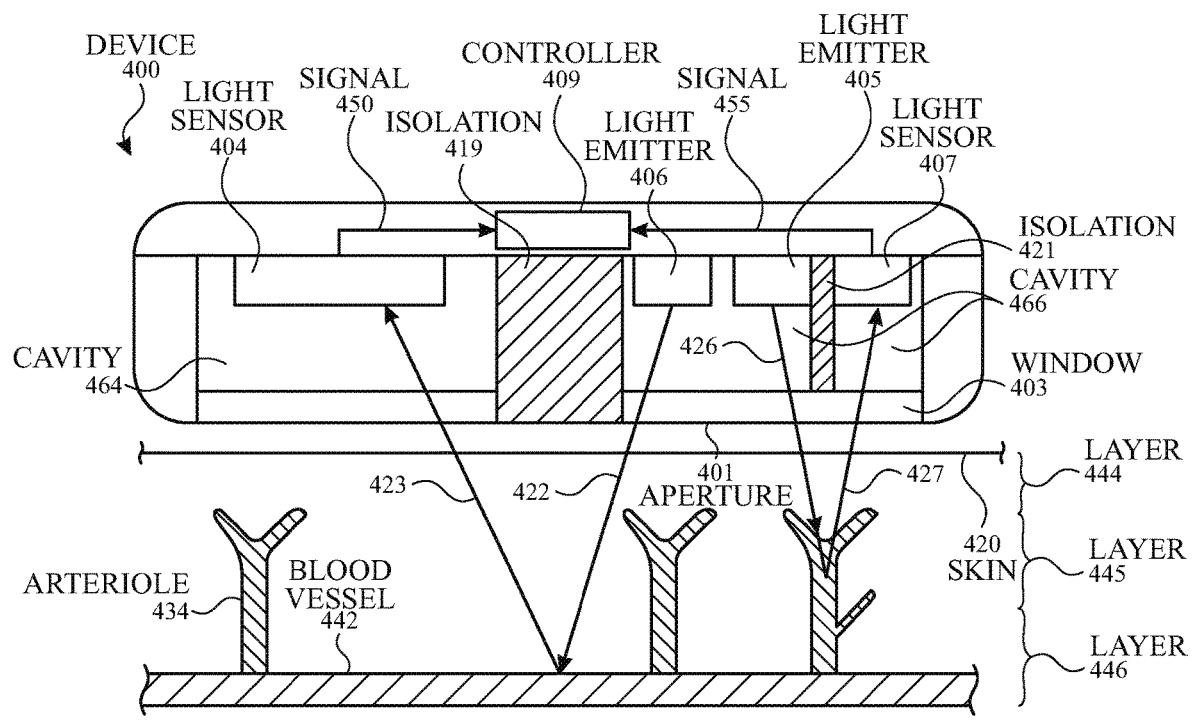
FIGS. 4C-4D illustrate cross-sectional views of exemplary electronic devices including a light sensor optically coupled to a light emitter in the same cavity, but divided by an isolation according to examples of the disclosure.

FIG. 4C illustrates a cross-sectional view of an exemplary electronic device including a light sensor optically coupled to a light emitter in the same cavity, but divided by an isolation according to examples of the disclosure. Device 400 can include isolation 421 located between a light emitter-light sensor set included in the same cavity (e.g., cavity 466). Isolation 421 can be any material configured to optically isolate light emitter 405 from light sensor 407. Exemplary materials for isolation can include, but are not limited to, carbon. In some examples, window 403 can be configured to reject one or more angles of light. In some examples, the rejected angles can include high angles (e.g., greater than 50 degrees) such that reflections from the surface of skin 420 and/or from the surface of window 403. In some examples, window 403 can be a Fresnel lens.

Figure 4D:
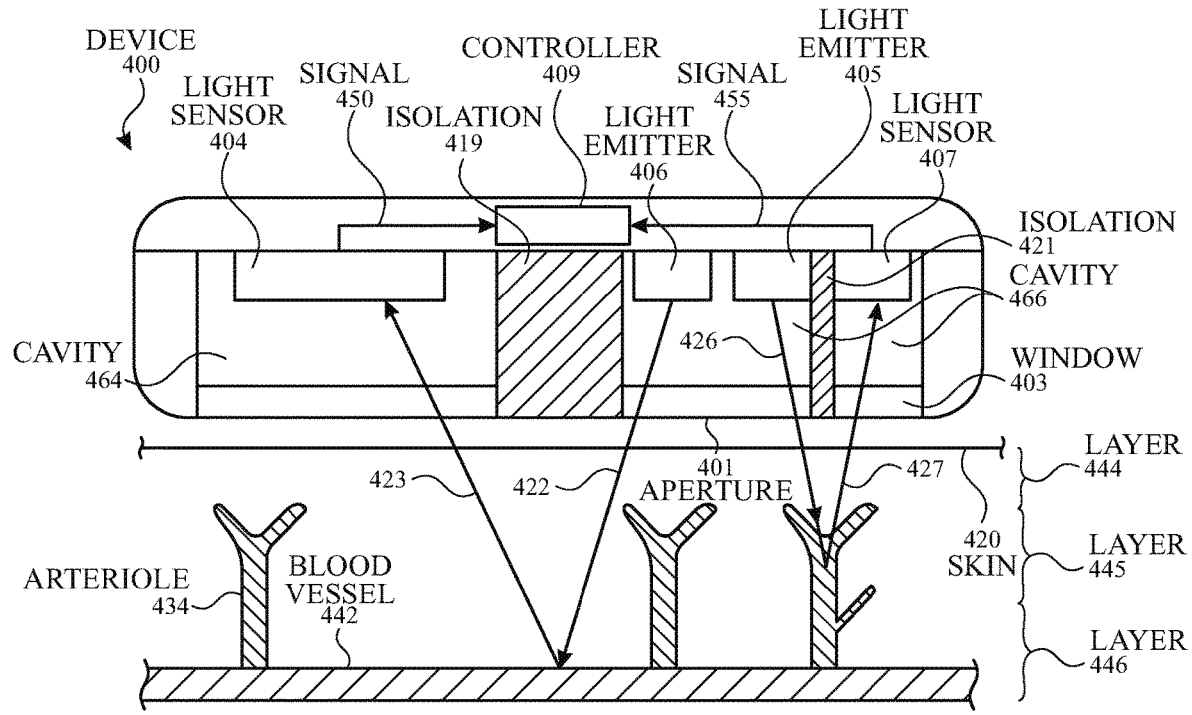

In some examples, device 400 can be located in close proximity (e.g., less than 5 mm away) or in contact with skin 420 to help prevent light 427 from including any light that has merely reflected off the surface of skin 420 and/or the surface of device 400. In this manner, penetration of light 426 can be better controlled. The close spacing of light emitter 405 and light sensor 407 can prevent the reflected light 427 from including non-pulsatile blood information. Isolation 421 and/or close proximity of the surface device 400 to skin 420 can prevent reflected light 427 from including reflections off the surface of skin 420 and/or surface of device 400. In some examples, the light sensor's numerical aperture can be configured to prevent light 427 from including any light that has merely reflected off the surface of skin 420 and/or the surface of device 400. Although FIG. 4C illustrates isolation 421 ending at the inner surface (i.e., surface closest to light emitter 405 and light sensor 407) of window 403, examples can include isolation 421 ending at the outer surface (i.e., surface furthest from light emitter 405 and light sensor 407) of window 403 as illustrated in FIG. 4D. In some examples, isolation 421 can comprise a plurality of materials, where the material(s) within the cavity can be different from the material(s) within the window. In some examples, isolation 421 can be continuous and/or the same material along the cavity and the window.

Figure 5A:
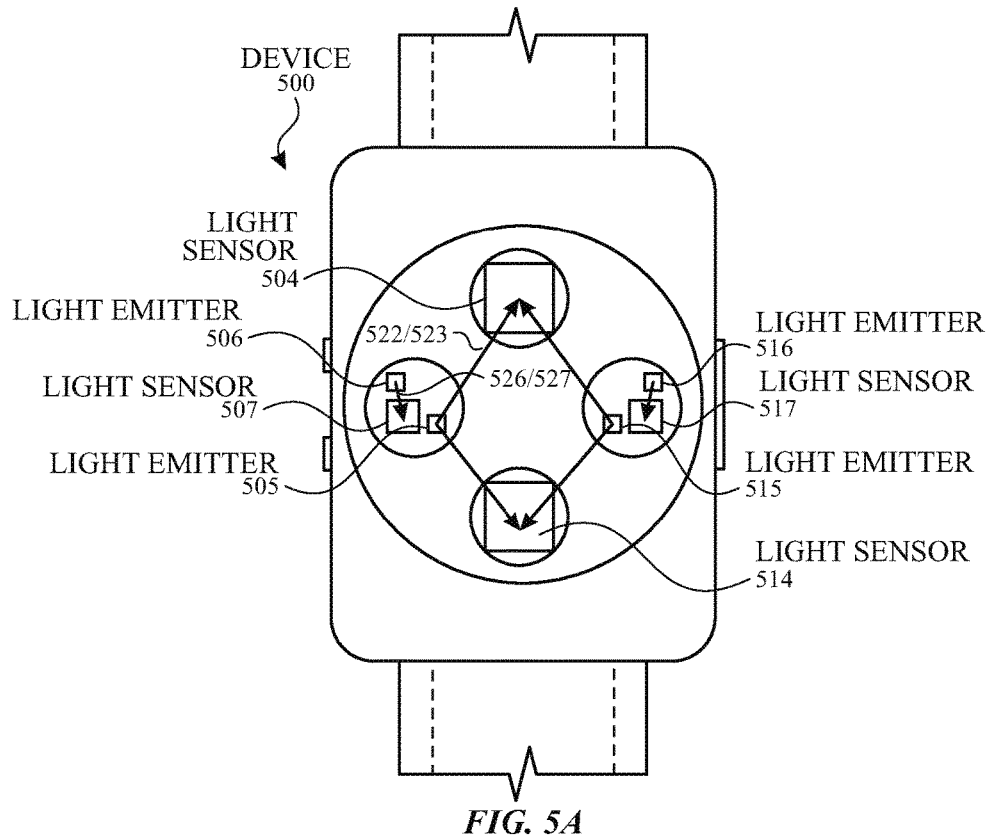
FIG. 5A illustrates a top view of an exemplary electronic device including at least one separate light sensor and light emitter set for noise correction utilized in measuring a user's physiological signal according to examples of the disclosure.
Figure 5B:
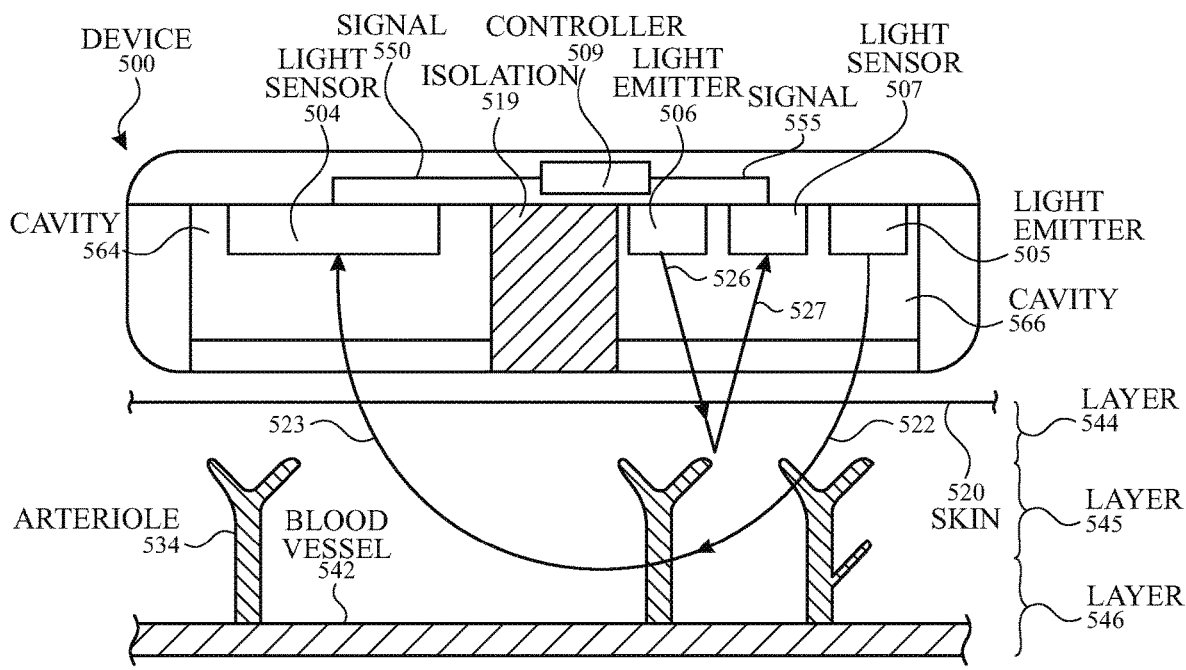
FIG. 5B illustrates a cross-sectional view of an exemplary electronic device including at least one separate light sensor and light emitter set for noise correction utilized in measuring a user's physiological signal according to examples of the disclosure.

FIG. 5A illustrates a top view and FIG. 5B illustrates a cross-sectional view of an exemplary electronic device including at least one separate light sensor and light emitter set for noise correction utilized in measuring a user's physiological signal according to examples of the disclosure. Device 500 can include light emitter 505, light emitter 506, light emitter 515, and light emitter 516. Device 500 can also include light sensor 504, light sensor 507, light sensor 514, and light sensor 517. Light emitter 505 can be configured to emit light towards light sensor 504 and light sensor 514. Light emitter 506 can be configured to emit light towards light sensor 507. Light emitter 515 can be configured to emit light towards light sensor 504 and light sensor 514. Light emitter 516 can be configured to emit light towards light sensor 517. In some examples, light emitter 505 and light emitter 515 can be located closer to the center of device 500, whereas light emitter 506, light sensor 507, light emitter 516, and light emitter 517 can be located closer to the outer edges of device 500. In some examples, light emitter 505 and light emitter 515 can be located such that the path lengths to light sensor 504 are the same as the path lengths to light sensor 514.

Device 500 can be configured such that one or more light emitters are optically coupled to one or more light sensors, where the one or more light emitters are located in a different cavity than the one or more light sensors. For example, light emitter 505 can be optically coupled to light sensor 504, where light emitter 505 can be located in cavity 566 and light sensor 504 can be located in a cavity 564. In some examples, each cavity can be associated with a different aperture (where light exits and enters the device) and/or window. Device 500 can also be configured such that one or more light emitters are optically coupled to one or more light sensors, where the one or more light emitters are located in the same cavity as the one or more light sensors. For example, light emitter 506 can be optically coupled to light sensor 507, where both can be located in cavity 566. In some examples, the cavities included in device 500 can be separated by isolation 519.

Similarly, light emitter 515 can be optically coupled to light sensor 504 and light sensor 514, where each light sensor can be located in a different cavity than light emitter 515. Light emitter 516 can be optically coupled to light sensor 517, where each can be located in the same cavity.

In some examples, one or more light emitter-light sensor sets located in different cavities can be configured to measure pulsatile blood volume changes. In some examples, one or more light emitter-light sensor sets located in the same cavity can be configured to measure non-pulsatile blood volume changes and/or serve as a noise reference channel. The set comprising light emitter 515 and light sensor 504 and/or the set comprising light emitter 515 and light sensor 514 can be configured to measure pulsatile blood changes. The signals generated from these sets can include both pulsatile blood volume changes and noise information. The set comprising light emitter 516 and light sensor 517 can be configured to measure non-pulsatile blood changes. Light emitter 516 can be located in close proximity (e.g., less than or equal to 1 mm away) from light sensor 517. The spacing between light emitter 516 and light sensor 517 can prevent the emitted light from reaching one or more arterioles 534 and/or one or more blood vessels 542, and hence, the associated signal can include little-to-no pulsatile blood information. Controller 509 can receive one or more signals that include pulsatile blood volume changes (e.g., signals, such as signal 550, from light sensor 504) and one or more signals that includes little-to-no pulsatile blood information (e.g., signals, such as signal 555, from light sensor 507) and can apply one or more algorithms to determine the user's physiological signal. Additional light paths formed between light sensors and light emitters can be included in examples of the disclosure and are not shown in the figure for clarity purposes.

Figure 5C:
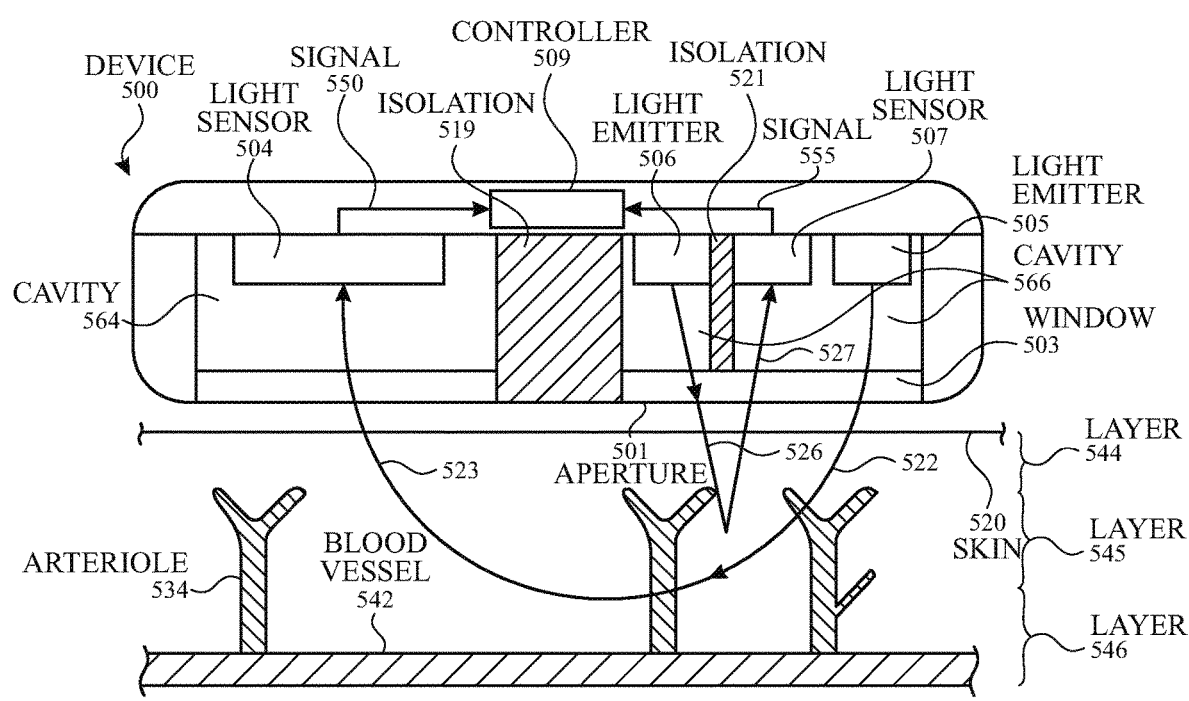
FIG. 5C illustrates a cross-sectional view of an exemplary electronic device including a light sensor optically coupled to a light emitter in the same cavity, but divided by an isolation according to examples of the disclosure.

FIG. 5C illustrates a cross-sectional view of an exemplary electronic device including a light sensor optically coupled to a light emitter in the same cavity, but divided by an isolation according to examples of the disclosure. Device 500 can further include isolation 521 located between a light emitter-light sensor set included in the same cavity. Isolation 521 can be any material configured to optically isolate light emitter 506 from light sensor 507. Exemplary materials for isolation can include, but are not limited to, carbon. In some examples, isolation 521 can be configured to focus and/or collimate light 526 such that light 526 can exit cavity 566 and/or aperture 501. In some examples, device 500 can be located in close proximity (e.g., less than 5 mm away) or in contact with skin 520 to help prevent light 527 from including any light that has merely reflected off the surface of skin 520 and/or surface of device 500. In this manner, the penetration of light 526 can be controlled. The close spacing of light emitter 506 and light sensor 507 can prevent reflected light 527 from including non-pulsatile blood information. Isolation 521 and/or close proximity of device 500 to skin 520 can prevent reflected light 527 from including reflections from the surface of skin 520 and/or surface of device 500. Although FIG. 5C illustrates isolation 521 ending at the inner surface (i.e., surface closest to light emitter 505 and light sensor 507) of window 503, examples can include isolation 521 ending at the outer surface (i.e., surface furthest from light emitter 505 and light sensor 507) of window 503 (not shown). In some examples, isolation can comprise a plurality of materials, where the material(s) within the cavity can be different from the material(s) within the window. In some examples, isolation can be continuous and/or the same material along the cavity and the window.

In some examples, light sensor 507 can be coupled to a passband filter and/or can be configured to detect only those wavelengths of light emitted by light emitter 506. In this manner, light sensor 507 may not detect light emitted from light emitter 505. In some examples, light sensor 507 can be configured to detect wavelengths of light emitted by light emitter 506 and wavelengths of light emitted by light emitter 505. In some examples, the different wavelengths of light can provide different types of information. For example, light emitter 506 can emit red light (or light within 570-750 nm), and light emitter 505 can emit green light (or light within 495-570 nm). Light sensor 507 can be configured to detect both red light and green light, where detected red light can be used for determining motion artifacts, and detected green light can be used for off-wrist detection. Moreover, light sensor 504 can detect light emitted from light emitter 505 that can pass through the multiple layers of skin 520 and pulsatile blood flow (i.e., one or more blood vessels 542 and/or one or more arterioles 534).

Although FIGS. 4A and 5A illustrate four light emitters, examples of the disclosure can include any number of light emitters. In addition, examples of the disclosure can include one or more common light sensors that can be used for detecting signals including pulsatile blood information and signals including non-pulsatile blood information.

Figure 6A:
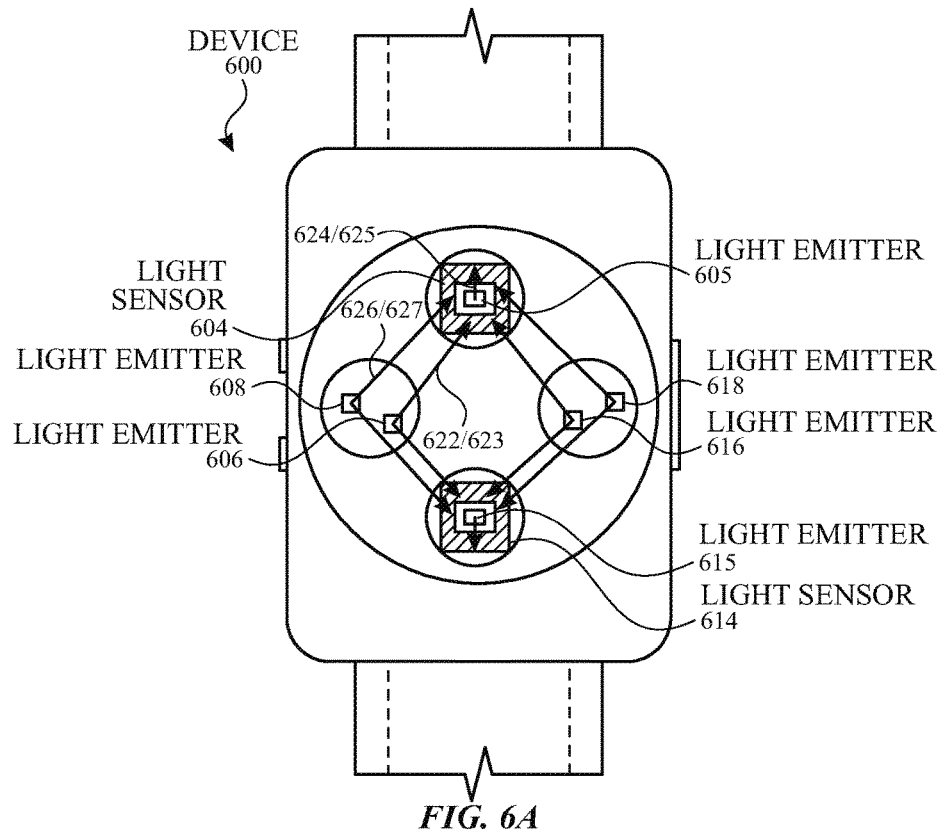
FIG. 6A illustrates a top view of an exemplary electronic device including a light sensor optically coupled to a common light emitter used for noise correction utilized in measuring a user's physiological signal according to examples of the disclosure.
Figure 6B:
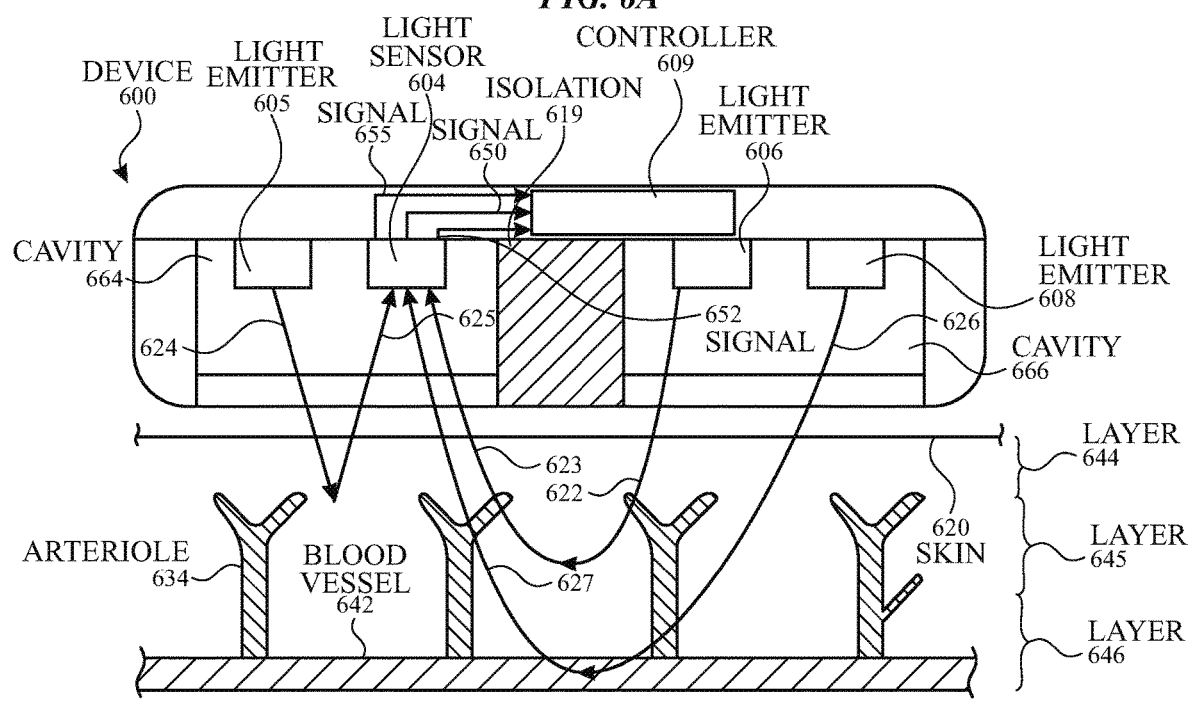
FIG. 6B illustrates a cross-sectional view of an exemplary electronic device including a light sensor optically coupled to a common light emitter used for noise correction utilized in measuring a user's physiological signal according to examples of the disclosure.

FIG. 6A illustrates a top view and FIG. 6B illustrates a cross-sectional view of an exemplary electronic device including a light sensor optically coupled to a common light emitter used for noise correction utilized in measuring a user's physiological signal according to examples of the disclosure. Device 600 can include light emitter 606, light emitter 608, light emitter 616, and light emitter 618. Device 600 can also include light sensor 604 and light sensor 614. Light emitter 606 can be configured to emit light towards light sensor 604 and light sensor 614. Light emitter 608 can also be configured to emit light towards light sensor 604 and light sensor 614. Light emitter 616 can be configured to emit light towards light sensor 604 and light sensor 614. Light emitter 618 can also be configured to emit light towards light sensor 604 and light sensor 614. In some examples, light emitter 606 and light emitter 616 can be located such that the path lengths to light sensor 604 and to light sensor 614 are the same. In some examples, light emitter 608 and light emitter 618 can be located such that the path lengths to light sensor 604 and to light sensor 614 are the same. In some examples, light emitter 606 and light emitter 616 can be located closer to the center of device 600 than light emitter 608 and light emitter 618.

Device 600 can further include light emitter 605 and light emitter 615. Light emitter 605 can be located in close proximity to and can be configured to emit light towards light sensor 604. Light emitter 615 can be located in close proximity to and can be configured to emit light towards light sensor 614. Light sensor 604 can be configured as a common light sensor that can detect light reflected from one or more blood vessels 642 and/or one or more arterioles 634, where pulsatile blood volume changes can be determined based on the detected reflect light. For example, pulsatile blood volume changes can affect light 623 and light 627. Light 623 can include information from layer 644 and layer 645, and light 627 can include information from layer 644, layer 645, and layer 646. Light sensor 604 can also detect light reflected from light 625, which can be sensitive to venous blood (non-pulsatile blood) volume changes due to the light emitter being located in close proximity (e.g., less than or equal to 1 mm away) to the light sensor and/or emitting light at specific wavelengths (e.g., greater than 600 nm), for example.

In some examples, light emitter 606 and light emitter 608 can be located in the same cavity 666, and light emitter 616 and light emitter 618 can be located in the same cavity. In each cavity, at least one light emitter can be configured to emit light at a wavelength different from another light emitter. Different types of information can be extracted from the different wavelengths of light. For example, light emitter 606 can be configured to emit light 622. Light 622 can travel through one or more layers of skin 620, and a portion of the light can reflect back as light 623 to be detected by light sensor 604. Light emitter 608 can be configured to emit light 626. Light 626 can travel through one or more layers of skin 620, and a portion of the light can reflect back as light 627 to be detected by light sensor 604. The separation distance between light emitter 606 and light sensor 604 can be shorter than the separation distance between light emitter 608 and light sensor 604. Additionally or alternatively, light 622 can have a shorter wavelength than the wavelength of light 626. In some examples, the shorter separation distance and/or shorter wavelength can lead to light 622 and light 623 having a shorter path length than light 626 and light 627. As a result, light 622/623 may not penetrate as deep in skin 620 as light 626/627. Light sensor 604 can generate a plurality of signals, including signal 652 representative of light 623, signal 650 representative of light 627, and signal 655 representative of light 625. Although FIG. 6A illustrates light emitter 605 and light emitter 615 located in a center of light sensor 604 and light sensor 614, respectively, examples of the disclosure can include light emitter 605 and light emitter 615 located in other locations (e.g., to one side) with respect to light sensor 604 and light sensor 614, respectively.

Figure 6C:
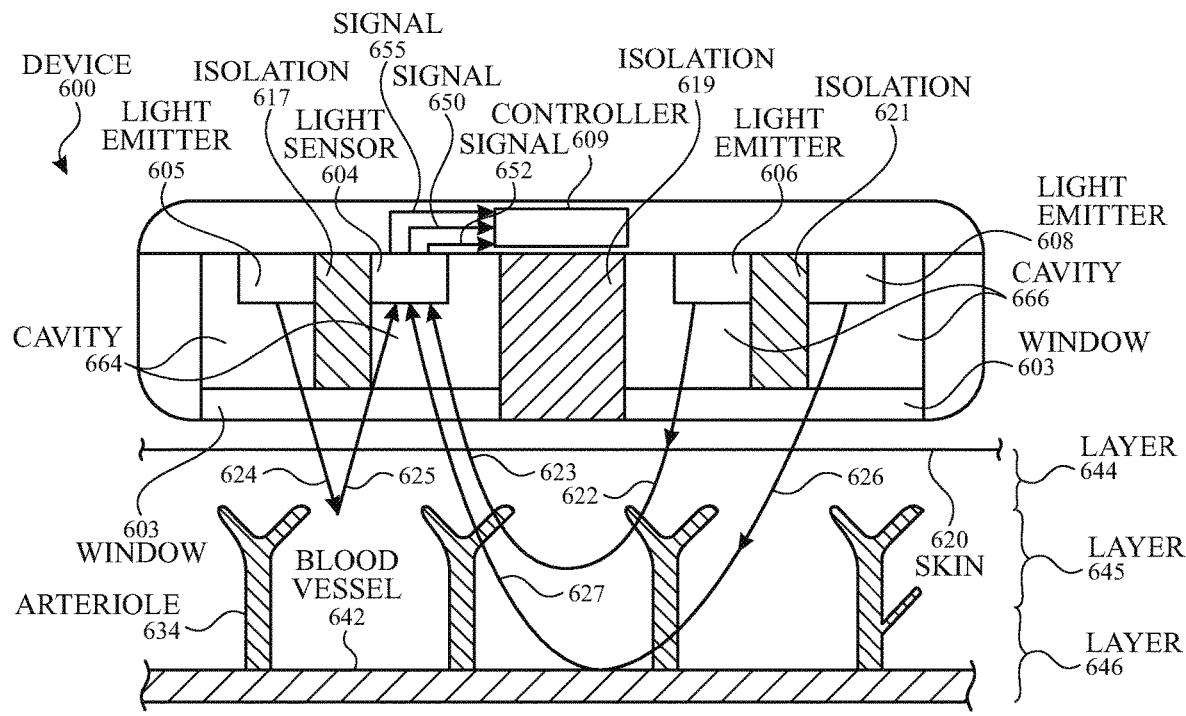
FIG. 6C illustrates a cross-sectional view of an exemplary electronic device including a light sensor optically coupled to a common light emitter used for noise correction utilized in measuring a user's physiological signal according to examples of the disclosure.

FIG. 6C illustrates a cross-sectional view of an exemplary electronic device including a light sensor optically coupled to a common light emitter used for noise correction utilized in measuring a user's physiological signal according to examples of the disclosure. Device 600 can include isolation 617 located between light emitter 605 and light sensor 604. Device 600 can also include isolation 621 located between light emitter 608 and light emitter 606. In some examples, isolation 621 can be configured to prevent light mixing between light emitted by light emitter 606 and light emitted by light emitter 608. Isolation 617 and isolation 621 can be any material configured for optical isolation. Exemplary materials for isolation can include, but are not limited to, carbon.

In some examples, isolation 617 can be configured to focus and/or collimate light 624 such that light 624 can exit cavity 664. In some examples, device 600 can be located in close proximity (e.g., less than 5 mm away) or in contact with skin 420 to help prevent light 625 from including any light that has merely reflected off the surface of skin 620 and/or the surface of device 600. In this manner, the penetration of light 624 can be controlled. The close spacing of light emitter 605 and light sensor 604 can prevent reflected light 625 from including pulsatile blood information. Isolation 617 and/or close proximity to the surface of device 600 to skin 620 can prevent reflected light 625 from including reflections from the surface of skin 620 and/or surface of device 600. Additionally or alternatively, isolation 621 can be configured to focus and/or collimate light 622 and/or light 626 such that light 622 and/or light 626 can exit cavity 666. Penetration of light 622 and light 626 can be controlled such that reflected light 623 and reflected light 627 can include pulsatile blood information.

Although FIG. 6C illustrates isolation 617 and isolation 621 ending at the inner surface (i.e., surface closest to light emitter 605, light sensor 604, light emitter 606, and light emitter 608) of windows 603, examples of the disclosure can include isolation 617 and/or isolation 621 ending at the outer surface (i.e., surface furthest from light emitter 605, light sensor 604, light emitter 606, and light emitter 608) of windows 603 (not shown). In some examples, isolation can comprise a plurality of materials, where the material(s) within the cavity can be different from the material(s) within window. In some examples, isolation can be continuous and/or the same material along the cavity and the window.

Figure 6D:
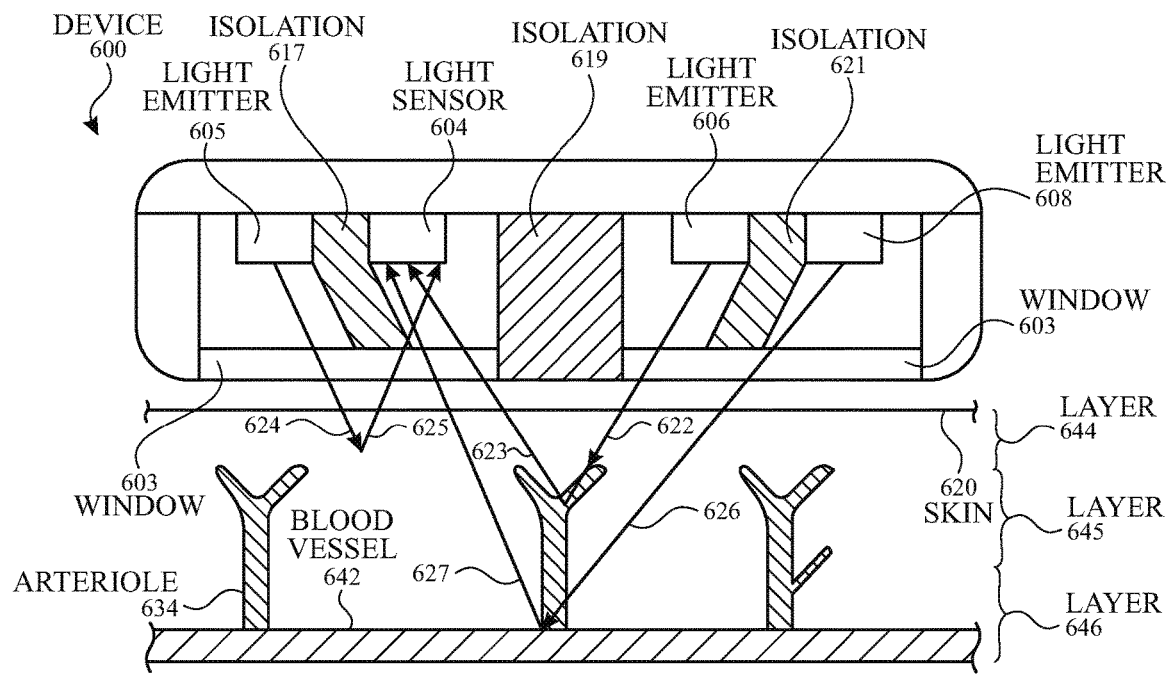
FIG. 6D illustrates a cross-sectional view of an exemplary electronic device including angled isolation according to examples of the disclosure.

FIG. 6D illustrates a cross-sectional view of an exemplary electronic device including angled isolation according to examples of the disclosure. Device 600 can include isolation 617 located between light sensor 604 and light emitter 605. Device 600 can also include isolation 621 located between light emitter 606 and light emitter 608. Isolation 617 and/or isolation 621 can be angled or non-orthogonal to windows 603, which can focus and/or collimate light 624 and light 626. In some examples, isolation 617 and isolation 621 can steer light 624 and light 626, respectively, more than isolation that is orthogonal to the windows (e.g., isolation 421 illustrated in FIG. 4D). In some examples, one or more of isolation 617 and isolation 621 can be angled towards (i.e., spacing between isolations can be located closer to the windows 603) isolation 619.

Figure 7A:
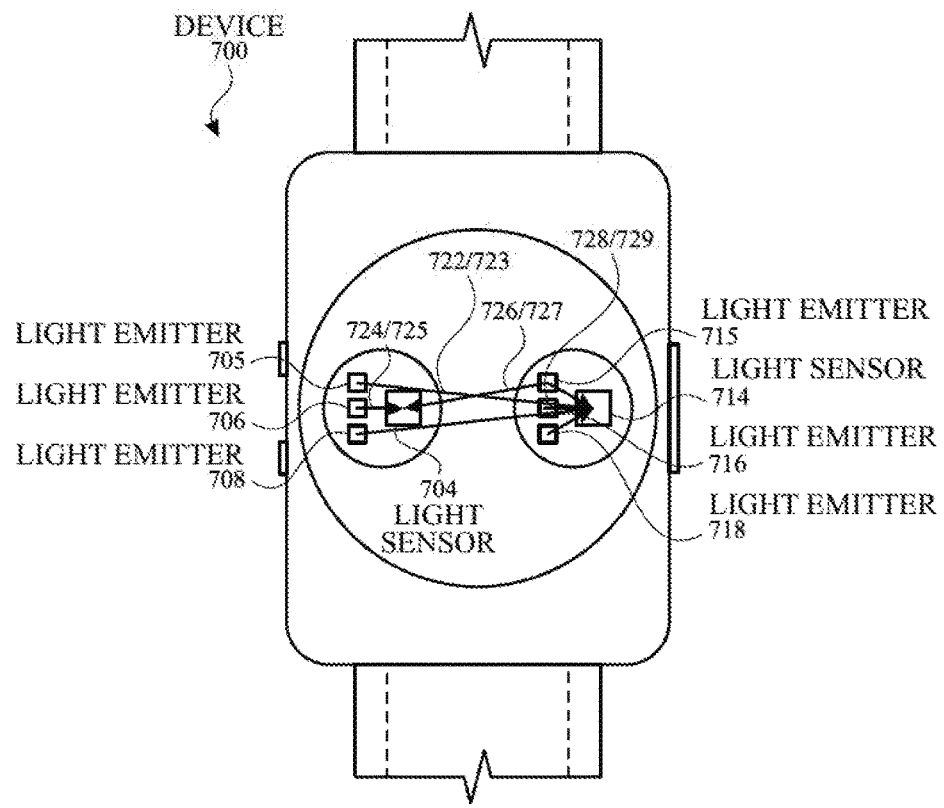
FIG. 7A illustrates a top view of an exemplary electronic device including at least two different cavities, each cavity can include at least one light sensor and a plurality of light emitters according to examples of the disclosure.
Figure 7B:
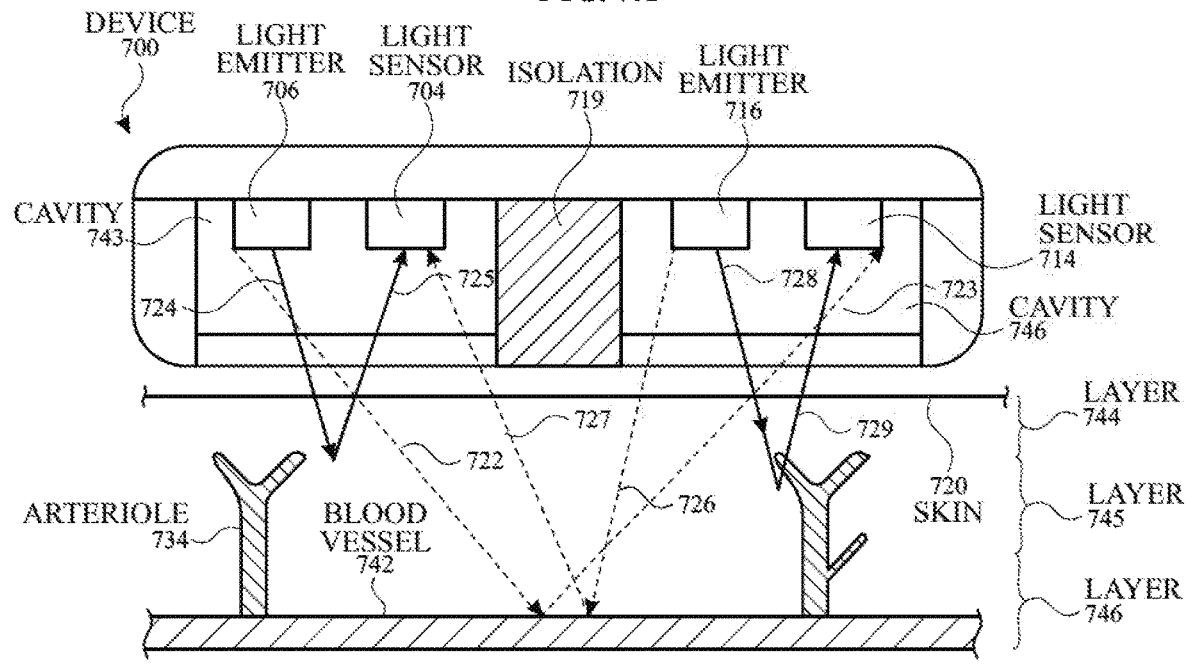
FIG. 7B illustrates a cross-sectional view of an exemplary electronic device including at least two different cavities, each cavity can include at least one light sensor and a plurality of light emitters according to examples of the disclosure.

FIG. 7A illustrates a top view and FIG. 7B illustrates a cross-sectional view of an exemplary electronic device including at least two different cavities, each cavity can include at least one light sensor and a plurality of light emitters according to examples of the disclosure. Device 700 can include cavity 743 and cavity 746. Cavity 743 can include light emitter 705, light emitter 706, light emitter 708, and light sensor 704. Cavity 746 can include light emitter 715, light emitter 716, light emitter 718, and light sensor 714. Device 700 can be configured such that each light sensor can be surrounded by light emitters and/or the edge of device 700. For example, light sensor 704 can be located between a first column of light emitters (e.g., column formed by light emitter 705, light emitter 706, and light emitter 708) and a second column of light emitters (e.g., column formed by light emitter 715, light emitter 716, and light emitter 718).

Device 700 can be configured such that in each cavity, at least one light emitter can be optically coupled to a light sensor in the cavity, and at least one light emitter can be optically coupled to a light sensor in another cavity. A plurality of overlapping light paths can be formed by the plurality of light emitted from light emitters that can be optically coupled to a light sensor in another cavity. In this manner, multiple light paths can "cross" over each other, which can increase the locations on skin 720 that can be sampled.

Light emitter 705 can be configured to emit light 722. Light 722 can enter skin 720, and a portion can reflect back as light 723 to be detected by light sensor 714, which can be a light sensor optically coupled to a light emitter in a different cavity. Light emitter 705 can be located relative to light sensor 714 such that one or more areas of skin 720 located along the optical path of light 722/723 can be measured. The measurement can include light 722 and/or light 723 undergoing optical changes due to pulsatile blood volume changes from, for example, one or more blood vessels 742 and/or one or more arterioles 734.

Light emitter 706 can be configured to emit light 724. Light 724 can enter skin 720, and a portion can reflect back as light 725 to be detected by light sensor 704, which can be a light sensor optically coupled to a light emitter in the same cavity. Light emitter 706 can be located in close proximity to light sensor 704 such that the penetration of light 724 can be limited to shallower layers (e.g., layer 744 and/or layer 745). In some examples, light 724 can include specific wavelengths (e.g., greater than 600 nm), thereby limiting light 724/725 to be sensitive to venous blood (non-pulsatile blood) volume changes.

Light emitter 715 can be configured to emit light 726. Light 726 can enter skin 720, and a portion can reflect back as light 727 to be detected by light sensor 704, which can be a light sensor optically coupled to a light emitter in a different cavity. Light emitter 715 can be located relative to light sensor 704 such that one or more areas of skin 720 located along the optical path of light 726/727 can be measured. The measurement can include light 726 and/or light 727 undergoing optical changes due to pulsatile blood volumes changes from, for example, one or more blood vessels 742 and/or one or more arterioles 734. In some examples, light emitter 715-light sensor 704 set can measure one or more areas of skin 720 different than the one or more areas of skin 720 measured by light emitter 705-light sensor 714 set. In some examples, one or more blood vessels 742 and/or one or more arterioles 734 measured by light 726/727 can be different from the one or more blood vessels 742 and/or one or more arterioles 734 measured by light 722/723. In some examples, the light path from light 722/723 can cross or intersect with the light path from light 726/light 727. The angle of intersection between the light paths can be adjusted based on the location of the corresponding optical components, which can then adjust the measurement profile of the one or more areas in skin 720.

Light emitter 716 can be configured to emit light 728. Light 728 can enter skin 720, and a portion can reflect back as light 729 to be detected by light sensor 714, which can be a light sensor optically coupled to a light emitter in the same cavity. Light emitter 716 can be located in close proximity (e.g., less than or equal to 1 mm away) to light sensor 714 such that the penetration of light 728 can be limited to shallower layers (e.g., layer 744 and/or layer 745). In some examples, light 728/729 can include specific wavelengths (e.g., greater than 600 nm), thereby limiting the sensitivity of light 728/729 to venous blood (non-pulsatile blood) volume changes. In some examples, the separation distance between light emitter 706 and light sensor 704 can be the same as the separation distance between light emitter 716 and light sensor 714. In some examples, the separation distance between light emitter 706 and light sensor 704 can be different from the separation distance between light emitter 716 and light sensor 714. In some examples, light 725 can include the same noise artifacts as light 729. In some examples, light 725 can include different noise artifacts than light 729. If the noise artifacts are different, then device 700 can utilize the difference in noise artifacts to determine whether the noise originates from multiple sources. For example, a difference in noise artifacts can be indicative of a tilt and/or pull experienced by one side of the device and not by the other side of the device. Additional light paths formed between light sensors and light emitters can be included in examples of the disclosure and are not shown in the figure for clarity purposes.

Figure 7C:
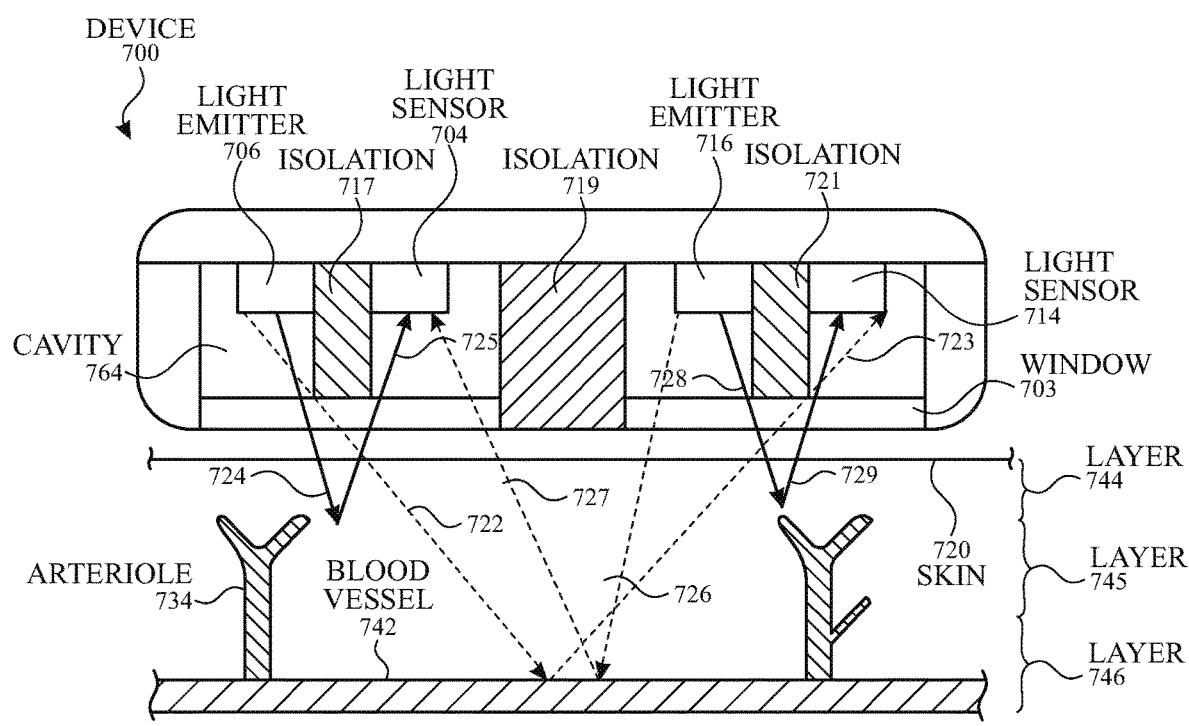
FIG. 7C illustrates a cross-sectional view of an exemplary electronic device including at least two different cavities, each cavity including at least one light sensor and a plurality of light emitters divided by an isolation according to examples of the disclosure.

FIG. 7C illustrates a cross-sectional view of an exemplary electronic device including at least two different cavities, each cavity including at least one light sensor and a plurality of light emitters divided by an isolation according to examples of the disclosure. To prevent light 725 and/or light 729 from including reflected light at the interfaces (e.g., at the surface of skin 720, at the surface of window 703, and/or at the surface of device 700), device 700 can include isolation 717 and/or isolation 721. In this manner, light 725 and/or light 729 can include information related to non-pulsatile blood and/or other noise artifacts (e.g., noise from a tilt and/or pull of the device or ambient light variations).

Figure 8A:
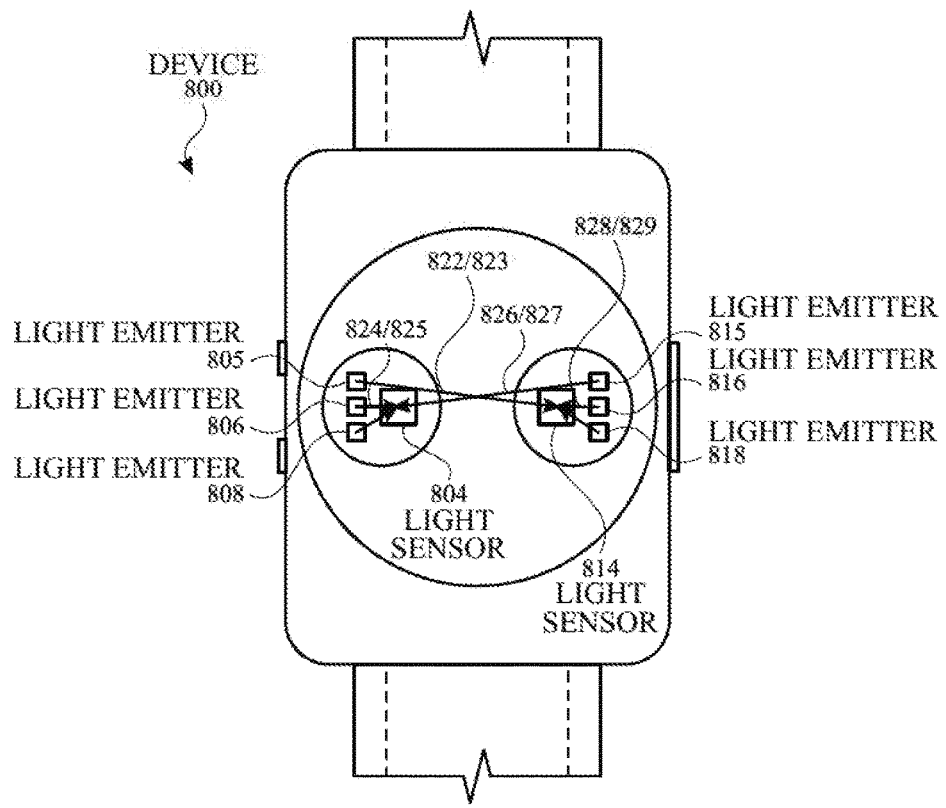
FIG. 8A illustrates a top view of an exemplary electronic device including at least two different cavities, each cavity including at least one light sensor and a plurality of light emitters according to examples of the disclosure.
Figure 8B:
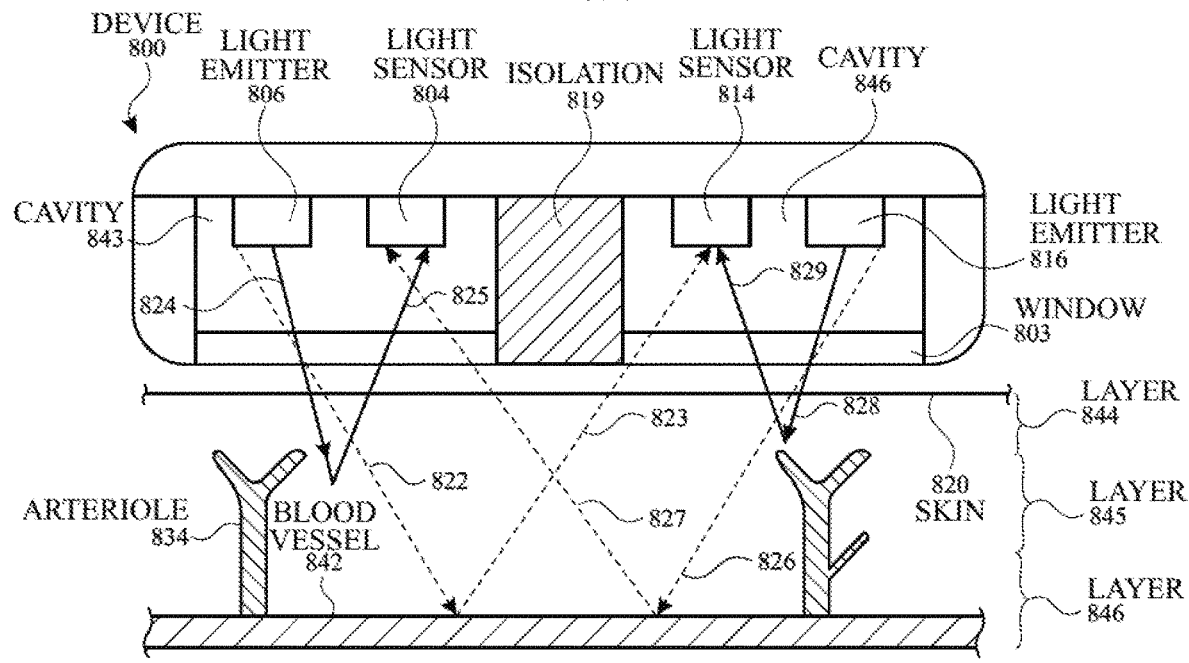
FIG. 8B illustrates a cross-sectional view of an exemplary electronic device including at least two different cavities, each cavity including at least one light sensor and a plurality of light emitters according to examples of the disclosure.

FIG. 8A illustrates a top view and FIG. 8B illustrates a cross-sectional view of an exemplary electronic device including at least two different cavities, each cavity including at least one light sensor and a plurality of light emitters according to examples of the disclosure. Device 800 can include cavity 843 and cavity 846. Cavity 843 can include light emitter 805, light emitter 806, light emitter 808, and light sensor 804. Cavity 846 can include light emitter 815, light emitter 816, light emitter 818, and light sensor 814. Device 800 can be configured such that light sensor 804 and light sensor 814 are adjacent optical components. In some examples, light sensor 804 and light sensor 814 can be symmetrically (horizontally) placed on device 800 with respect to its center. Light emitter 805, light emitter 806, and light emitter 808 can be located on one side of device 800, and light emitter 815, light emitter 816, and light emitter 818 can be located on the opposite side of device 800.

Device 800 can be configured such that in each cavity, at least one light emitter can be optically coupled to a light sensor in the cavity, and at least one light emitter can be optically coupled to a light sensor in another cavity. A plurality of overlapping light paths can be formed by the plurality of light emitted from light emitters that can be optically coupled to a light sensor in another cavity. In this manner, multiple light paths can "cross" over each other, which can increase the locations within skin 820 that device 800 can sample.

Light emitter 805 can be configured to emit light 822. Light 822 can enter skin 820, and a portion can reflect back as light 823 to be detected by light sensor 814, which can be a light sensor optically coupled to a light emitter in a different cavity. Light emitter 805 can be located relative to light sensor 814 such that one or more areas of skin 820 located along the optical path of light 822/823 can be measured. The measurement can include light 822 and/or light 823 undergoing optical changes due to pulsatile blood volume changes from, for example, one or more blood vessels 842 and/or one or more arterioles 834.

Light emitter 806 can be configured to emit light 824. Light 824 can enter skin 820, and a portion can reflect back as light 825 to be detected by light sensor 804, which can be a light sensor optically coupled to a light emitter in the same cavity. Light emitter 806 can be located in close proximity (e.g., less than or equal to 1 mm away) to light sensor 804 such that the penetration of light 824 can be limited to shallower layers (e.g., layer 844 and/or layer 845). Light 824/825 can include specific wavelengths (e.g., greater than 600 nm), thereby limiting the sensitivity of light 824/825 to venous blood (non-pulsatile blood) volume changes.

Light emitter 815 can be configured to emit light 826. Light 826 can enter skin 820, and a portion can reflect back as light 827 to be detected by light sensor 804, which can be a light sensor optically coupled to a light emitter in a different cavity. Light emitter 816 can be located relative to light sensor 804 such that one or more areas of skin 820 located along the optical path of light 826/827 can be measured. The measurement can include light 826 and/or light 827 undergoing optical changes due to pulsatile blood volumes changes from, for example, one or more blood vessels 842 and/or one or more arterioles 834. In some examples, light emitter 815-light sensor 804 set can measure one or more areas of skin 820 different than the one or more areas of skin 820 measured by light emitter 805-light sensor 814 set. In some examples, one or more blood vessels 842 and/or one or more arterioles 834 measured by light 826/827 can be different than the one or more blood vessels 842 and/or one or more arterioles 834 measured by light 822/823. In some examples, the light path from light 822/823 can cross or intersect with the light path from light 826/827. The angle of intersection between the light paths can be adjusted based on the location of the corresponding optical components, which can then adjust the measurement profile of the one or more areas in skin 820. By locating light emitters (e.g., light emitter 805, light emitter 806, and light emitter 808) on one side of device 800 and locating light emitters (e.g., light emitter 815, light emitter 816, and light emitter 818) on another side of device 800, the light paths can have a greater separation distance relative to one another (compared to, for example, the light paths illustrated in FIG. 7B). Different characteristics (e.g., size, shape, and/or location) of the measurement areas on the skin 820 can be obtained.

Light emitter 816 can be configured to emit light 828. Light 828 can enter skin 820, and a portion can reflect back as light 829 to be detected by light sensor 814, which can be a light sensor optically coupled to a light emitter in the same cavity. Light emitter 816 can be located in close proximity (e.g., less than or equal to 1 mm away) to light sensor 814 such that the penetration of light 828 can be limited to shallower layers (e.g., layer 844 and/or layer 845). Light 828/829 can include specific wavelengths (e.g., greater than 600 nm), thereby limiting the sensitivity of light 828/829 to venous blood (non-pulsatile blood) volume changes. In some examples, the separation distance between light emitter 816 and light sensor 814 can be the same as the separation distance between light emitter 806 and light sensor 804. In some examples, the separation distance between light emitter 816 and light sensor 814 can be different from the separation distance between light emitter 806 and light sensor 804. In some examples, light 825 can include the same noise artifacts as light 829. In some examples, light 825 can include different noise artifacts than light 829. If the noise artifacts are different, then device 800 can utilize the difference in noise artifacts to determine whether the noise originates from multiple sources. For example, a difference in noise artifacts can be indicative of a tilt and/or pull experienced by one side of the device and not the other.

In some examples, the system can be configured with a plurality of sets of light emitter-light sensor, where the light emitters and light sensors have a common optical axis. For example, light emitter 806 can be configured to emit light towards light sensor 814. Multiple light paths can exist. For example, one light path can be between light emitter 806 and light sensor 804, and another light path can be between light emitter 806 and light sensor 814. The light path between light emitter 806 and light sensor 804 can be utilized for noise correction, and the light path between light emitter 806 and light sensor 814 can be utilized for pulsatile blood information. Additional light paths formed between light sensors and light emitters can be included in examples of the disclosure and are not shown in the figure for clarity purposes.

Figure 8C:
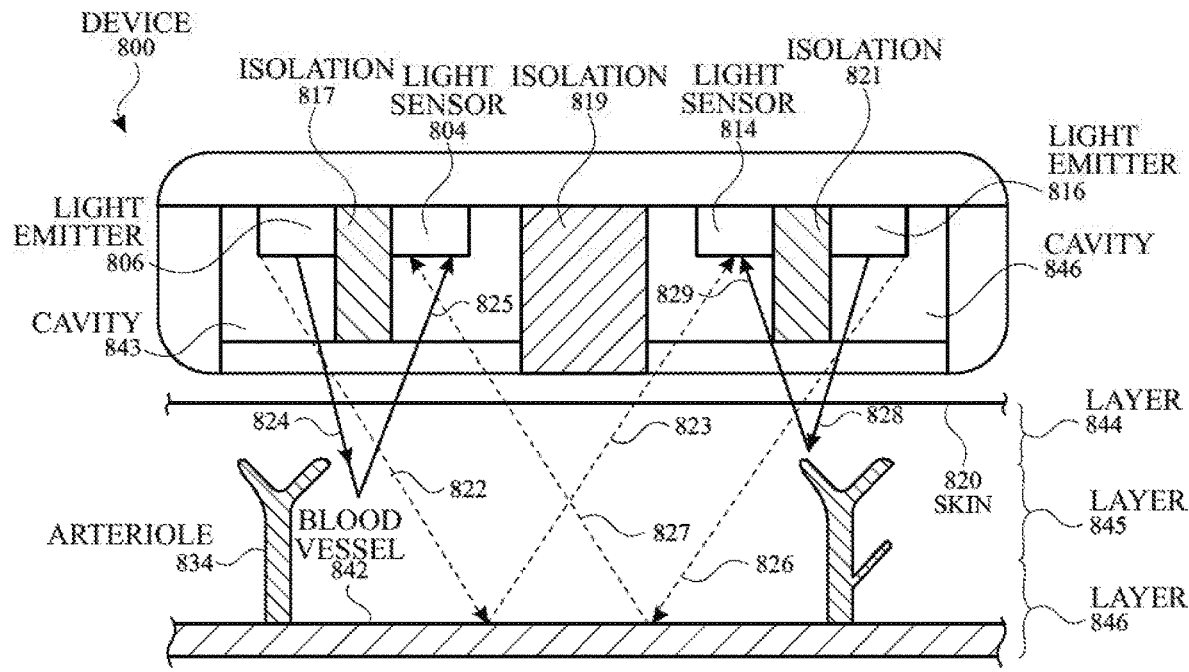
FIG. 8C illustrates a cross-sectional view of an exemplary electronic device including at least two different cavities, each cavity including at least one light sensor and a plurality of light emitters divided by an isolation according to examples of the disclosure.

FIG. 8C illustrates a cross-sectional view of an exemplary electronic device including at least two different cavities, each cavity including at least one light sensor and a plurality of light emitters divided by an isolation according to examples of the disclosure. To prevent light 825 and/or light 829 from including reflected light at the interfaces (e.g., at the surface of skin 820, at the surface of window 803, at the surface of device 800), device 800 can include isolation 817 and/or isolation 821. In this manner, light 825 and/or light 829 can include non-pulsatile blood information. In some examples, light 825 and/or light 829 can exclude pulsatile blood information.

Figure 8D:
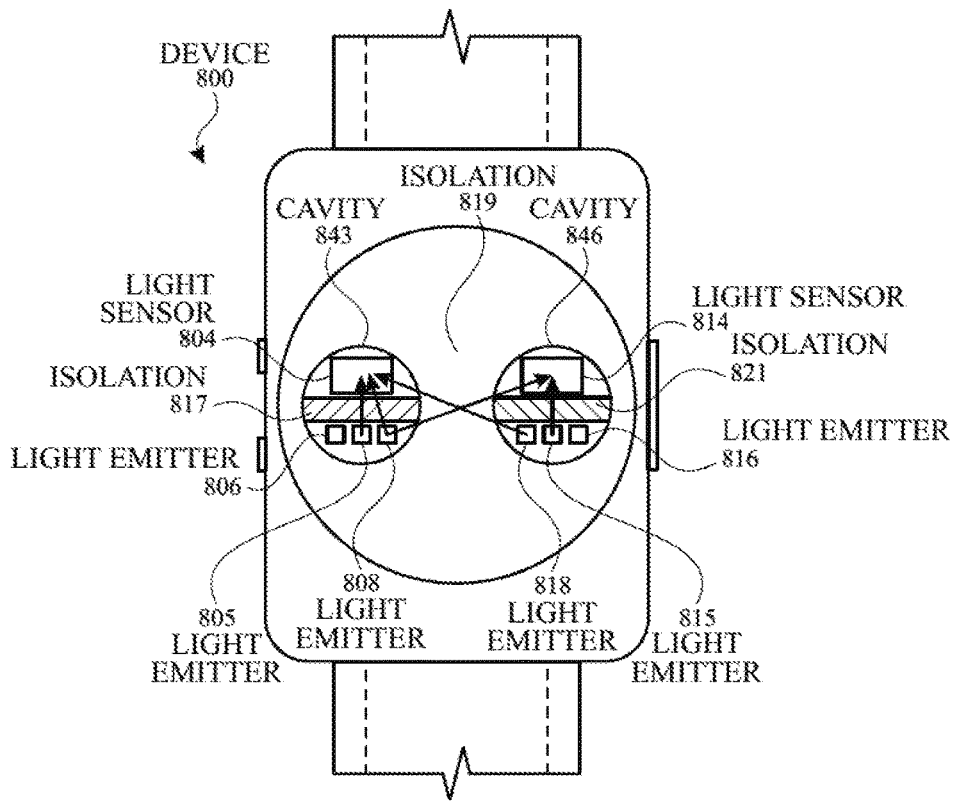
FIGS. 8D-8F illustrate top views of exemplary configurations for light emitters, light sensors, and isolation for electronic devices according to examples of the disclosure.
Figure 8E:
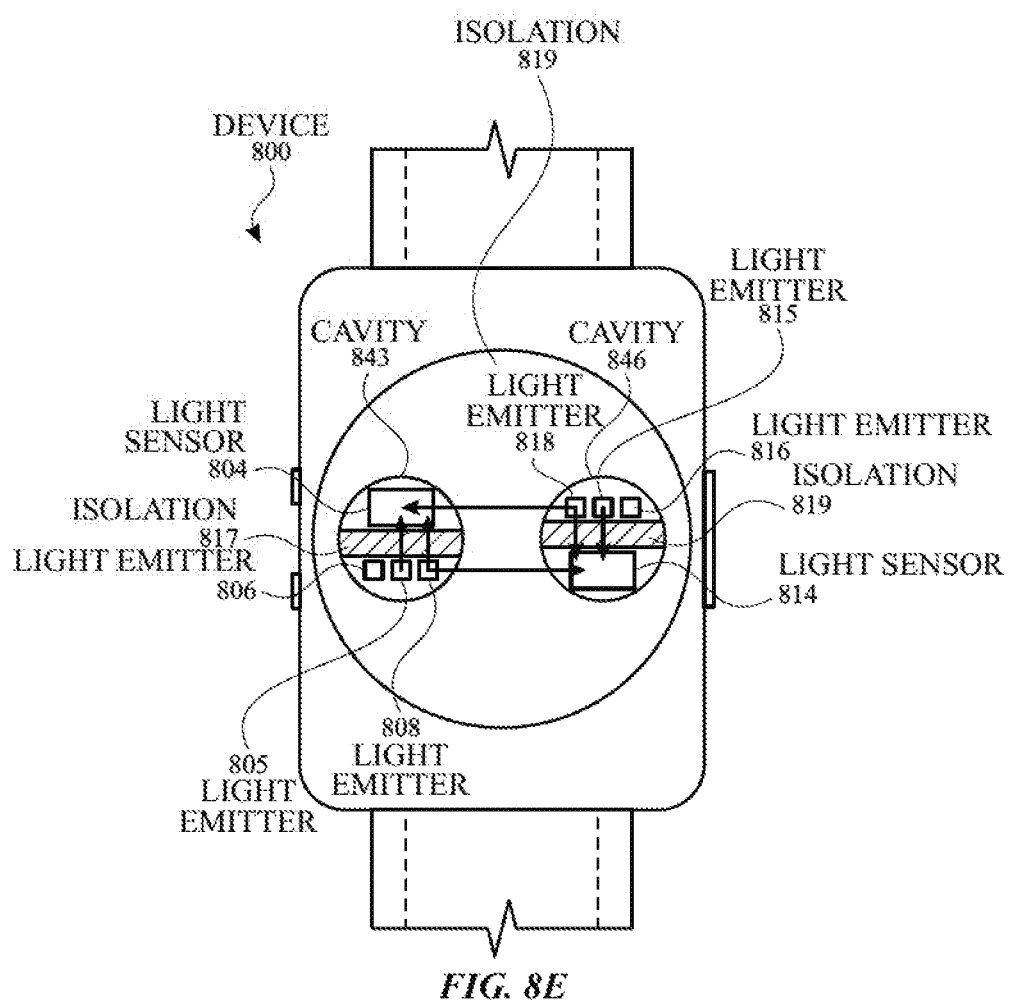

Although FIGS. 7A and 8A illustrate the light emitters arranged to form columns (relative to the long axis of device 700 and device 800), examples of the disclosure can include the light emitters arranged to form rows. FIGS. 8D-8E illustrate top views of exemplary configurations for light emitters, light sensors, and isolation for electronic devices according to examples of the disclosure. As illustrated in FIG. 8D, light sensor 804 and light sensor 814 can be located on one side of device 800, and the rows of light emitters (e.g., row formed by light emitter 805, light emitter 806, and light emitter 808 and row formed by light emitter 815, light emitter 816, and light emitter 818) can be located on another side of device 800. The light sensors and rows of light emitters can be separated by isolation 817 and isolation 821. Additionally, cavity 843 can and cavity 846 can be separated by isolation 819. The configuration can lead to one or more intersection light paths. Additional light paths formed between light sensors and light emitters can be included in examples of the disclosure and are not shown in the figure for clarity purposes.

As illustrated in FIG. 8E, light sensor 804 and one row of light emitters (e.g., row formed by light emitter 815, light emitter 816, and light emitter 818) can be located on one side of device 800. Additionally, light sensor 814 and another row of light emitters (e.g., row formed by light emitter 805, light emitter 806, and light emitter 808) can be located on another side of device 800. Each row of light emitters can be divided by isolation (e.g., isolation 817 or isolation 821) from a light sensor. This configuration can lead to non-overlapping light paths as shown in the figure. Additional light paths formed between light sensors and light emitters can be included in examples of the disclosure and are not shown in the figure for clarity purposes.

Figure 8F:
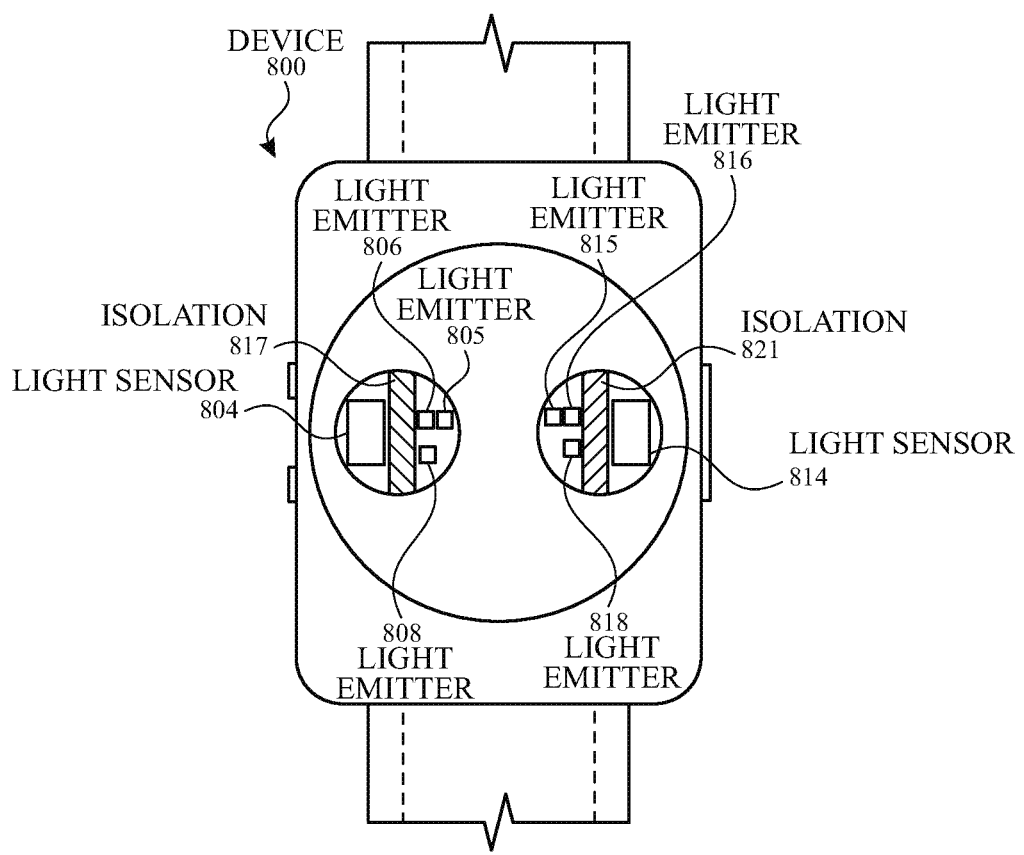

Examples of the disclosure are not limited to rows of light emitters, but can include any configurations such as illustrated in FIG. 8F. For example, light emitter 805 and light emitter 806 can be located in a row different from light emitter 808. Light emitter 808 can be located in the same column as light emitter 805 or light emitter 806 or can be located in a column different from light emitter 805 and light emitter 806. Similarly, light emitter 815 and light emitter 816 can be located in a row different from light emitter 818. Light emitter 818 can be located in the same column as light emitter 815, or light emitter 816 or can be located in a column different from light emitter 815 and light emitter 818. In some examples, the light emitters and light sensors can be symmetrically located (e.g., light sensor 804 can be located the same distance away from the center of the device as light sensor 814) with respect to the center of device 800. In some examples, the light emitters and light sensors can be asymmetrically located with respect to the center of device 800. In some examples, the light sensors can be located closer to the edges of device 800 than the light emitters. In some examples, the light emitters can be located closer to the edges of device 800 than the light sensors. Additional light paths formed between light sensors and light emitters can be included in examples of the disclosure and are not shown in the figure for clarity purposes.

Figure 9A:
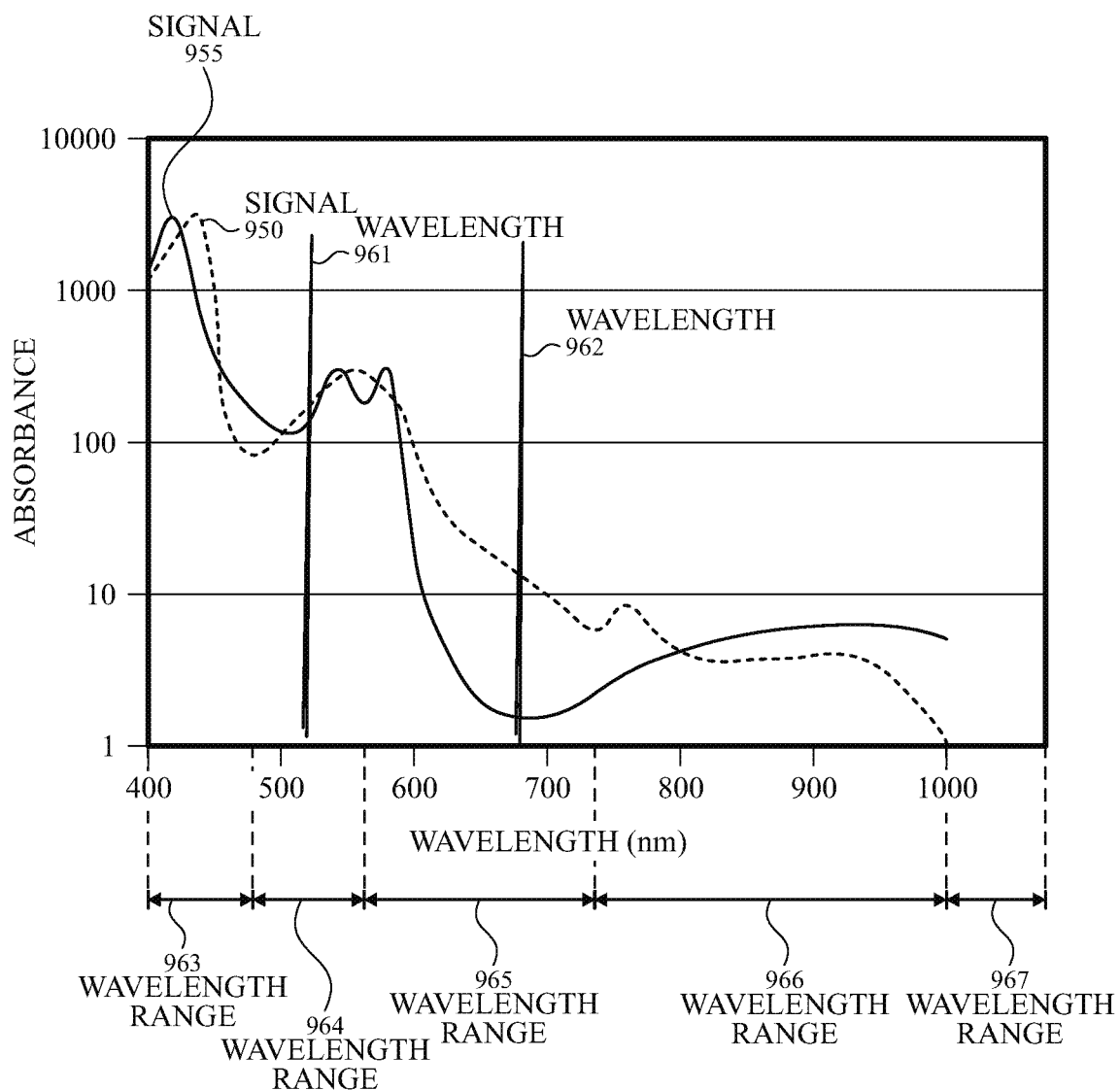
FIG. 9A illustrates exemplary oxy-hemoglobin and deoxy-hemoglobin absorption signals measured across a plurality of wavelengths according to examples of the disclosure.

FIG. 9A illustrates exemplary oxy-hemoglobin and deoxy-hemoglobin absorption signals measured across a plurality of wavelengths according to examples of the disclosure. The spectrum can include a plurality of wavelength ranges, such as wavelength range 963, wavelength range 964, wavelength range 965, wavelength range 966, and wavelength range 967. Signal 950 can include the oxy-hemoglobin absorbance signal, and signal 955 can include the deoxy-hemoglobin absorbance signal. At one or more wavelengths (e.g., wavelength 961) in the spectrum, signal 950 and signal 955 can intersect. That is, signal 950 and signal 955 can have the same or similar absorbance values. A PPG system configured to measure the user's physiological signal at or within close proximity to these one or more wavelengths (e.g., wavelength 961 corresponding to an intersection of the signals) may not be capable of discerning whether the measured reflected light associated originates from oxy absorbance or de-oxy absorbance.

Examples of the disclosure can include a system capable of measuring both oxy-hemoglobin and deoxy-hemoglobin absorbance values in one or more wavelength ranges, where the oxy-hemoglobin and deoxy-hemoglobin absorbance signals are non-intersecting. In some examples, the system can be configured to measure at one or more wavelengths where the difference in absorbance values of the signals are greater than a pre-determined threshold (e.g., 10% difference). In some examples, the one or more measured wavelengths (e.g., wavelength 962) can correspond to a "minimum" (i.e., zero derivative) in the de-oxy absorbance signal.

Examples of the disclosure can include at least one light emitter (e.g., light emitter 206 illustrated in FIG. 2A, light emitter 306 illustrated in FIG. 3A) configured to emit within wavelength range 764 (i.e., 495-570 nm). Examples of the disclosure can include at least one light emitter (e.g., light emitter 308 illustrated in FIG. 3A) configured to emit within wavelength range 765 (i.e., 570-750 nm). Examples of the disclosure can include at least two light emitters (e.g., light emitter 306 and light emitter 308 illustrated in FIG. 3A) configured to emit within the same wavelength range (e.g., wavelength range 764, wavelength range 765, and/or wavelength range 767). Examples of the disclosure can include at least one light emitter (e.g. light emitter 308 illustrated in FIG. 3A) configured to emit within wavelength ranges 966 and 967 (i.e., 750-1400 nm).

Examples of the disclosure can include a system capable of emitting light across a spectrum of wavelengths or a plurality of wavelength (e.g., greater than two wavelengths). For example, the system can include at least one light emitter (e.g., light emitter 606 illustrated in FIG. 6A) configured to emit light within wavelength range 964 (i.e., 495-570 nm), at least one light emitter (e.g., light emitter 605 illustrated in FIG. 6A) configured to emit light within wavelength range 966 and wavelength range 967 (i.e., 750-1400 nm), and at least one light emitter (e.g., light emitter 608 illustrated in FIG. 6A) configured to emit light within wavelength range 965 (i.e., 570-750 nm). In some examples, one light emitter can be configured to emit at 525 nm, one light emitter can be configured to emit at 660 nm, and one light emitter can be configured to emit at 890 nm. Measuring reflected light within wavelength range 965 can lead to signals with little-to-no pulsatile blood information. Measuring reflected light within wavelength range 966 and wavelength range 967 can lead to light that can be invisible to the user's eye. Examples of the disclosure can include a system configured with a common (i.e., shared) light emitter capable of emitting light to a plurality of light sensors, where at least one set of light emitter-light sensor can be configured for measuring pulsatile blood flow and at least one set of (the same) light emitter-light sensor can be configured for measuring non-pulsatile blood flow.

In some examples, at least two sets of light emitter-light sensor can be configured to measure (e.g., light passes through) the same volume of the user's skin. By measuring the same volume of skin, the non-pulsatile blood information can be accurately associated with the corresponding pulsatile blood information. In some examples, at least two light emitters and optically coupled one or more detectors can be located along the same optical axis.

In some examples, at least two sets of light emitter-light sensor can be configured to measure different volumes of the user's skin. The locations of optical components in such a configuration may be limited due to the size of a package or the separation distance between optical components, for example.

Figure 9B:
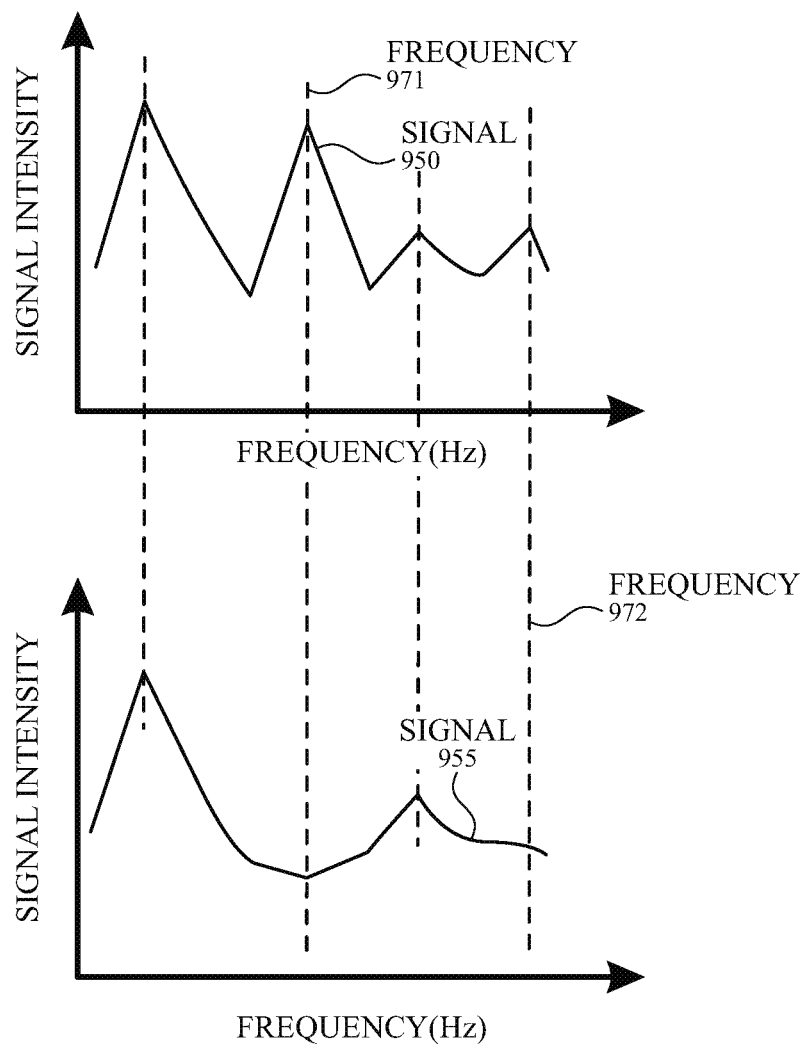
FIG. 9B illustrates exemplary signals measured at the plurality of light sensors included in an exemplary electronic device according to examples of the disclosure.

FIG. 9B illustrates exemplary signals measured at the plurality of light sensors included in an exemplary electronic device according to examples of the disclosure. Signal 950 can include pulsatile blood information and noise artifacts. Signal 955 can include noise artifacts using any of the above disclosed examples. In some examples, signal 950 can be the signal generated by one of the sets of light emitter-light sensor. In some examples, signal 955 can be the signal generated by another one of the sets of light emitter-light sensor. The PPG system can include a controller configured to determine a user's physiological signal by removing noise artifacts from signal 950. In some examples, at least a portion of the noise artifacts included in signal 950 can be determined using signal 955. For example, frequency 971 can correspond to a fundamental frequency for the user's physiological signal (e.g., PPG), and frequency 972 can correspond to a harmonic frequency for the user's physiological signal. The controller can be configured to determine the fundamental and harmonic frequencies and can utilize signal 950 and signal 955 to determine the user's physiological signal.

In some examples, signals associated with one or more light emitters (e.g., light emitter 306 and light emitter 316) can be used for determining the user's physiological signals while the user is in motion. In some examples, signals associated with one or more light emitters (e.g., light emitter 306 and light emitter 316) can be used for determining the user's physiological signals while the user is stationary. In some examples, one or more signals can include heart rate PPG signals. In some examples, one or more signals can be used for off-wrist detection (i.e., the device is located a far distance away from the user). In some examples, the device can include an accelerometer to detect the user's acceleration, and such acceleration information can additionally be used for canceling/correcting motion artifacts in the user's physiological signal. In some examples, one or more of the light emitters and/or light sensors can be disabled, powered off, or their signals can be ignored. For example, light emitter 308 and/or light emitter 316 (illustrated in FIG. 3A) can be powered off when the user is moving.

Figure 10A:
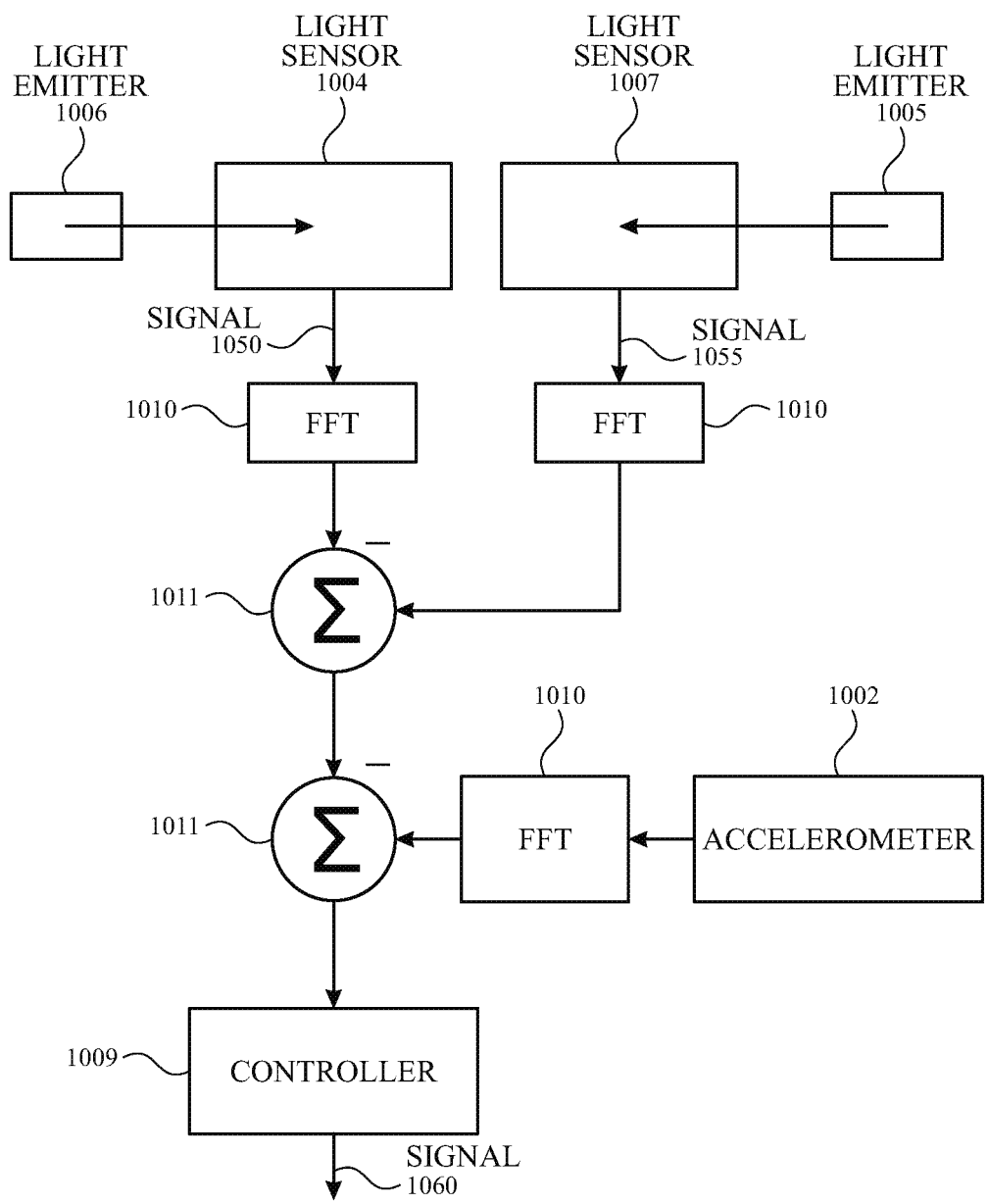
FIG. 10A illustrates an exemplary circuit diagram for motion artifact removal according to examples of the disclosure.
Figure 10B:
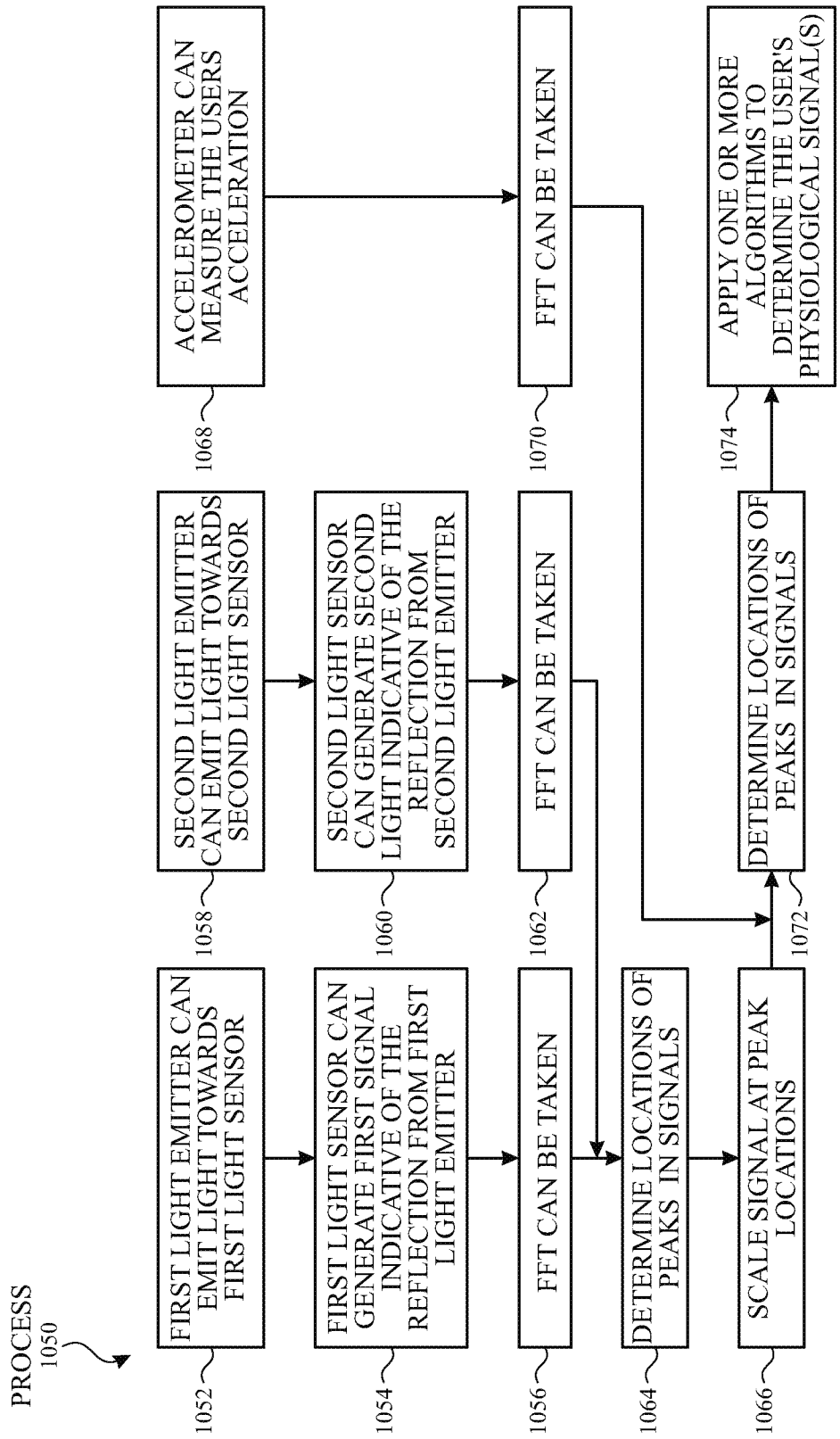
FIG. 10B illustrates an exemplary process for motion artifact removal according to examples of the disclosure.

FIG. 10A illustrates an exemplary circuit diagram and FIG. 10B illustrates an exemplary process for motion artifact removal according to examples of the disclosure. The system can include light emitter 1006 optically coupled to light sensor 1004 and light emitter 1005 optically coupled to light sensor 1007. Light emitter 1006 can emit light towards light sensor 1004 (step 1052 of process 1050). Light sensor 1004 can detect the reflected light from light emitted by light emitter 1006 and can generate a signal 1050 (step 1054 of process 1050). The Fourier transform of signal 1050 can be taken using FFT 1010 (step 1056 of process 1050). Light emitter 1005 can emit light towards light sensor 1007 (step 1058 of process 1050). Light sensor 1007 can detect the reflected light from light emitted by light emitter 1005 and can generate a signal 1055 (step 1060 of process 1050). In some examples, light emitter 1005 can emit light at the same time as light emitter 1006. The Fourier transfer of signal 1055 can be taken using FFT 1010 (step 1062 of process 1050). The locations of the peaks (i.e., "maximum"/zero derivative) in signal 1050 and signal 1055 can be determined using component 1011 (step 1064 of process 1050). In some examples, the values of signal 1050 can be scaled (e.g., a Gaussian weight can be applied) at locations where a peak exists (step 1066 of process 1050). In some examples, the corrected (or adjusted) signal 1050 can include peaks from the fundamental and harmonic frequencies of the user's physiological signal.

The system can further include an accelerometer 1002. Accelerometer 1002 can measure the user's acceleration (step 1068 of process 1050). In some examples, the acceleration measurement can be concurrent with the optical measurements from the light sensors. The Fourier transform of the acceleration signal can be taken using FFT 1010 (step 1070 of process 1050). The locations of the peaks in the corrected signal 1050 and acceleration signal can be determined using component 1011 (step 1072 of process 1050). Controller 1009 can apply one or more algorithms and/or simple mathematical functions to determine the user's physiological signal 1060 (step 1074 of process 1050).

Figure 11A:
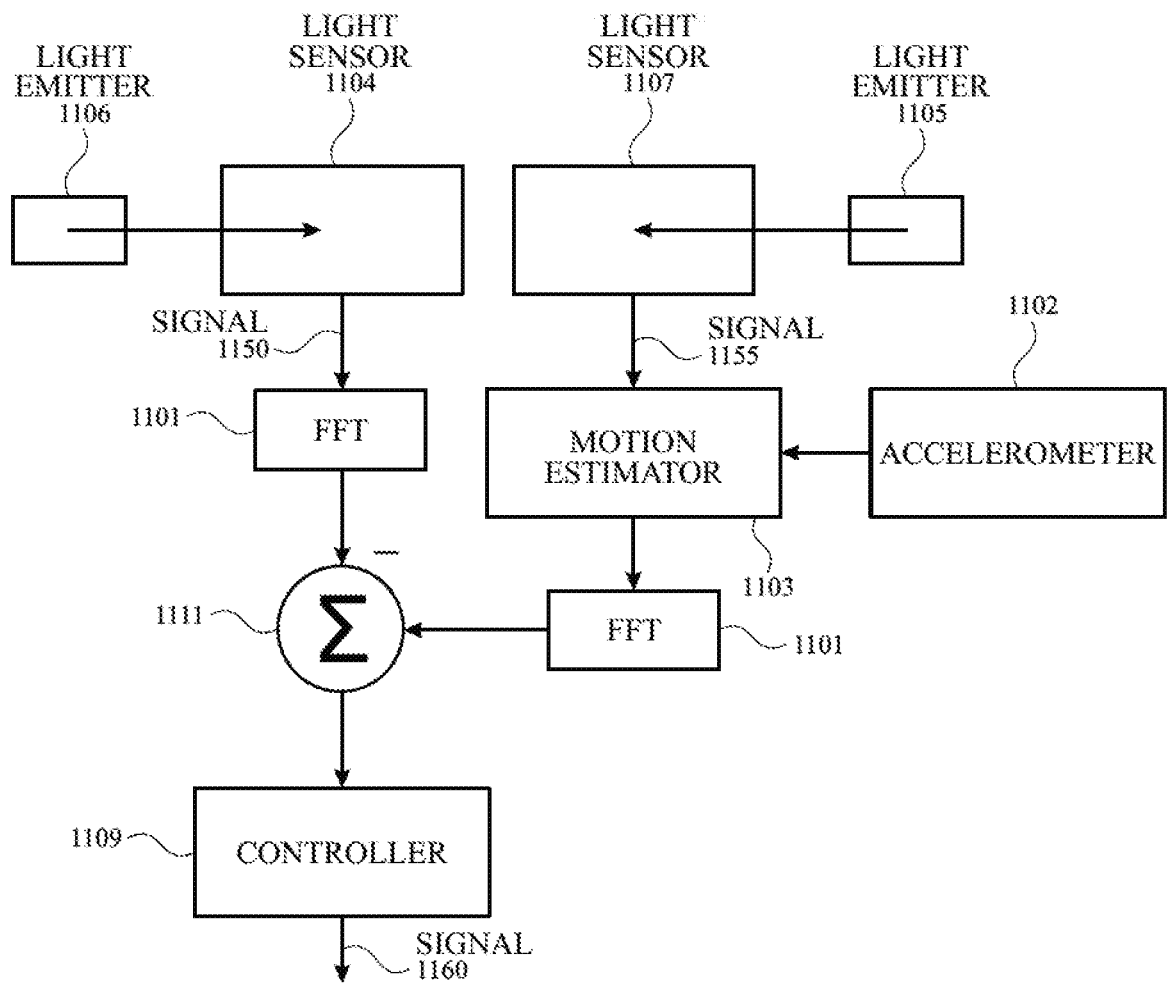
FIG. 11A illustrates an exemplary circuit diagram for motion artifact removal according to examples of the disclosure.
Figure 11B:
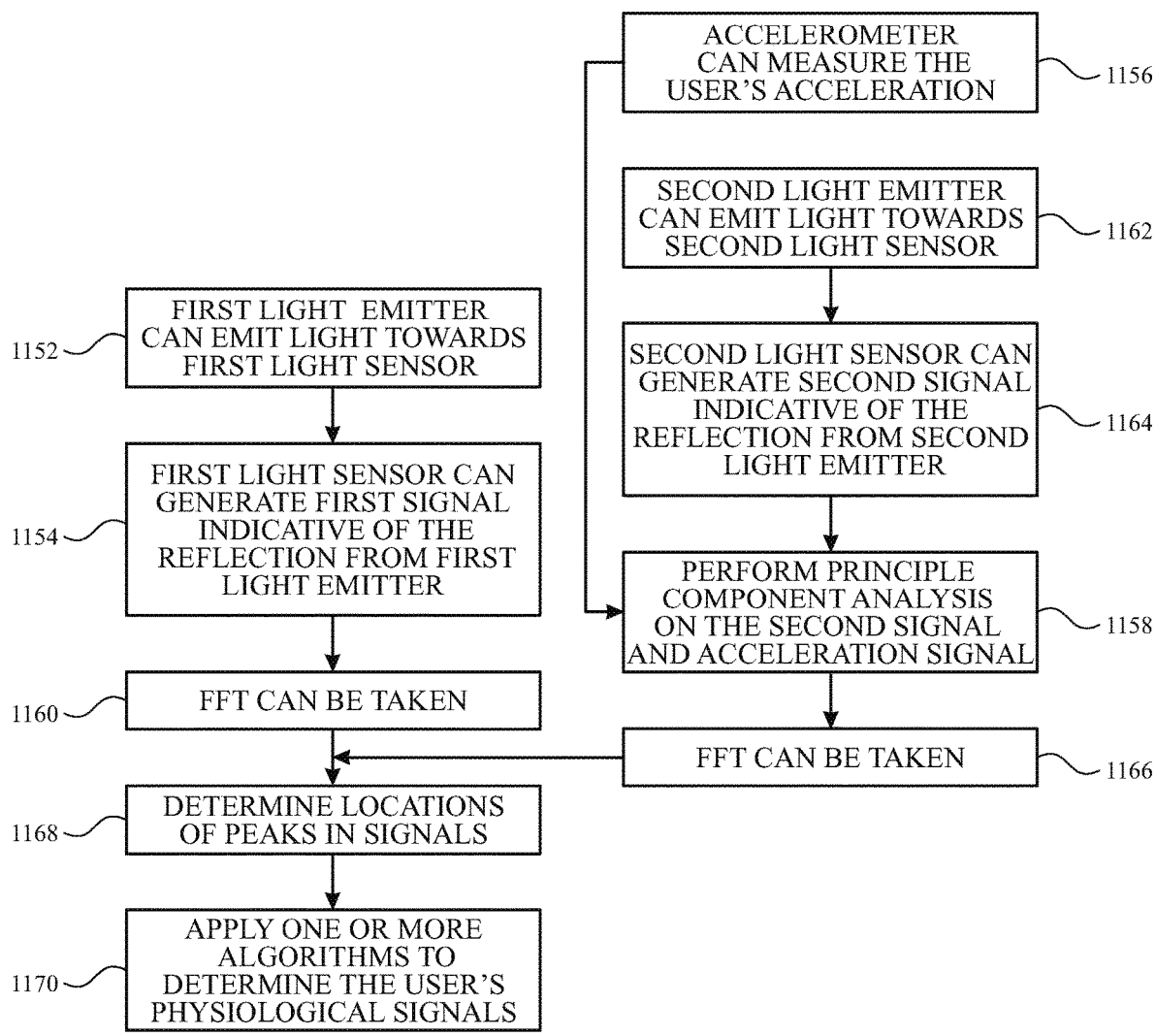
FIG. 11B illustrates an exemplary process for motion artifact removal according to examples of the disclosure.

FIG. 11A illustrates an exemplary circuit diagram and FIG. 11B illustrates an exemplary process for motion artifact removal according to examples of the disclosure. The system can include light emitter 1106 optically coupled to light sensor 1104 and light emitter 1105 optically coupled to light sensor 1107. Light emitter 1106 can emit light towards light sensor 1104 (step 1152 of process 1150). Light sensor 1104 can detect the reflected light from light emitted by light emitter 1106 and can generate a signal 1150 (step 1154 of process 1150). The Fourier transform of signal 1150 can be taken (step 1160 of process 1150).

Light emitter 1105 can emit light towards light sensor 1107 (step 1162 of process 1150). Light sensor 1107 can detect the reflected light from light emitted by light emitter 1105 and can generate a signal 1155 (step 1164 of process 1150). The system can further include an accelerometer 1102. Accelerometer 1102 can measure the user's acceleration (step 1156 of process 1150). In some examples, the acceleration measurement can be concurrent with the optical measurements from the light sensors. Principle component analysis (PCA) can be performed on signal 1155 and the acceleration signal using motion estimator 1103 (step 1158 or process 1150). PCA 1102 can be configured to utilize an orthogonal transformation to convert signal 1155 and the acceleration signal into three orthogonal components. The Fourier transform of the orthogonal components can be taken using FFT 1110 (step 1166 of process 1150).

The locations of the peaks in the signals from both FFTs 1110 can be determined using component 1111 (step 1168 of process 1150). In some examples, one or more gait frequencies in signal 1150 can be determined. At the one or more gait frequencies, the signals can be attenuated. The controller 1009 can be configured to apply one or more algorithms and/or simple mathematical functions to determine the user's physiological signal 1160 (step 1170 of process 1150).

Figure 12A:
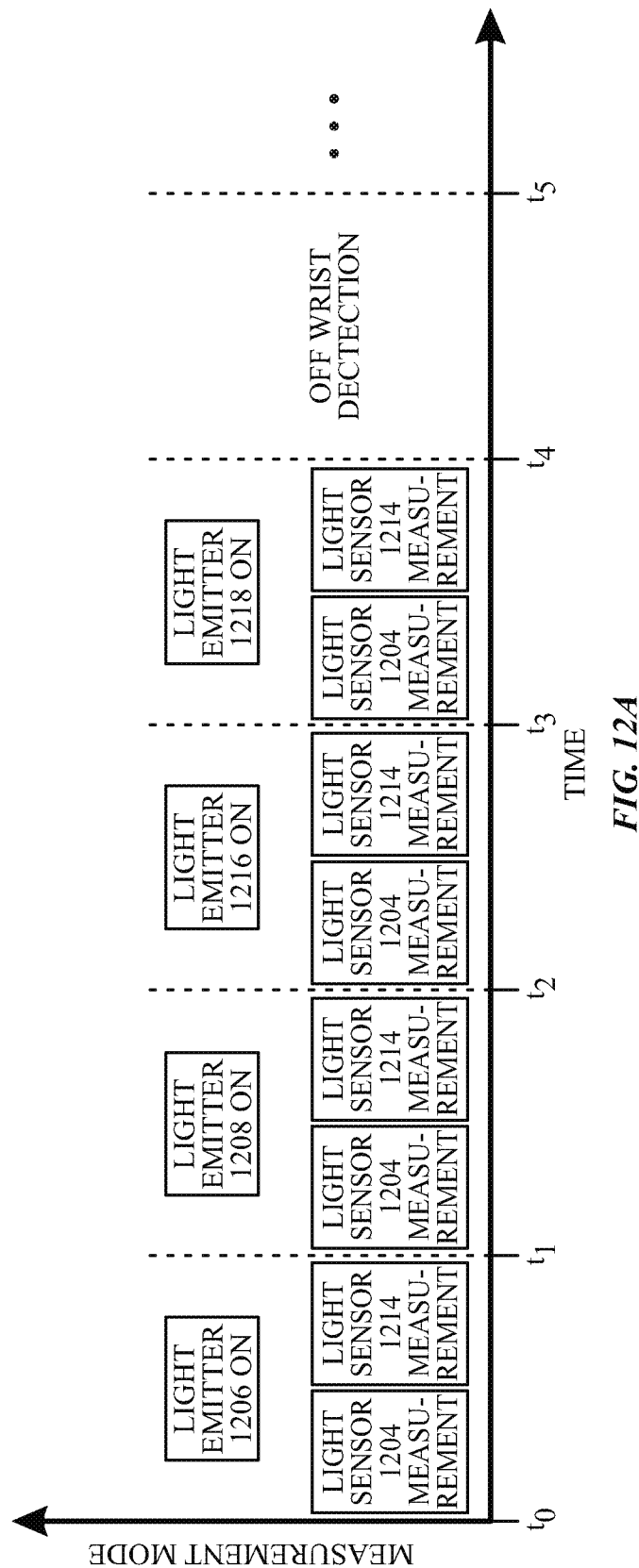
FIGS. 12A-12C illustrate exemplary measurement modes according to examples of the disclosure.
Figure 12B:
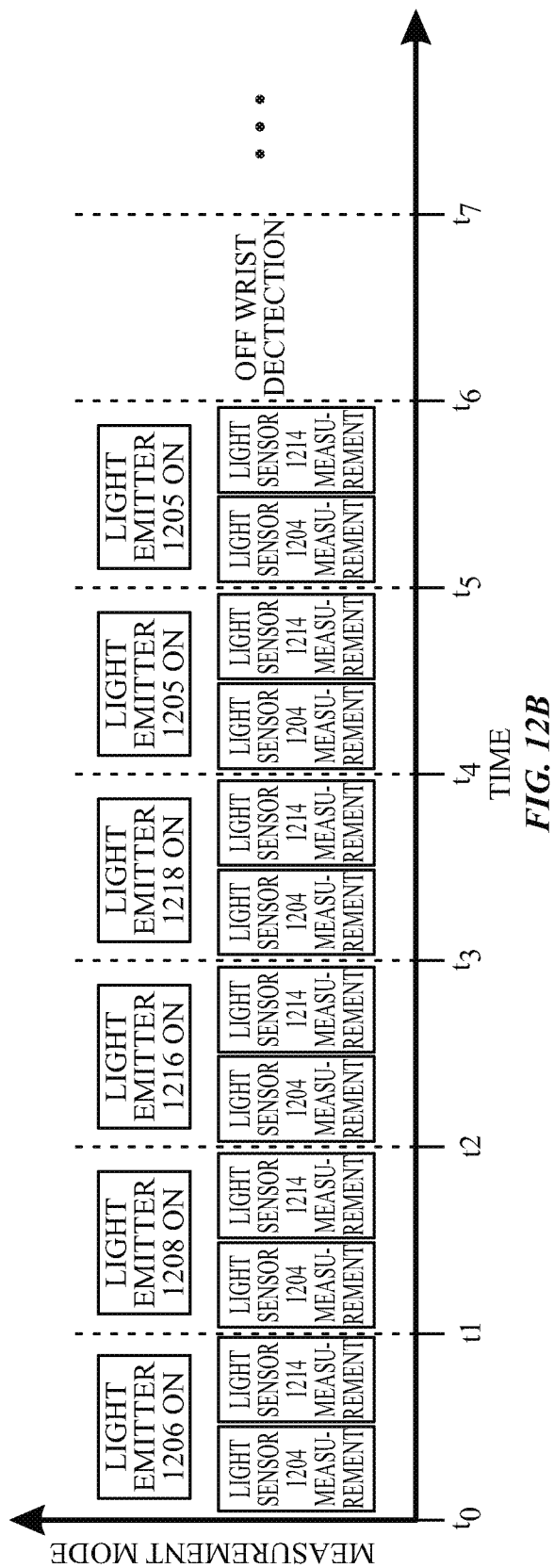
Figure 12C:
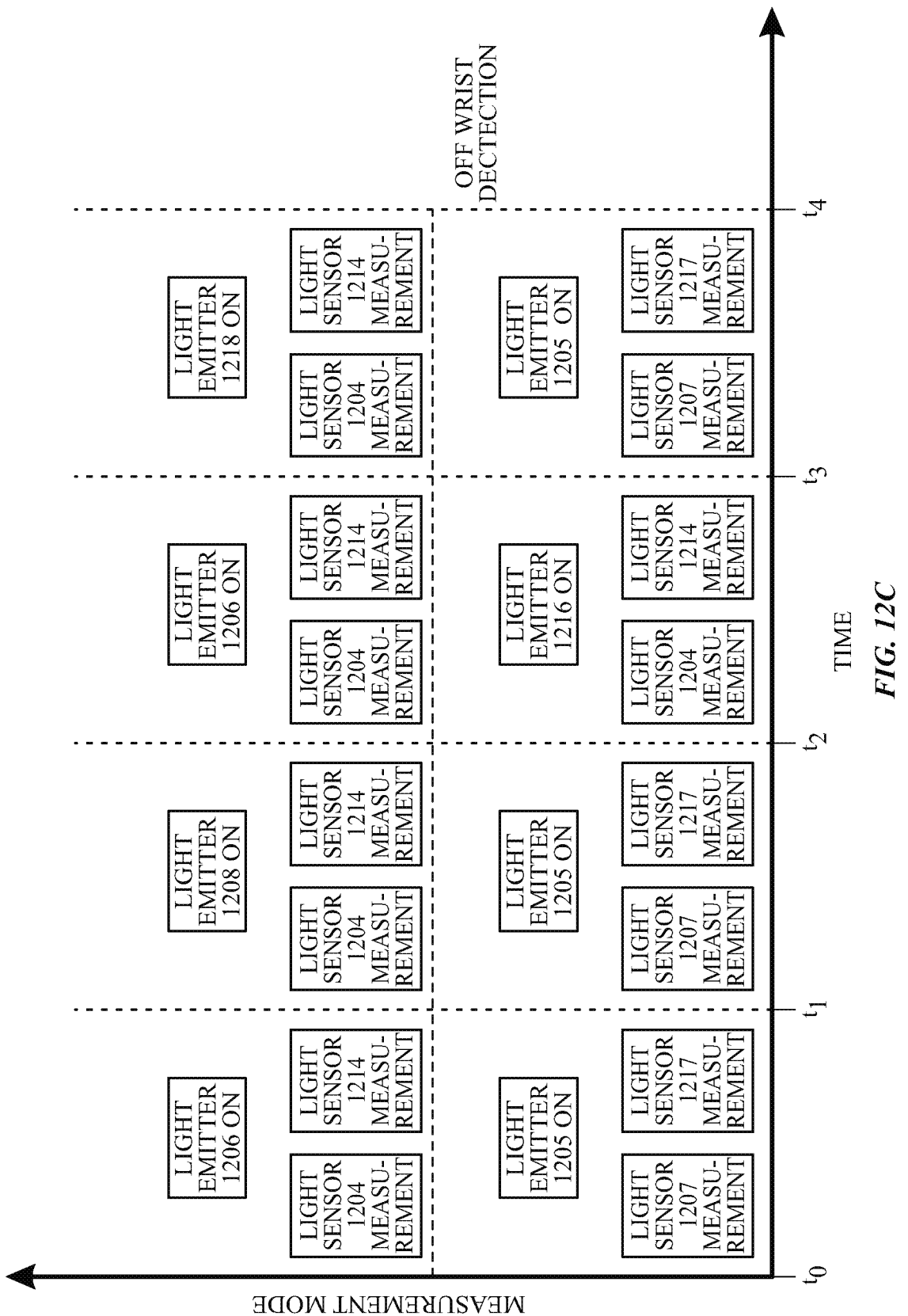

In the one or more of the above disclosed systems, the sets of light emitter-light sensor can be operated serially or in parallel (i.e., concurrently). FIGS. 12A-12C illustrate exemplary measurement modes according to examples of the disclosure. The PPG system can include light emitter 1206, light emitter 1208, light emitter 1216, light emitter 1218, light sensor 1204, and light sensor 1214.

As illustrated in FIG. 12A, the system can be configured to cycle through the sets. Between time $t_0$ and $t_1$, light emitter 1206 can be active/on. Light sensor 1204 can measure the reflected light from light emitter 1206 followed by light sensor 1214 measuring the reflected light from light emitter 1206. Between time $t_1$ and time $t_2$, light emitter 1208 can be active/on. Light sensor 1204 can measure the reflected light from light emitter 1208, followed by light sensor 1214 measuring the reflected light from light emitter 1208. Between time $t_2$ and time $t_3$, light emitter 1216 can be active/on. Light sensor 1204 can measure the reflected light from light emitter 1216, followed by light sensor 1214 measuring the reflected light from light emitter 1216. Between time $t_3$ and time $t_4$, light emitter 1218 can be active/on. Light sensor 1204 can measure the reflected light from light emitter 1218, followed by light sensor 1214 measuring the reflected light from light emitter 1218. Between time $t_4$ and time $t_5$, the system can be configured for off-wrist detection. In some examples, the cycle can be repeated. In some examples, subsequent cycles can have a different order.

The system can further include light emitter 1205 and light emitter 1215. As illustrated in FIG. 12B, the measurements can include operation of those additional light emitters in time periods following the operation of all other light emitters. Between time $t_4$ and time $t_5$, light emitter 1205 can be active/on. Light sensor 1204 can measure the reflected light from light emitter 1205, followed by light sensor 1214 measuring the reflected light from light emitter 1205. Between time $t_5$ and time $t_6$, light emitter 1215 can be active/on. Light sensor 1204 can measure the reflected light from light emitter 1215, followed by light sensor 1214 measuring the reflected light from light emitter 1215. Between time $t_6$ and time $t_7$, the system can be configured for off-wrist detection. In some examples, the cycle can be repeated. In some examples, subsequent cycles can have a different order.

In some examples, two or more measurements can operate concurrently. As illustrated in FIG. 12C, a first measurement and a second measurement can operate concurrently between time $t_0$ and $t_1$. The first measurement can include light emitter 1206 active/on, while light sensor 1204 measures the reflected light and light sensor 1214 measures the reflected light. The second measurement can include light emitter 1205 active/on, while light sensor 1207 measures the reflected light and light sensor 1217 measures the reflected light. In some examples, the measurements can operate in a staggered (i.e., the start of one measurement can be delayed from the start of another measurement). In some examples, a time period can include the first measurement having a different set of light emitter-light sensor (e.g., light emitter 1208, light sensor 1204, and light sensor 1214), while the second measurement can be the same (e.g., light emitter 1205, light sensor 1207, and light sensor 1217), as illustrated between time $t_1$ and $t_2$. In some examples, a time period can include the first measurement having the same set of light emitter-light sensor (e.g., light emitter 1206, light sensor 1204, and light sensor 1214), as illustrated between time $t_2$ and $t_3$. In some examples, a time period can include more than two measurements operating concurrently. For example, all the measurements can be taken at the same time (not shown). In some examples, off-wrist detection can occur at any time between measurements or concurrently with measurements.

Figure 13A:
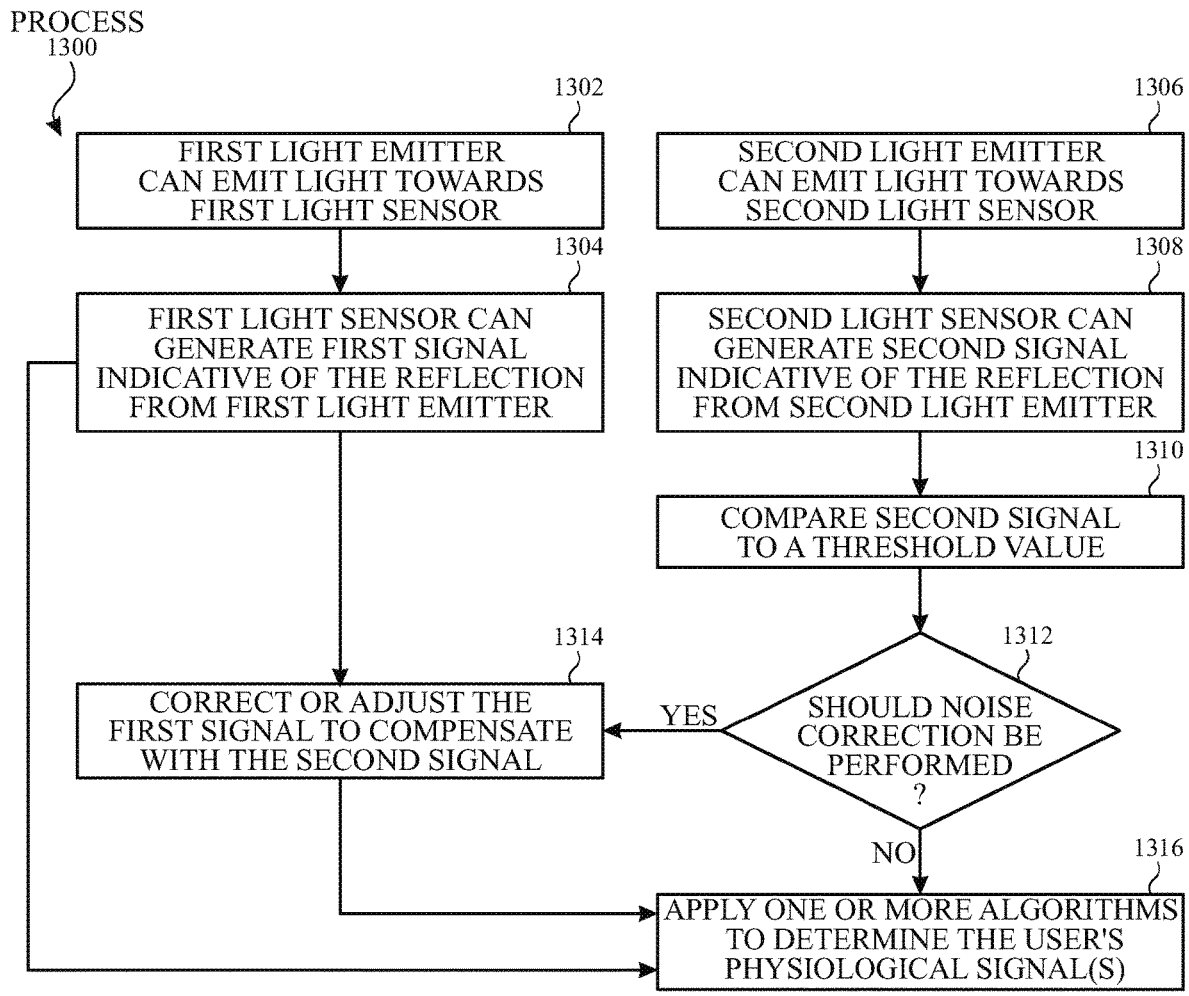
FIG. 13A illustrates an exemplary process illustrating time-based operation of a PPG system according to examples of the disclosure.

FIG. 13A illustrates an exemplary process illustrating time-based operation of a PPG system according to examples of the disclosure. The first light emitter can emit light towards the first light sensor (step 1302 of process 1300). The first light sensor can generate the first signal indicative of the reflection from the first light emitter (step 1304 of process 1300). The second light emitter can emit light towards the second light sensor (step 1306 of process 1300). The second light sensor can generate a second signal indicative of the reflection from the second light emitter (step 1308 of process 1300). In some examples, first light emitter can operate concurrently with the second light emitter. In some examples, first light emitter can operate before second light emitter. In some examples, second light emitter can operate before first light emitter. The second signal can be compared to a threshold value (step 1310 of process 1300), and a controller can determine whether noise correction should be performed (step 1312 of process 1300). If noise correction is to be performed, the first signal can be corrected or adjusted with the second signal (step 1314 of process 1300). One or more algorithms can be applied to determine the user's physiological signal(s) (step 1316 of process 1300).

Figure 13B:
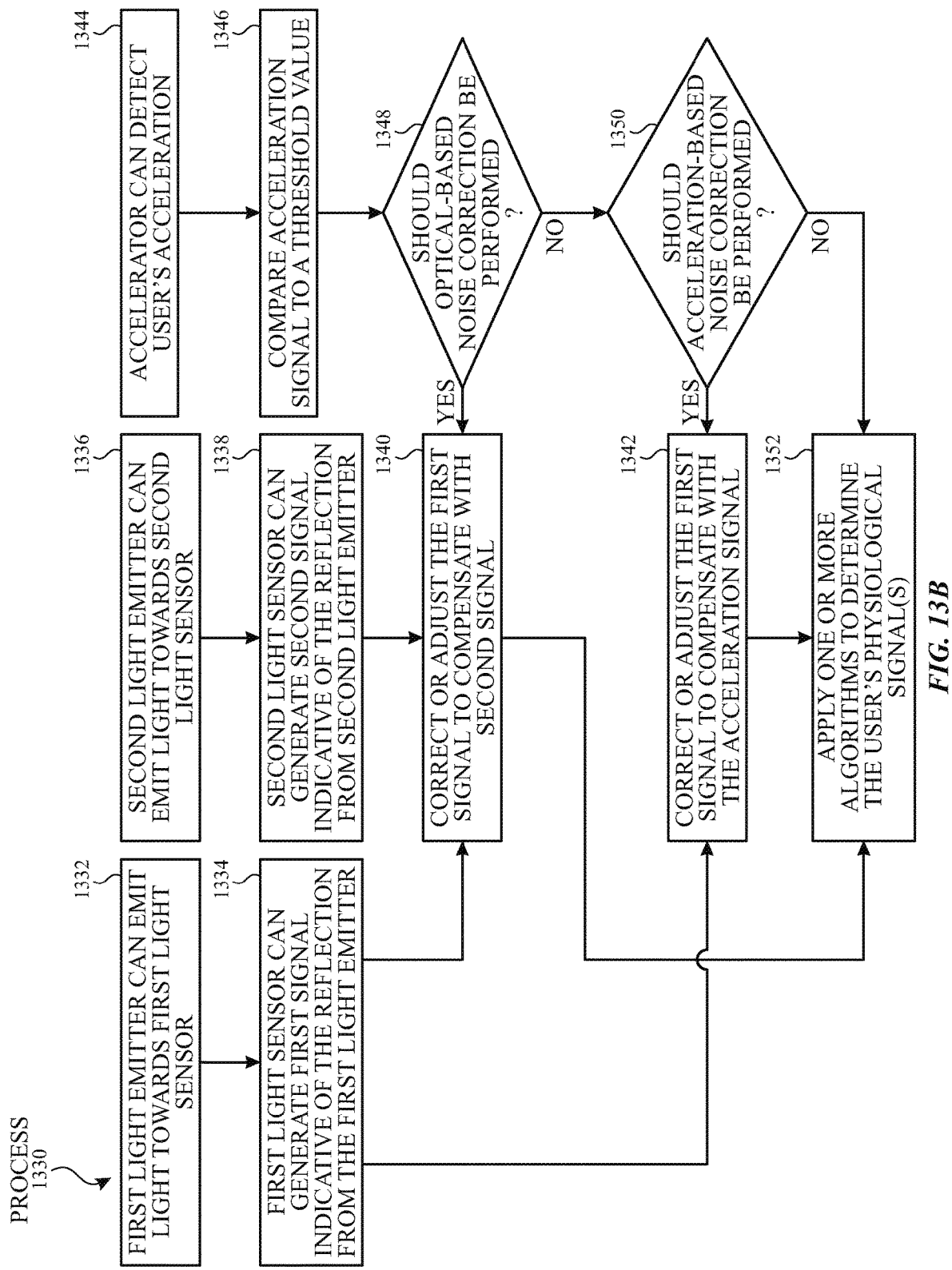
FIG. 13B illustrates an exemplary process illustrating operation of a PPG system including a light emitter-light sensor set for motion detection according to examples of the disclosure.

FIG. 13B illustrates an exemplary process illustrating operation of a PPG system including a light emitter-light sensor set for motion detection according to examples of the disclosure. The first light emitter can emit light towards the first light sensor (step 1332 of process 1330). The first light sensor can generate the first signal indicative of the reflection from the first light emitter (step 1334 of process 1330). The second light emitter can emit light towards the second light sensor (step 1336 of process 1330). The second light sensor can generate the second signal indicative of the reflection from the second light emitter (step 1338 of process 1330). An accelerometer can detect the user's acceleration and generate an acceleration signal (step 1344 of process 1330). The acceleration signal can be compared to a threshold value (step 1346 of process 1330). A controller can determine whether optical-based noise correction should be performed (step 1348 of process 1330), and if so, the first signal can be corrected or adjusted with the second signal (step 1340 of process 1330). If not, the controller can determine whether acceleration-based noise correction should be performed (step 1350 of process 1330). If so, the first signal can be corrected or adjusted with the acceleration signal (step 1342 of process 1330). One or more algorithms can be applied to determine the user's physiological signal (s) (step 1352 of process 1330).

Figure 13C:
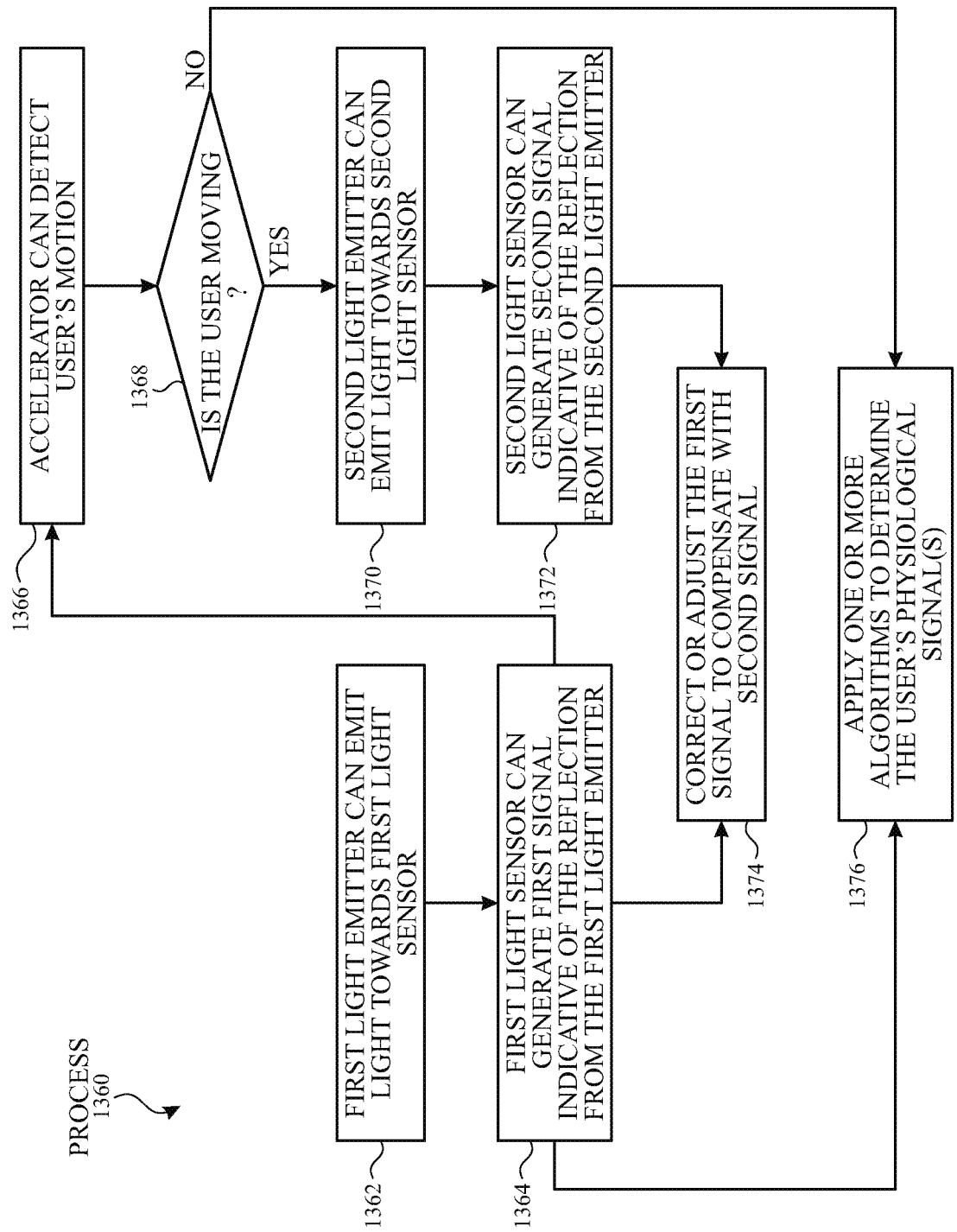
FIG. 13C illustrates an exemplary process illustrating operation of a PPG system including an accelerometer for motion detection according to examples of the disclosure.

FIG. 13C illustrates an exemplary process illustrating operation of a PPG system including an accelerometer for motion detection according to examples of the disclosure. The first light emitter can emit light towards first light sensor (step 1362 of process 1360). The first light sensor can generate the first signal indicative of the reflection from the first light emitter (step 1364 of process 1360). An accelerator can detect the user's motion and generate an acceleration signal (step 1366 of process 1360). A controller can determine whether the user is moving (step 1368 of process 1360). If the user is moving, the second light emitter can emit light towards second light sensor (step 1370 of process 1360). The second light sensor can detect the reflected light and generate a second signal (step 1372 of process 1330). In some examples, the second light sensor can remain in an inactive state until the accelerometer detects user movement. The first signal can be corrected or adjusted using the second signal (step 1374 of process 1330). A controller can apply one or more algorithms to determine the user's physiological signal(s) (step 1376 of process 1330).

Figure 13D:
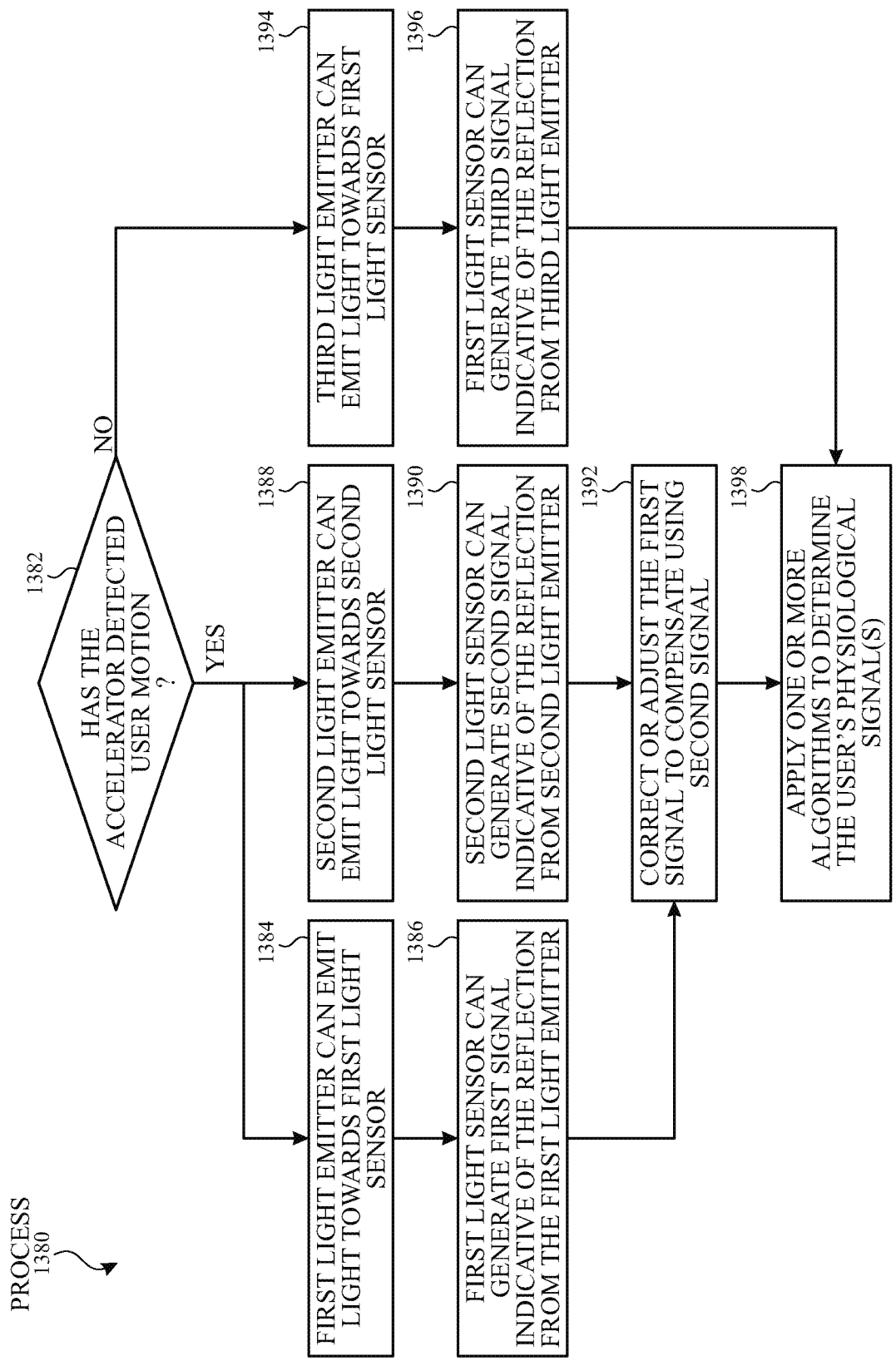
FIG. 13D illustrates an exemplary process illustrating operation of a PPG system according to examples of the disclosure.

FIG. 13D illustrates an exemplary process illustrating operation of a PPG system according to examples of the disclosure. An accelerometer can detect user motion (step 1382 of process 1380). If user motion is detected, a first light emitter can emit light towards a first light sensor (step 1384 of process 1380). The first light sensor can generate a first signal indicative of the reflection from the first light emitter (step 1386 of process 1380). A second light emitter can emit light towards a second light sensor (step 1388 of process 1380). The second light sensor can generate a second signal indicative of the reflection from the second light emitter (step 1390 of process 1380). The first signal can be corrected or adjusted using the second signal (step 1392 of process 1380). If user motion has not been detected, a third light emitter can emit light towards the first light sensor (step 1394 of process 1380). The first light sensor can generate a third signal indicative of the reflection from the third light emitter (step 1396 of process 1380). A controller can apply one or more algorithms to determine the user's physiological signal(s) (step 1398 of process 1380).

Figure 14:
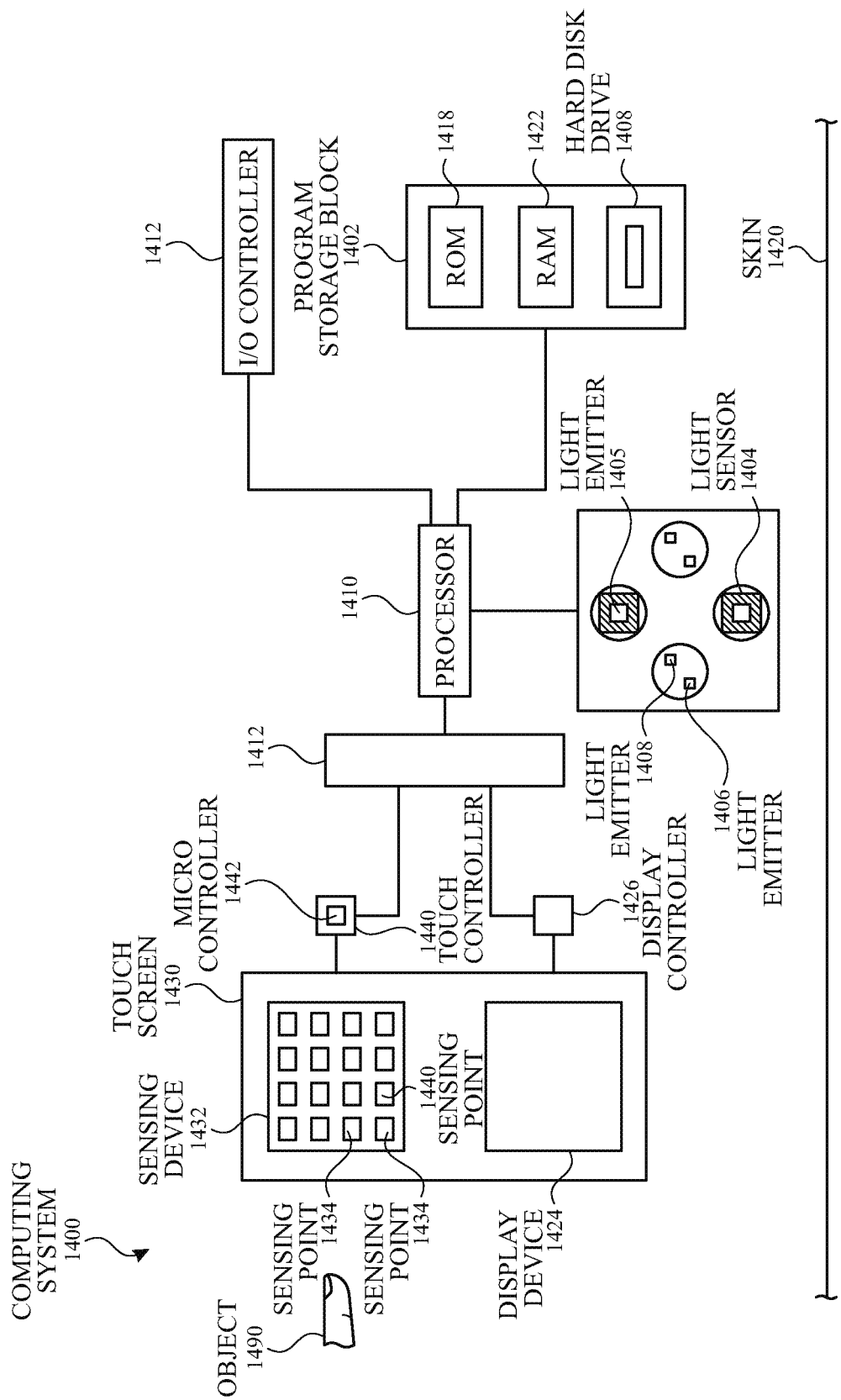
FIG. 14 illustrates an exemplary block diagram of a computing system comprising light emitters and light sensors for measuring a signal associated with a user's physiological state according to examples of the disclosure.

FIG. 14 illustrates an exemplary block diagram of a computing system comprising light emitters and light sensors for measuring a signal associated with a user's physiological state according to examples of the disclosure. Computing system 1400 can correspond to any of the computing devices illustrated in FIGS. 1A-1C. Computing system 1400 can include a processor 1410 configured to execute instructions and to carry out operations associated with computing system 1400. For example, using instructions retrieved from memory, processor 1410 can control the reception and manipulation of input and output data between components of computing system 1400. Processor 1410 can be a single-chip processor or can be implemented with multiple components.

In some examples, processor 1410 together with an operating system can operate to execute computer code and produce and use data. The computer code and data can reside within a program storage block 1402 that can be operatively coupled to processor 1410. Program storage block 1402 can generally provide a place to hold data that is being used by computing system 1400. Program storage block 1402 can be any non-transitory computer-readable storage medium, and can store, for example, history and/or pattern data relating to PPG signal and perfusion index values measured by one or more light sensors such as light sensors 1404. By way of example, program storage block 1402 can include Read-Only Memory (ROM) 1418, Random-Access Memory (RAM) 1422, hard disk drive 1408 and/or the like. The computer code and data could also reside on a removable storage medium and loaded or installed onto the computing system 1400 when needed. Removable storage mediums include, for example, CD-ROM, DVD-ROM, Universal Serial Bus (USB), Secure Digital (SD), Compact Flash (CF), Memory Stick, Multi-Media Card (MMC) and a network component.

Computing system 1400 can also include an input/output (I/O) controller 1412 that can be operatively coupled to processor 1410, or it can be a separate component as shown. I/O controller 1412 can be configured to control interactions with one or more I/O devices. I/O controller 1412 can operate by exchanging data between processor 1410 and the I/O devices that desire to communicate with processor 1410.

The I/O devices and I/O controller 1412 can communicate through a data link. The data link can be a one-way link or a two-way link. In some cases, I/O devices can be connected to I/O controller 1412 through wireless connections. By way of example, a data link can correspond to PS/2, USB, Firewire, IR, RF, Bluetooth or the like.

Computing system 1400 can include a display device 1424 that can be operatively coupled to processor 1410. Display device 1424 can be a separate component (peripheral device) or can be integrated with processor 1410 and program storage block 1402 to form a desktop computer (e.g., all-in-one machine), a laptop, handheld or tablet computing device of the like. Display device 1424 can be configured to display a graphical user interface (GUI) including perhaps a pointer or cursor as well as other information to the user. By way of example, display device 1424 can be any type of display including a liquid crystal display (LCD), an electroluminescent display (ELD), a field emission display (FED), a light emitting diode display (LED), an organic light emitting diode display (OLED) or the like.

Display device 1424 can be coupled to display controller 1426 that can be coupled to processor 1410. Processor 1410 can send raw data to display controller 1426, and display controller 1426 can send signals to display device 1424. Data can include voltage levels for a plurality of pixels in display device 1424 to project an image. In some examples, processor 1410 can be configured to process the raw data.

Computing system 1400 can also include a touch screen 1430 that can be operatively coupled to processor 1410. Touch screen 1430 can be a combination of sensing device 1432 and display device 1424, where the sensing device 1432 can be a transparent panel that is positioned in front of display device 1424 or integrated with display device 1424. In some cases, touch screen 1430 can recognize touches and the position and magnitude of touches on its surface. Touch screen 1430 can report the touches to processor 1410, and processor 1410 can interpret the touches in accordance with its programming. For example, processor 1410 can perform tap and event gesture parsing and can initiate a wake of the device or powering on one or more components in accordance with a particular touch.

Touch screen 1430 can be coupled to a touch controller 1440 that can acquire data from touch screen 1430 and can supply the acquired data to processor 1410. In some cases, touch controller 1440 can be configured to send raw data to processor 1410, and processor 1410 can process the raw data. For example, processor 1410 can receive data from touch controller 1440 and can determine how to interpret the data. The data can include the coordinates of a touch as well as pressure exerted. In some examples, touch controller 1440 can be configured to process raw data itself. That is, touch controller 1440 can read signals from sensing points 1434 located on sensing device 1432 and can turn the signals into data that the processor 1410 can understand.

Touch controller 1440 can include one or more microcontrollers such as microcontroller 1442, each of which can monitor one or more sensing points 1434. Microcontroller 1442 can, for example, correspond to an application specific integrated circuit (ASIC), which works with firmware to monitor the signals from sensing device 1432, process the monitored signals, and report this information to processor 1410.

One or both display controller 1426 and touch controller 1440 can perform filtering and/or conversion processes. Filtering processes can be implemented to reduce a busy data stream to prevent processor 1410 from being overloaded with redundant or non-essential data. The conversion processes can be implemented to adjust the raw data before sending or reporting them to processor 1410.

In some examples, sensing device 1432 can be based on capacitance. When two electrically conductive members come close to one another without actually touching, their electric fields can interact to form a capacitance. The first electrically conductive member can be one or more of the sensing points 1434, and the second electrically conductive member can be an object 1490 such as a finger. As object 1490 approaches the surface of touch screen 1430, a capacitance can form between object 1490 and one or more sensing points 1434 in close proximity to object 1490. By detecting changes in capacitance at each of the sensing points 1434 and noting the position of sensing points 1434, touch controller 1440 can recognize multiple objects, and determine the location, pressure, direction, speed and acceleration of object 1490 as it moves across the touch screen 1430. For example, touch controller 1440 can determine whether the sensed touch is a finger, tap, or an object covering the surface.

Sensing device 1432 can be based on self-capacitance or mutual capacitance. In self-capacitance, each of the sensing points 1434 can be provided by an individually charged electrode. As object 1490 approaches the surface of the touch screen 1430, the object can capacitively couple to those electrodes in close proximity to object 1490, thereby stealing charge away from the electrodes. The amount of charge in each of the electrodes can be measured by the touch controller 1440 to determine the position of one or more objects when they touch or hover over the touch screen 1430. In mutual capacitance, sensing device 1432 can include a two layer grid of spatially separated lines or wires (not shown), although other configurations are possible. The upper layer can include lines in rows, while the lower layer can include lines in columns (e.g., orthogonal). Sensing points 1434 can be provided at the intersections of the rows and columns. During operation, the rows can be charged, and the charge can capacitively couple from the rows to the columns. As object 1490 approaches the surface of the touch screen 1430, object 1490 can capacitively couple to the rows in close proximity to object 1490, thereby reducing the charge coupling between the rows and columns. The amount of charge in each of the columns can be measured by touch controller 1440 to determine the position of multiple objects when they touch the touch screen 1430.

Computing system 1400 can also include one or more light emitters such as light emitters 1406 and one or more light sensors such as light sensors 1404 proximate to skin 1420 of a user. Light emitters 1406 can be configured to generate light, and light sensors 1404 can be configured to measure a light reflected or absorbed by skin 1420, vasculature, and/or blood of the user. Device 1400 can include a plurality of sets of light emitter-light sensor. At least one of the sets of light emitter-light sensor can be configured to measure pulsatile blood, and at least one of the sets of light emitter-light sensor can be configured to measure non-pulsatile blood. In some examples, device 1400 can include an accelerometer (not shown). Light sensor 1404 can send measured raw data to processor 1410, and processor 1410 can perform noise and/or artifact cancelation to determine the PPG signal and/or perfusion index. Processor 1410 can dynamically activate light emitters and/or light sensors and dynamically reconfigure the aperture properties based on an application, user skin type, and usage conditions. In some examples, some light emitters and/or light sensors can be activated, while other light emitters and/or light sensors can be deactivated to conserve power, for example. In some examples, processor 1410 can store the raw data and/or processed information in a ROM 1418 or RAM 1422 for historical tracking or for future diagnostic purposes.

Figure 15:
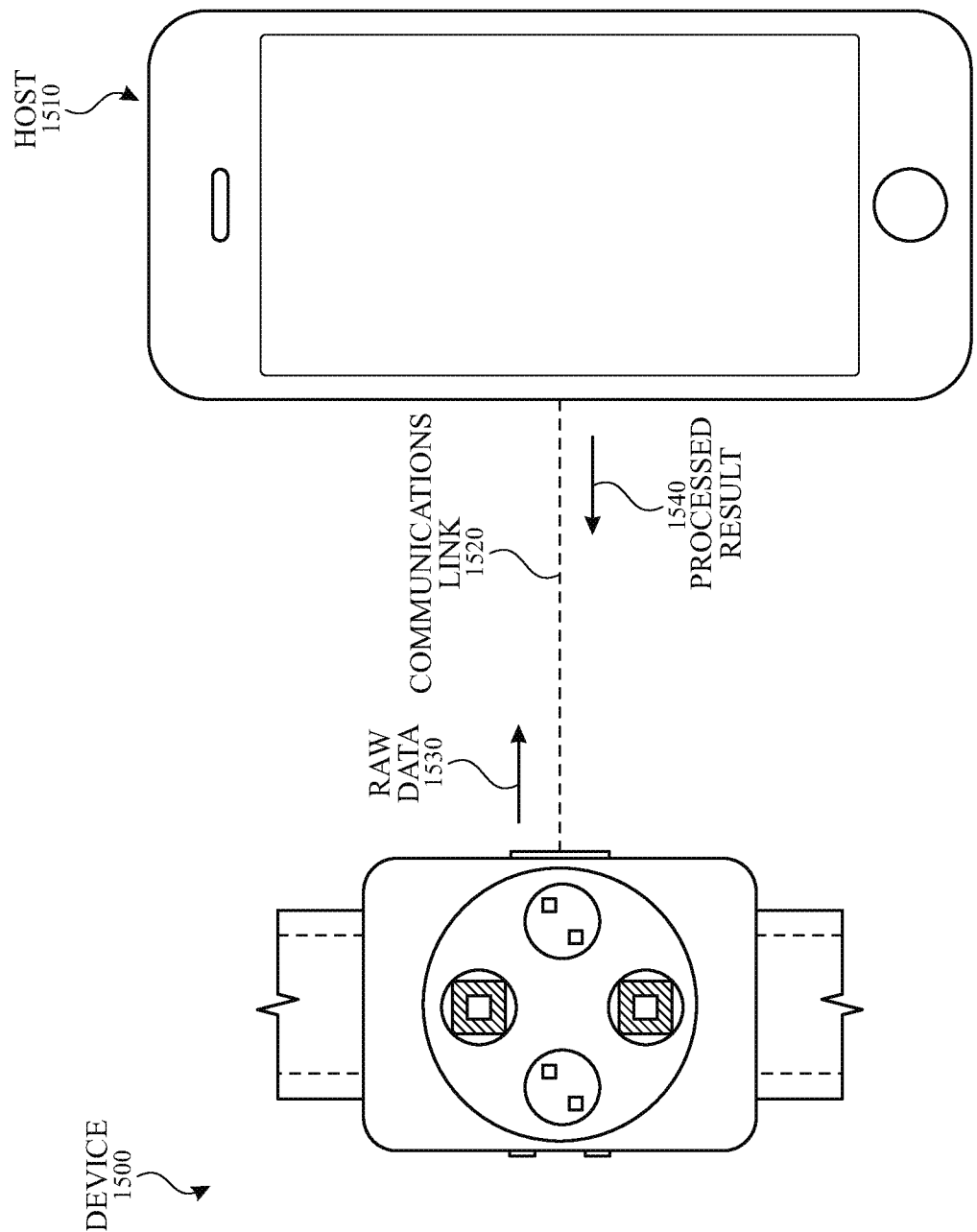
FIG. 15 illustrates an exemplary configuration in which an electronic device is connected to a host according to examples of the disclosure.

In some examples, the light sensors can measure light information and a processor can determine a PPG signal and/or perfusion index from the reflected or absorbed light. Processing of the light information can be performed on the device as well. In some examples, processing of light information need not be performed on the device itself. FIG. 15 illustrates an exemplary configuration in which an electronic device is connected to a host according to examples of the disclosure. Host 1510 can be any device external to device 1500 including, but not limited to, any of the systems illustrated in FIGS. 1A-1C or a server. Device 1500 can be connected to host 1510 through communications link 1520. Communications link 1520 can be any connection including, but not limited to, a wireless connection and a wired connection. Exemplary wireless connections include Wi-Fi, Bluetooth, Wireless Direct and Infrared. Exemplary wired connections include Universal Serial Bus (USB), FireWire, Thunderbolt, or any connection requiring a physical cable.

In operation, instead of processing light information from the light sensors on the device 1500 itself, device 1500 can send raw data 1530 measured from the light sensors over communications link 1520 to host 1510. Host 1510 can receive raw data 1530, and host 1510 can process the light information. Processing the light information can include canceling or reducing any noise due to artifacts and determining physiological signals such as a user's heart rate. Host 1510 can include algorithms or calibration procedures to account for differences in a user's characteristics affecting PPG signal and perfusion index. Additionally, host 1510 can include storage or memory for tracking a PPG signal and perfusion index history for diagnostic purposes. Host 1510 can send the processed result 1540 or related information back to device 1500. Based on the processed result 1540, device 1500 can notify the user or adjust its operation accordingly. By offloading the processing and/or storage of the light information, device 1500 can conserve space and power-enabling device 1500 to remain small and portable, as space that could otherwise be required for processing logic can be freed up on the device.

An electronic device is disclosed. The electronic device can comprise: one or more first light emitters configured to generate a first light; one or more first light sensors configured to detect a reflection of the first light and configured to generate a first signal indicative of the reflection of the first light, the first signal including non-pulsatile blood information; and logic coupled to the one or more first light sensors, the logic configured to: receive the first signal, and determine at least a portion of a physiological signal from the first signal. Additionally or alternatively, in some examples, the device can further comprise: one or more second light sensors configured to detect a reflection of a second light and configured to generate a second signal indicative of the reflection of the second light, the second light generated by the one or more first light emitters and the second signal including pulsatile blood information, wherein the logic is further coupled to the one or more second light sensors, and further configured to receive the second signal and include the second signal in the determination of the physiological signal. Additionally or alternatively, in some examples, the one or more first light emitters, one or more first light sensors, and one or more second light sensors are located along a common optical axis. Additionally or alternatively, in some examples, the device further comprises: one or more second light emitters configured to generate a second light, wherein the one or more first light sensors are further configured to generate a second signal indicative of the reflection of the second light, the second signal including pulsatile blood information, wherein the logic is further configured to receive the second signal and include the second signal in the determination of the physiological signal. Additionally or alternatively, in some examples, the one or more first light emitters, one or more first light sensors, and one or more second light emitters are located along a common optical axis. Additionally or alternatively, in some examples, the device further comprises: one or more second light emitters configured to generate a second light; and one or more second light sensors configured to detect a reflection of the second light and configured to generate a second signal indicative of the reflection of the second light, the second signal including pulsatile blood information, wherein logic is further coupled to the one or more second light sensors and is further configured to receive the second signal and include the second signal in the determination of the physiological signal. Additionally or alternatively, in some examples, the one or more second light emitters and the one or more second light sensors are located in different cavities. Additionally or alternatively, in some examples, the second light includes light with a wavelength between 570-750 nm. Additionally or alternatively, in some examples, the second light includes light with a wavelength between 495-570 nm. Additionally or alternatively, in some examples, the first light and second light intersect. Additionally or alternatively, in some examples, the device further comprises: one or more third light emitters configured to generate a third light, wherein the one or more second light sensors are further configured to detect a reflection of the third light and configured to generate a third signal indicative of the reflection of the third light, the third signal including pulsatile blood information, wherein logic is further configured to receive the third signal and include the third signal in the determination of the physiological signal. Additionally or alternatively, in some examples, the first light includes light with a wavelength between 570-750 nm, the second light includes light with a wavelength between 495-570 nm, and the third light includes light with a wavelength between 750-1400 nm. Additionally or alternatively, in some examples, the one or more first light emitters and the one or more first light sensors are located in a same cavity. Additionally or alternatively, in some examples, the first light includes light with a wavelength between 495-570 nm. Additionally or alternatively, in some examples, at least one of the one or more first light emitters is spaced less than 1 mm from at least one of the one or more first light sensors. Additionally or alternatively, in some examples, the device further comprises: an isolation configured to optically isolate at least one of the one or more first light emitters from at least one of the one or more first light sensors. Additionally or alternatively, in some examples, the device further comprises: a window optically coupled to at least one of the one or more first light emitters, wherein an end of the isolation contacts an inner surface of the window, the inner surface located closer to the one or more first light emitters than an outer surface of the window. Additionally or alternatively, in some examples, the device further comprises: a window optically coupled to at least one of the one or more first light emitters, wherein a first end of the isolation contacts an outer surface of the window, the outer surface located further from the one or more first light emitters than an inner surface of the window. Additionally or alternatively, in some examples, the isolation includes a continuous section disposed between the first end and a second end, the second end located proximate to the at least one of the one or more first light emitters. Additionally or alternatively, in some examples, the isolation comprises: a first section disposed between the first end and a third end, the third end located at the inner surface of the window, and a second section disposed between the third end and a second end, the second end located proximate to the at least one of the one or more first light emitters. Additionally or alternatively, in some examples, the device further comprises: a second isolation, wherein a first end of the isolation is laterally spaced a first distance away from the second isolation and a second end of the isolation is laterally spaced a second distance, different from the first distance, away from the second isolation.

A method for determining a physiological signal is disclosed. The method can comprise: emitting a first light at a user; detecting a reflection of the first light; generating a first signal indicative of the detected reflection of the first light, the first signal including non-pulsatile blood information; emitting a second light at the user; detecting a reflection of the second light; generating a second signal indicative of the detected reflection of the second light, the second signal including pulsatile blood information; adjusting the second signal to compensate for information included in the first signal; and determining the physiological signal based on the adjusted second signal. Additionally or alternatively, in some examples, the first light is emitted at a first portion of the user and the second light is emitted at a second portion, different from the first portion, of the user. Additionally or alternatively, in some examples, the first and second light are emitted at a first portion of the user. Additionally or alternatively, in some examples, the method further comprises: determining one or more peaks included in the first and second signals; and determining one or more locations of the one or more peaks, wherein adjusting the second signal includes scaling the second signal at the one or more locations. Additionally or alternatively, in some examples, the method further comprises: detecting an acceleration of the user; and generating a third signal indicative of the acceleration, wherein adjusting the second signal further includes information included in the third signal. Additionally or alternatively, in some examples, the method further comprises: detecting an acceleration of the user; generating a third signal indicative of the acceleration; comparing the third signal to a threshold value, wherein the second light is emitted at the user when the third signal is greater than or equal to the threshold value.

The light emitter(s) and light sensor(s) may be located such that their illumination field(s) and field-of-view(s), respectively, extend from the back surface of the device housing. In some variations, at least a portion of the back surface of the device housing (e.g., the underside of a wearable device) may contact skin when worn by an individual. The back surface of the device may comprise one or more protrusions or raised regions that may be optionally sized and shaped to facilitate skin contact, and/or apply pressure to the skin in order to facilitate movement of non-pulsatile blood away from skin regions that are within, or in the vicinity of, the illumination field(s) and/or field-of-view(s) of the light emitter(s) and light sensor(s) when the device is worn by the individual (e.g., attached to the wrist, arm, chest, leg, etc.). Since non-pulsatile blood flow may be a significant contributor of motion artifacts in pulsatile blood measurements, reducing the flow of non-pulsatile blood in this region this may help to improve the optical measurements of pulsatile blood.

In some variations, the protrusions may have one or more curves or contours that apply pressure to the skin when the device is worn by the individual. For example, the one or more protrusions may comprise one or more curves or contours that may be convex, and/or concave, and/or convex in some regions and concave in other regions. In some variations, the convex regions of the one or more protrusions may be disposed over the light paths of the light emitter(s) and/or light sensor(s). In other variations, the concave regions of the one or more protrusions may be disposed over the light paths of the light emitter(s) and/or light sensor(s). The one or more protrusions may comprise transparent and/or opaque regions. The regions of the protrusion(s) that are located within the illumination field and/or field-of-view (i.e., optical path or light path) of the light emitter(s) and light sensor(s) may be transparent or translucent, while other regions of the protrusion may be opaque. For example, one or more protrusions may be disposed within the optical path of the light emitter(s) and/or light sensor(s). The back surface (i.e., underside of the device) may comprise an opening or a window in the housing that is aligned with the illumination field and/or field-of-view of the light emitter(s) and/or light sensor(s) and an optically transparent cover structure disposed over or within the opening. For example, the cavity within which the light emitter(s) and/or light sensor(s) reside may comprise an opening or window. The cover structure may be flush with respect to the housing surface, or may be concave or convex. In some variations, a protrusion may comprise a convex cover structure. Some protrusions or cover structures may comprise an optical barrier or isolation as described herein that extends through the thickness of the protrusion. The isolation may obstruct or prevent light from one side of the barrier from interfering with light from the other side of the barrier. In some variations, the isolation may extend continuously from within the cavity and through the thickness of the protrusion. The isolation may be a single component that extends through the cavity and the protrusion, or may be comprised of one or more isolation segments that connected together. The isolation may be approximately parallel to the optical path of the emitters or detectors. The size and shape of an optical opening or window of a cavity may correspond with the size and shape of the illumination field and/or field-of-view of the light emitter(s) and/or light sensor(s). Alternatively or additionally, the diameter of an optical opening or window may vary from about 1 mm to about 20 mm, for example, about 3 mm, about 4 mm, about 5 mm, about 6 mm, about 8 mm, about 10 mm, about 12 mm, about 15 mm, etc., for example, about 5.4 mm, about 6.4 mm.

Figure 16A:
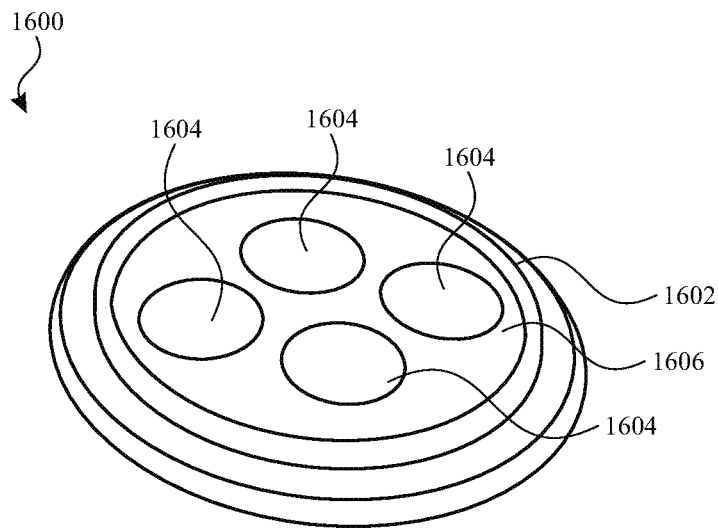
FIG. 16A illustrates a perspective view of an underside or back surface of a wearable device according to examples of the disclosure.
Figure 16B:
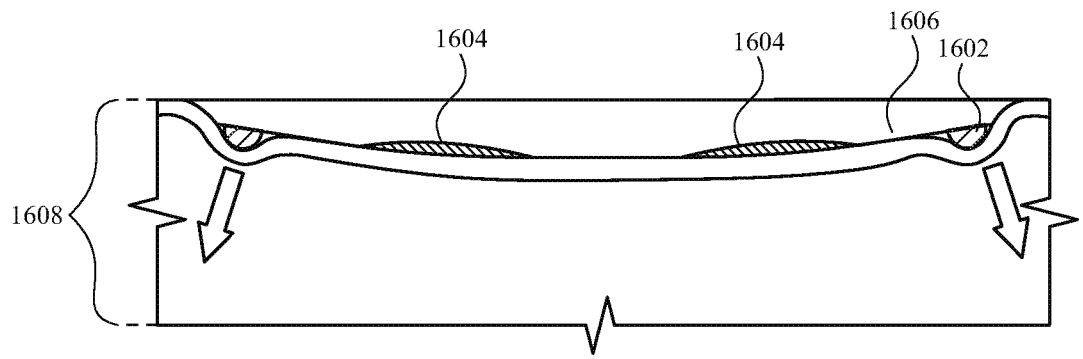
FIG. 16B illustrates a schematic side view of the back surface of FIG. 16A in contact with the skin surface of an individual.

Some variations of a wrist-worn device may have a housing that comprises a protrusion that circumscribes and/or at least partially surrounds and/or encloses the optical opening(s) or window(s) of one or more cavities within which the light emitter(s) and/or light sensor(s) are disposed. The protrusion may not be located in the optical path of the light emitter(s) and/or light sensor(s). One variation of a protrusion that at least partially surrounds the one or more optical openings of one or more cavities of a device is depicted in FIGS. 16A-16B. FIG. 16A depicts a back surface 1600 of a wrist-worn device (such as any of the devices depicted in FIGS. 1A-1C), and a protrusion 1602 that at least partially surrounds the optical openings 1604 of the cavities of the device. One or more optical components (e.g., light emitter(s), light sensor(s), or a combination thereof) may be located within the housing of the device and aligned with an optical opening 1604 of a corresponding cavity. A transparent or translucent cover structure may be disposed over or within each of the optical openings or cavities. The protrusion 1602 may be ring-shaped, which may be an open or closed ring. In still other variations, the protrusion may be arc-shaped. The enclosed region 1606 of the underside or back surface 1600 that is surrounded by the protrusion 1602 may have a convex curvature, as depicted in FIG. 16B, or may have a concave curvature. In still other variations, the enclosed region 1606 may not have any curves, and may be substantially flat. As depicted in FIG. 16A, the protrusion 1602 may surround all of the optical openings 1604 and corresponding cavities, but it should be understood that the protrusion 1602 might surround a subset of the openings and corresponding cavities. For example, some devices may comprise a first protrusion that surrounds a first set of the cavities and a second protrusion that surrounds a second set of the cavities. A device may comprise two or more protrusions that may not surround or enclose any of the cavities, but may span a length or width of the housing of the device. FIG. 16B depicts a side view of the back surface 1600 having a ring-shaped protrusion 1602 when attached to skin 1608 of an individual. In this example, the protrusion 1602 may apply pressure that is focused in a ring around the optical windows 1604. That is, the skin area under the protrusion 1602 may be displaced more (i.e., subject to greater levels of pressure) than the skin area under the region 1606 or optical openings 1604. A protrusion that surrounds the optical openings and/or corresponding cavities may subject skin that surrounds the optical openings and/or corresponding cavities to greater levels of pressure as compared to skin located directly underneath the optical openings and/or corresponding cavities. As described previously, the optical components that are disposed within each of the cavities that correspond to each of the optical openings 1604 may comprise one or more light emitters, one or more light sensors, or a combination of one or more light emitters and one or more light sensors, as described above. The cover structures may each include an isolation that extends from the cavity and through the thickness of the cover structure.

Figure 17A:
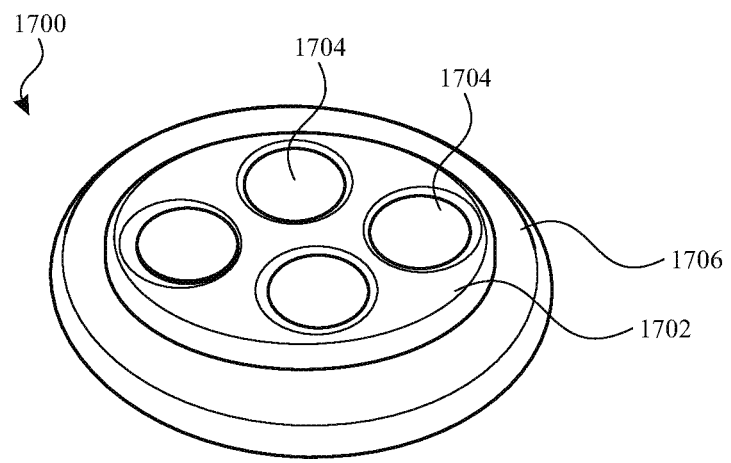
FIG. 17A illustrates a perspective view of another variation of an underside or back surface of a wearable device according to examples of the disclosure.
Figure 17B:
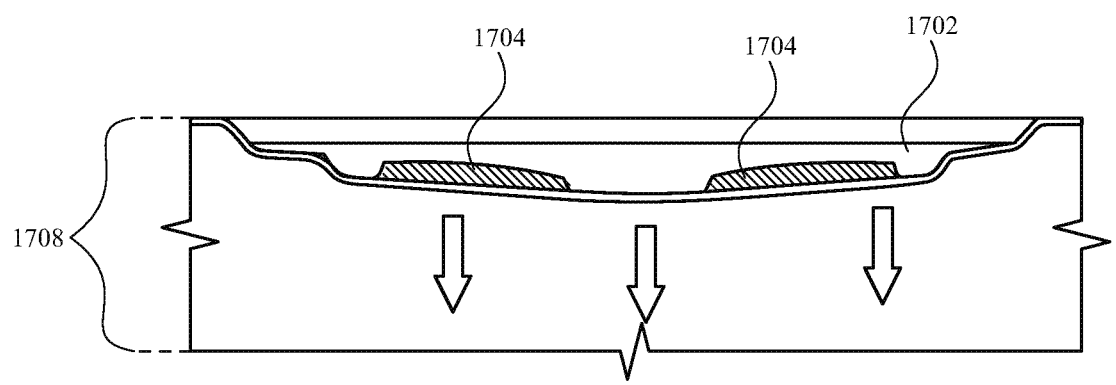
FIG. 17B illustrates a schematic side view of the back surface of FIG. 17A in contact with the skin surface of an individual.

In some variations, the underside or back surface of a device may comprise a protrusion that comprises a raised region that extends from the surface of the housing. The cavities within which the light emitter(s) and/or light sensor (s) and their corresponding optical openings may be located on the protrusion. For example, the protrusion may form a plateau that extends from the surface of the housing, and the optical openings and/or corresponding cavities may be located on the surface of the plateau. The plateau may extend over or across a substantial portion of the area of the back surface (e.g., the surface area of the plateau may be about 30%, or about 40%, or about 50% or about 60% or more, of the surface area of the entire back surface). For example, the surface area of the plateau may be approximately the same as the surface area of the underside or back surface (e.g., covers the entire back surface), or the surface area of the plateau may be about 20% less, about 30% less, about 40%, about 50% less than the surface area of the back surface. One variation of a device having a back surface that comprises a protrusion or raised region that extends from and across the back surface is depicted in FIGS. 17A-17B. Underside or back surface 1700 may comprise a protrusion 1702 comprising a surface that is raised relative to the other regions 1706 of the back surface 1700. The device may comprise four optical openings 1704 corresponding to four cavities that are located on the raised surface of the protrusion 1702. The surface of the protrusion 1702 that contacts the skin may be flat (i.e., without any curves), or may have a convex curve, as depicted in FIGS. 17A and 17B. The cover structures disposed over or within the optical openings 1704 may be flush with the surface of the protrusion 1702, or may protrude even further from the surface of the protrusion 1702. FIG. 17B depicts a side view of the back surface 1700 when attached to skin 1708 of an individual. The skin regions in contact with the protrusion 1702 may be subject to greater levels of pressure as compared to the skin in contact with the non-raised regions 1706 of the back surface 1700, as schematically represented by the arrows in FIG. 17B. That is, the skin region directly underneath and in the vicinity of the optical openings may be subject to increased pressure levels. While the protrusion 1702 is depicted as having a circular shape, it should be understood that the protrusion might have any shape (e.g., ellipse, oval, rectangle, etc.). In other variations, a back surface may comprise two or more raised regions or protrusions that are co-located with the optical openings. For example, a back surface may comprise a first semi-circular protrusion that extends over the portions of the back surface that include a first subset of the cavities and/or corresponding optical openings and a second semi-circular protrusion that extends over the portions of the back surface that includes a second subset of the cavities and/or corresponding optical openings. As described previously, the optical components that are disposed within each of the cavities that correspond to each of the optical openings 1704 may comprise one or more light emitters, one or more light sensors, or a combination of one or more light emitters and one or more light sensors, as described above. The cover structures may each include an isolation that extends from the cavity and through the thickness of the cover structure.

Figure 18A:
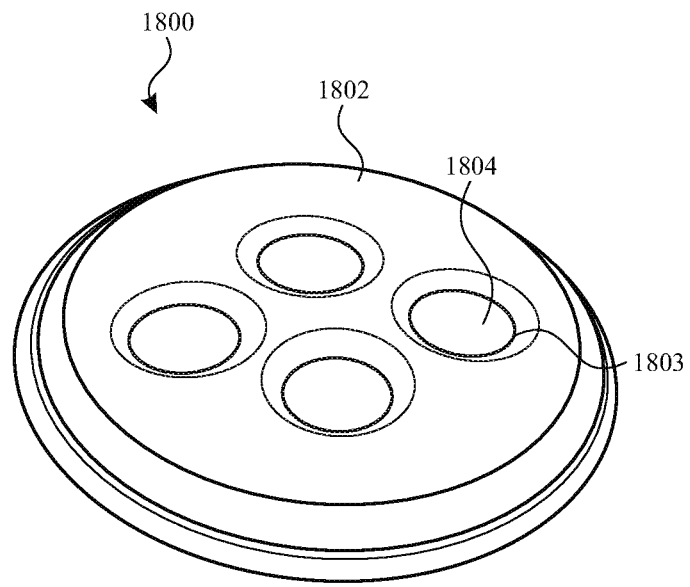
FIGS. 18A and 18B illustrate perspective views of other variations of an underside or back surface of a wearable device according to examples of the disclosure.
Figure 18B:
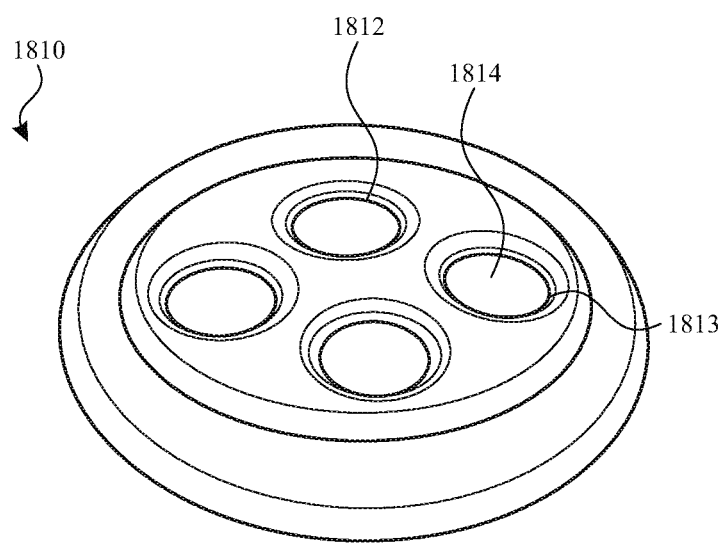
Figure 18C:
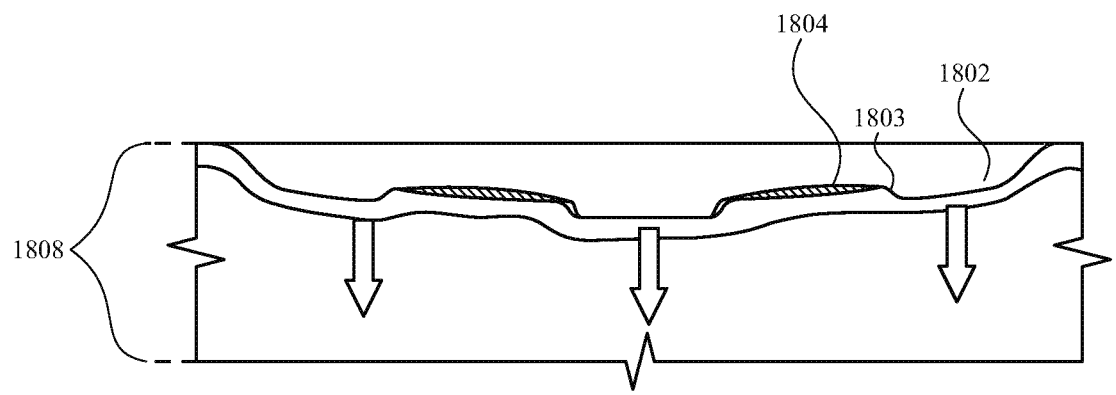
FIG. 18C illustrates a schematic side view of the back surface of FIG. 18A in contact with the skin surface of an individual.

In some variations, a back surface of a wearable device may be similar to the protrusion(s) described above and depicted in FIGS. 17A and 17B, however, the protrusion(s) may comprise one or more recessed regions within which the optical opening or windows of the cavities may be located. The surface of the cover structure disposed over each optical window may be set within each recess such that the cover structure surface is not flush with, nor does it extend beyond, the surface of the protrusion. One variation is depicted in FIG. 18A. As depicted there, back surface 1800 of a wearable device may comprise a protrusion 1802 that comprises recesses (i.e., recessed regions) 1803 that are each located over an optical opening or window 1804. That is, the cavities within which the light emitter(s) and/or light sensor(s) are located may themselves be located within a recess of a protrusion. The height of the cover structures located over each of the optical openings may not exceed the depth of each of the recesses 1803. FIG. 18C depicts a side view of the back surface 1800 when contacting skin 1808 of an individual. The skin regions in contact with the regions 1805 of the protrusion 1802 between the recessed regions 1803 or optical windows 1804, or outside of the recessed regions (e.g., around or near the outer edge or perimeter of the protrusion 1802) may be subject to higher levels of pressure as compared to the skin regions in contact with the recessed regions 1803 and/or cover structures of the optical openings 1804. For example, skin regions that may be subject to increased pressure levels are represented by the arrows in FIG. 18C. The surface area of the protrusion 1802 may be similar to the surface area of the back surface 1800, as depicted in FIG. 18A, or may be less than the surface area of the back surface 1810, as depicted in FIG. 18B. As depicted there, the protrusion 1812 may comprise recesses 1813 disposed over the optical openings or windows 1814, as described previously. The surface area of the protrusion 1812 may be about 20% less, about 30% less, about 40%, about 50% less than the surface area of the back surface 1810. The skin regions that contact the regions 1816 of the back surface that surround the protrusion 1812, or that contact the recessed regions 1813 of the protrusion 1812 may be subject to reduced levels of pressure as compared to the skin regions in contact with the protrusion 1812. As described previously, the optical components that are disposed within the cavities that correspond to each of the optical openings 1804, 1814 may comprise one or more light emitters, one or more light sensors, or a combination of one or more light emitters and one or more light sensors. The cover structures may each include an isolation that extends from the cavity and through the thickness of the cover structure.

Figure 19A:
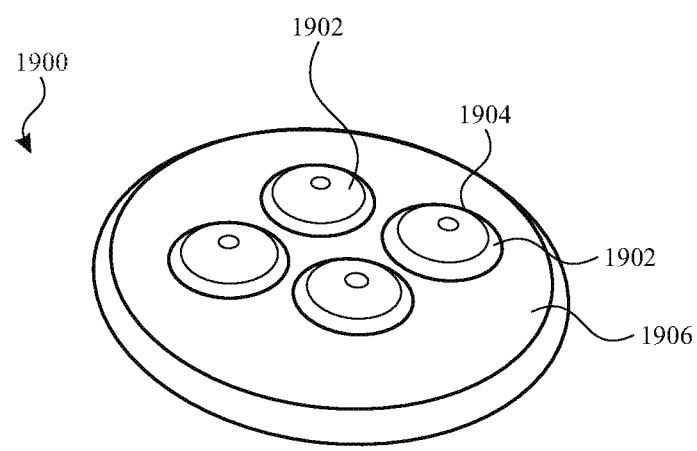
FIG. 19A illustrates a perspective view of another variation of an underside or back surface of a wearable device according to examples of the disclosure.
Figure 19B:
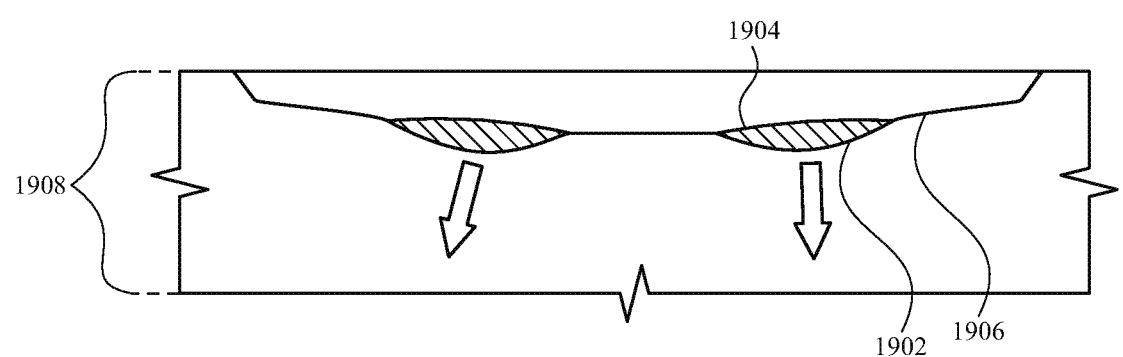
FIG. 19B illustrates a schematic side view of the back surface of FIG. 19A in contact with the skin surface of an individual.

In some variations, the underside or back surface of a wearable device may comprise protrusions disposed in the optical path of the light emitter(s) and/or light sensor(s). In such variations, the protrusions may be optically transparent or translucent. For example, the back surface of a wearable device may comprise one or more cavities each having a corresponding optical opening and a protrusion located over each of the optical openings. In some variations, the cover structure disposed over each of the optical openings may be itself a protrusion that applies focal regions of higher pressure directly on the skin regions located under the optical path of the light emitter(s) and/or detector(s). In other words, the skin region(s) that may be subject to increased levels of pressure may co-localize with the illumination field(s) of the one or more light emitters and/or the field-of-view(s) of the one or more light sensors (in contrast to, for example, a protrusion that applies focal regions of increased pressure to skin that is located between the illumination field(s) and/or field-of-view(s) of the emitters and/or detectors, such as is depicted in FIG. 18C). One variation of a device having an underside or back surface comprising protrusions disposed within the optical path(s) of the light emitter(s) and/or light sensor(s) is depicted in FIGS. 19A-19B. Back surface 1900 may comprise one or more optical openings or windows 1904 and a convex cover structure or protrusion 1902 disposed over each of the optical openings 1904 of the corresponding cavities. The protrusion 1902 may comprise an optically transparent or translucent material such as acrylic, glass, and the like. FIG. 19B depicts a side view of the back surface 1900 when the device is worn by an individual and the back surface is located against skin 1908 of the individual. As depicted there, the skin regions located under the protrusion 1902 (which are schematically represented by the arrows in FIG. 19B) may be subject to increased levels of pressure as compared to the skin regions located under non-protruding portions 1906 of the back surface 1900. The radius of curvature of the protrusions 1902 may be consistent across the surface of the protrusion (i.e., the curvature of the protrusion approximates the curvature of a sphere), or may vary (i.e., the curvature of the protrusion may be similar to the curvature of an ovoid). As described previously, the optical components that are disposed within each of the cavities that correspond to each of the optical openings 1904 may comprise one or more light emitters, one or more light sensors, or a combination of one or more light emitters and one or more light sensors, as described above. The cover structures may each include an isolation that extends from the cavity and through the thickness of the cover structure.

Figure 20:
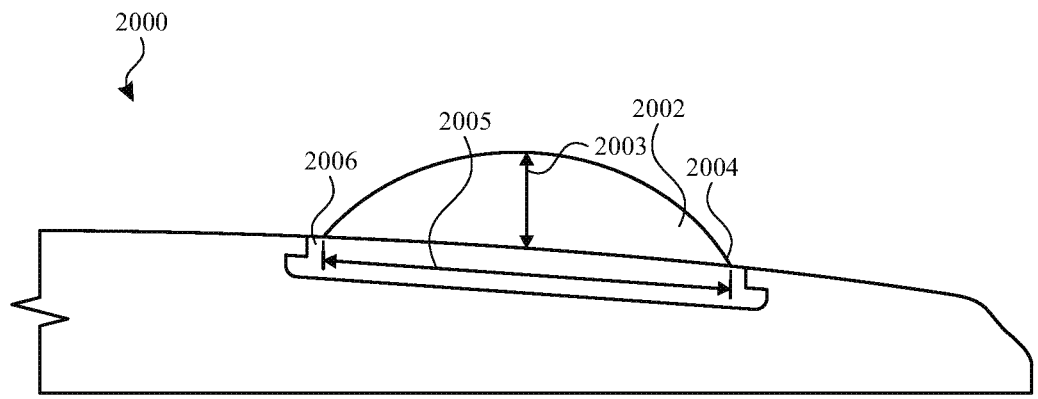
FIG. 20 illustrates a cross-sectional view of one variation of a protrusion.

The height and/or curvature of the one or more protrusions of a back surface of a wearable device may vary, as may be desirable to attain a desired contact and/or pressure profile in the skin of the individual. FIG. 20 depicts examples of various protrusion surface geometries of protrusions similar to the protrusions depicted in FIGS. 19A and 19B (though such sizes and geometries may be applicable to any of the protrusions and/or optical window cover structures described previously). FIG. 20 depicts an underside or back surface 2000 of a wearable device comprising a protrusion 2002 that is located over an optical opening or window 2004 of a cavity 2006. In some variations, the protrusion may comprise the cover structure disposed over the optical opening. The protrusion 2002 may have a height 2003 from about 0.3 mm to about 2 mm, for example, about 0.5 mm, or about 0.9 mm, about 1.1 mm, about 1.3 mm, etc. The radius of curvature of the protrusion 2002 may be from about 2.5 mm to about 8.5 mm, for example, about 3.23 mm, about 3.43 mm, about 4.25 mm, about 4.47 mm, about 6.5 mm, about 7.47 mm, etc. The width 2005 of base of the protrusion 2002 may span the width of the optical opening 2004, or may be less than the width of the optical opening. In some variations, the width 2005 may be from about 3 mm to about 10 mm, for example, about 3.5 mm, about 4.6 mm, about 5.4 mm, about 6 mm, about 7.3 mm, about 8.8 mm, etc.

Figure 21A:
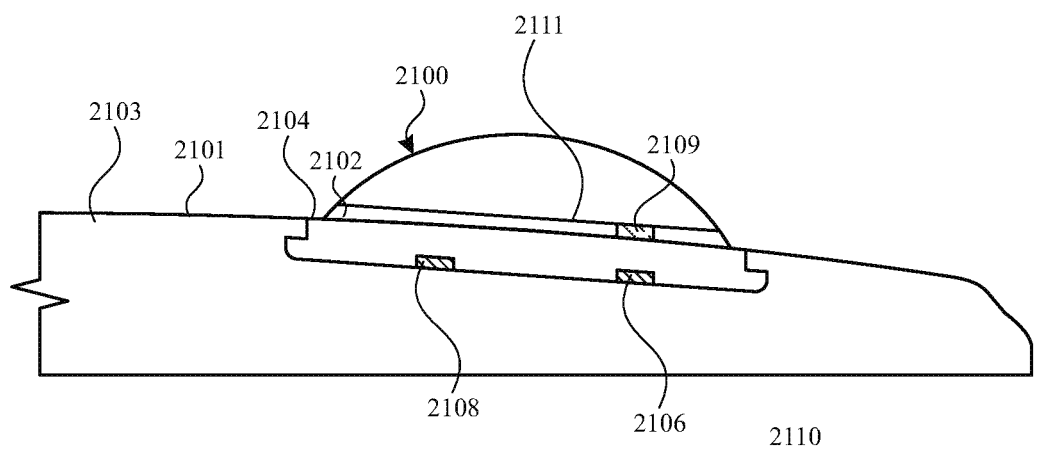
FIG. 21A illustrates a cross-sectional view of one variation of a device comprising a protrusion and a Fresnel lens.

In some variations, the cover structure and/or protrusion may comprise a Fresnel lens or similar optical component. Since the wearable device may include several optical components and associated wiring, it can be desirable to obscure the components and prevent internal components from being visible to a user's eye. In addition to obscuring the internal components, it may be desirable that the light emitted from a light emitter retains its optical power, collection efficiency, beam shape, and collection area so that the intensity of light is unaffected. To obscure internal components, one or more lenses such as Fresnel lenses may be located in the protrusion, and/or between the protrusion and cover structure, and/or in the cover structure, and/or within the thickness of the housing material, and/or underneath the housing (e.g., within the volume enclosed by the housing). For example, a Fresnel lens 2102 may be located between the protrusion 2100 and a light emitter 2106 that is located within a cavity 2110, as shown in FIG. 21A. In this variation, the Fresnel lens 2102 may be located above the optical opening 2104 of the cavity 2110, that is, extending from the surface 2101 of the device housing 2103. Fresnel lens 707 can have two regions: an optical center 2109 and a cosmetic zone 2111. Optical center 2109 can be placed in substantially a same area or location as light emitter 2106 to collimate the emitted light into a smaller beam size. Cosmetic zone 2111 can be located in areas outside of optical center 2109. The cosmetic zone 2111 may comprise ridges that may help to obscure the underlying internal components. Optionally, a light sensor 2108 disposed within the same cavity 2110 as the light emitter 2106 may be covered by the same or different Fresnel lens, which may or may not have an optical center (i.e., a large-area light sensor may be a large-area photodiode that may not require shaping of the light field may not require a Fresnel lens with an optical center and instead may use a Fresnel lens having one or more regions comprising ridges configured for a cosmetic zone). The ridge shapes of the Fresnel lens 2102 may vary to help facilitate obscuration, especially in cosmetic zones. For example, deep and sharp saw tooth patterns can be used for high obscuration needs. Other types of ridge shapes can include rounded cylindrical ridges, asymmetric shapes, and wavy shapes (i.e., ridges that move in and out). The Fresnel lens 2102 may be used additionally or alternatively for light collimation. By collimating light, the optical signal efficiency can be improved. Without a lens or similar collimating optical element, emitter light may be directed at an angle away from the light sensor and can be lost. Additionally or alternatively, light may be directed at an angle toward the light sensor, but the angle may be shallow. The Fresnel lens 2102 may redirect light to directions that otherwise may be lost or enter into the tissue at shallow angles. Such redirected light can be collected instead of being lost and/or may militate against parasitic non-signal light, resulting in improved optical signal efficiency. In some examples, a diffusing agent may be used alternatively or additionally to a Fresnel lens. A diffusing agent may be surrounding, touching, and/or covering one or more components of a light emitter. In some examples, diffusing agent may be a resin or epoxy that encapsulates the dies or components and/or wire bonds. Diffusing agent may be used to adjust the angle of the light emitted from the light emitter. By narrowing the beam of light emitted, more light may be collected by the lens and/or window resulting in a larger amount of detected light by the light sensor.

Figure 21B:
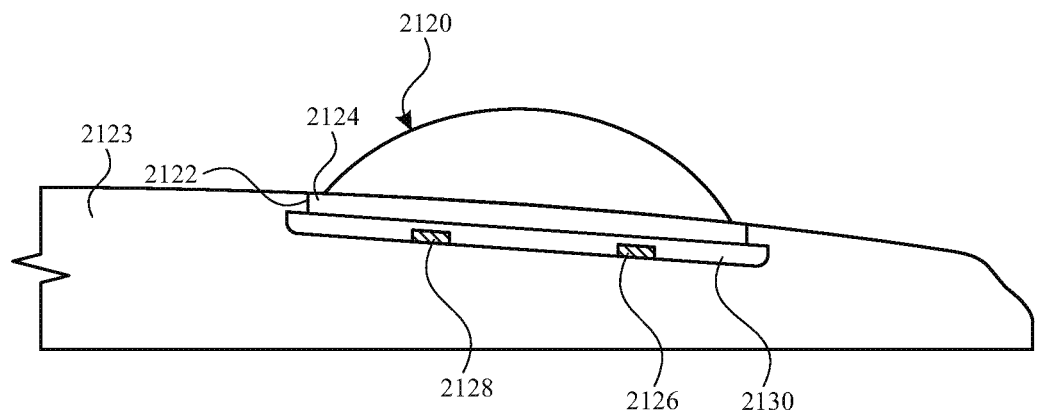
FIG. 21B illustrates a cross-sectional view of another variation of a device comprising a protrusion and a Fresnel lens.

In another variation depicted in FIG. 21B, a Fresnel lens 2122 may be located between the protrusion 2120 and a light emitter 2126 that is located within a cavity 2130. In this variation, the Fresnel lens 2122 may be located within the optical opening 2124 of the cavity 2130, that is, within the thickness of the device housing 2123. There may optionally be a light sensor 2128 within the cavity 2130. The Fresnel lens 2122 may have any of the characteristics described above, and may or may not have an optical center located over either the light emitter 2126 and/or light sensor 2128 (the variation in FIG. 21B uses a Fresnel lens that does not have an optical center).

Figure 22A:
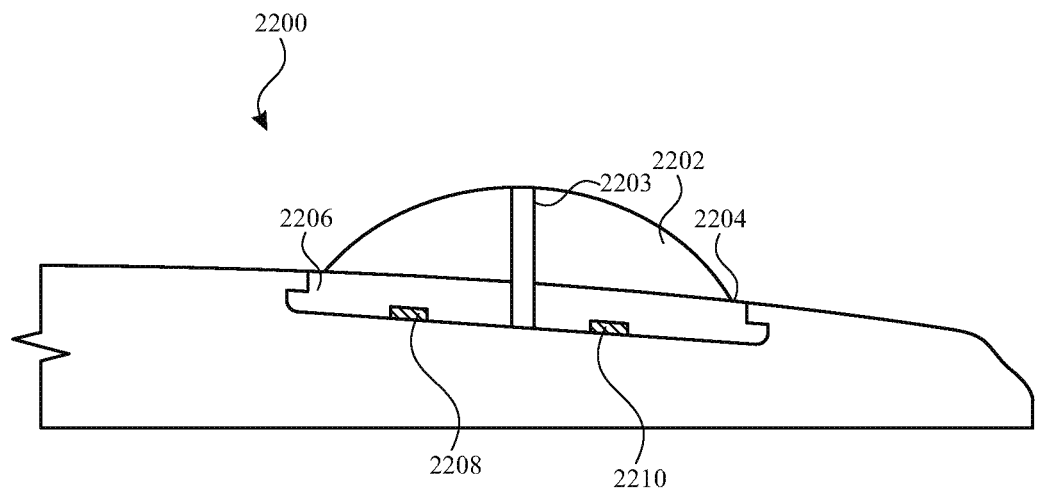
FIG. 22A illustrates a cross-sectional view of one variation of a protrusion comprising an isolation or optical barrier.
Figure 22B:
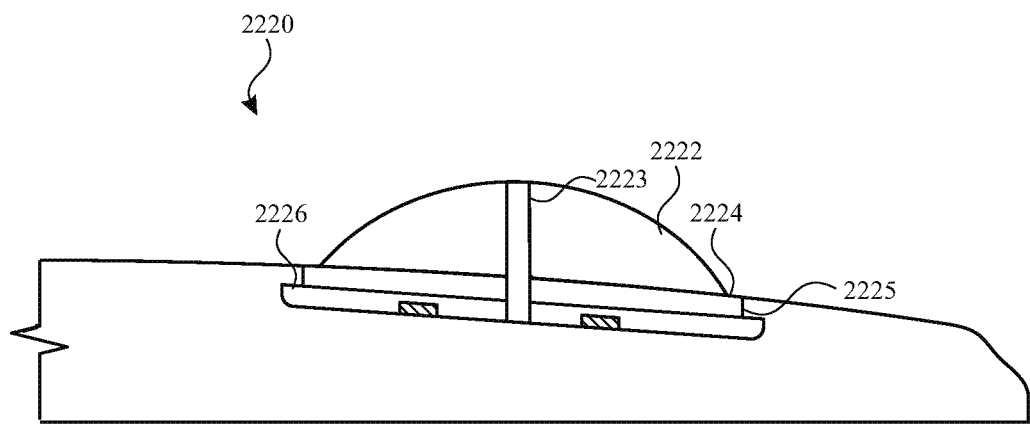
FIG. 22B illustrates a cross-sectional view of one variation of a device comprising an isolation or an optical barrier, and a Fresnel lens disposed between the protrusion and the light emitter and light sensor.

As indicated above, some variations of protrusions may comprise an isolation that extends through the entire thickness of the protrusion, where the isolation is configured to separate the light paths of the optical components on one side of the protrusion from the other side. The isolation may extend from within the cavity, through the cavity and through the thickness of the protrusion. FIG. 22A depicts one variation of an underside or back surface 2200 of a wearable device comprising a protrusion 2202 disposed over an optical opening 2204 of a cavity 2206, where the protrusion 2202 comprises an isolation or optical barrier 2203 extending through the thickness of the protrusion. In this example, the isolation 2203 extends from inside the cavity 2206 to and through the protrusion 2202. While the isolation 2203 is depicted as being substantially perpendicular to the base of the cavity, it should be understood that the isolation 2203 may be at an angle with respect to the base of the cavity. A first optical component 2208 (e.g., a light emitter or light sensor) may be located on one side of the cavity and a second optical component 2210 (e.g., a light sensor or a light emitter) may be located on the other side of the cavity such that the isolation 2203 separates the light paths of these first and second optical components within the protrusion and the cavity. Isolation 2203 may be similar to any of the isolation variations described previously. FIG. 22B depicts another variation of an underside or back surface 2220 of a wearable device comprising a protrusion 2222 disposed over an optical opening 2224 of a cavity 2226, where the protrusion 2222 comprises an isolation or optical barrier 2223 extending through the thickness of the protrusion. In this variation, a Fresnel lens assembly 2225 may be located within the optical opening and/or cavity 2226 (e.g., as part of the thickness of the housing and/or located within the volume enclosed by the housing). Alternatively or additionally, a Fresnel lens assembly may be located within the protrusion 2222, as previously described. The Fresnel lens assembly 2225 may comprise a first Fresnel lens and a second Fresnel lens that are each coupled to one side of the isolation 2223. The first and second Fresnel lenses may be manufactured as two separate and/or independent Fresnel lenses that are attached to the isolation 2223. Alternatively, the first and second Fresnel lenses may be manufactured as a single Fresnel lens and then cut into two components and attached to the isolation 2223. The one or more Fresnel lenses of a Fresnel lens assembly may have any of the lens characteristics described previously.

Figure 22C:
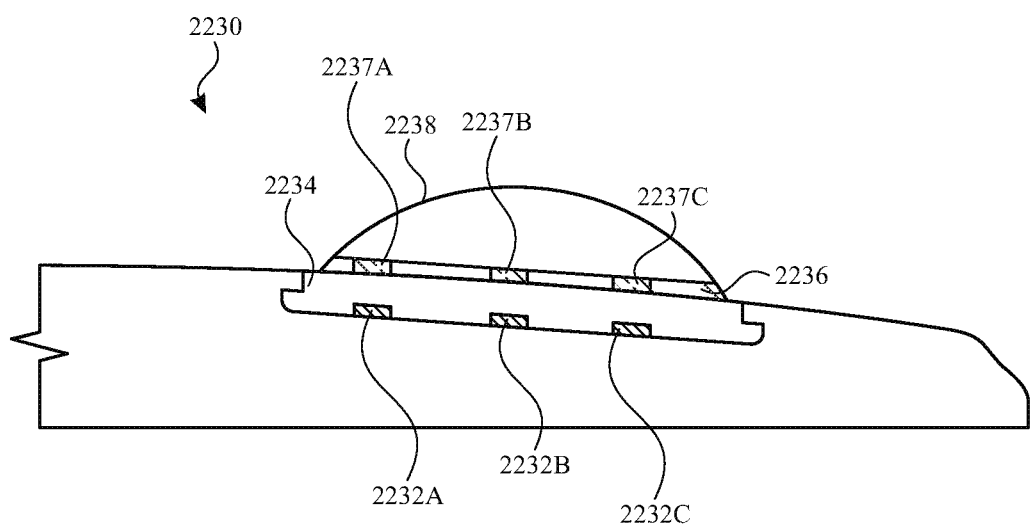
FIG. 22C illustrates a cross-sectional view taken across line 22C-22C of one variation of a wearable device (e.g., the device depicted in FIG. 22D) comprising an isolation or an optical barrier and a Fresnel lens disposed between the protrusion and a plurality of light emitters and light sensor.
Figure 22D:
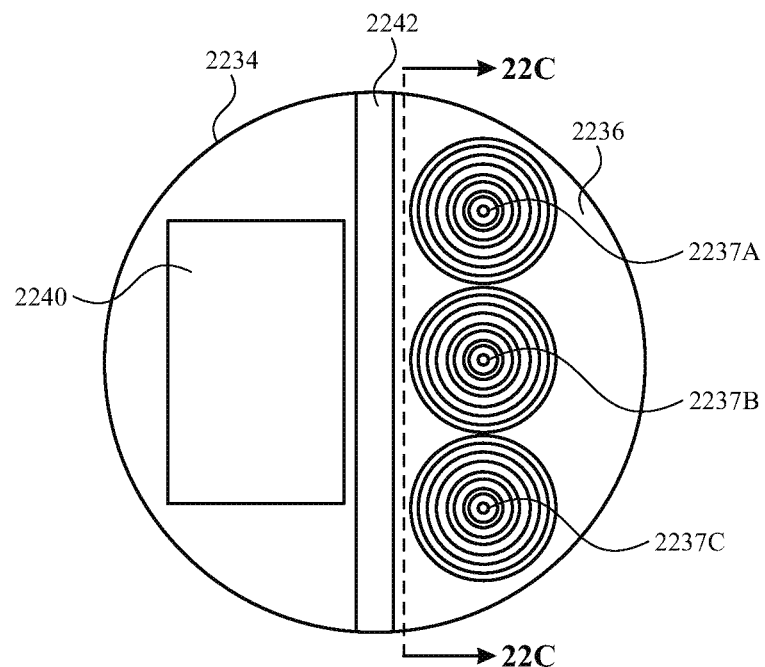
FIG. 22D illustrates a top view of the underside of a wearable device comprising one variation of a Fresnel lens.
Figure 22E:
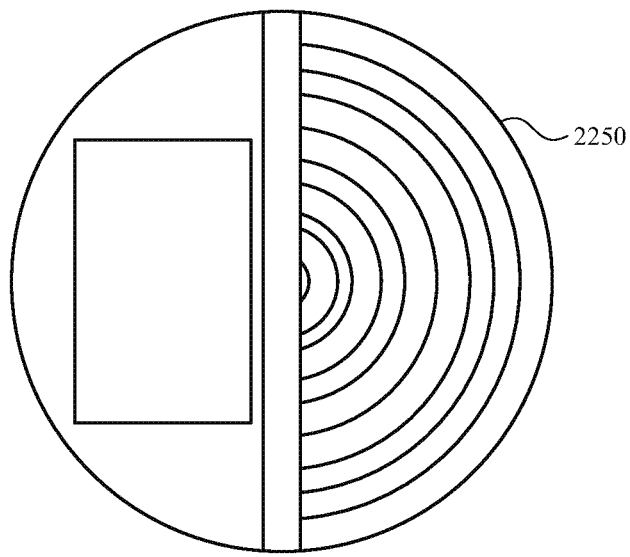
FIG. 22E illustrates a top view of the underside of a device comprising another variation of a Fresnel lens.

In some variations of a wearable device, there may be two or more light emitters in the same cavity and one or more Fresnel lens disposed between the protrusion and the light emitters. The Fresnel lens may comprise one optical center for each light emitter within the cavity. FIG. 22C depicts a wearable device 2230 comprising three light emitters 2232a, b,c located within a cavity 2234, and a Fresnel lens 2236 disposed between the light emitters 2232a,b,c and a cover structure and/or protrusion 2238 located over the opening of the cavity 2234. In this example, there may be a light sensor 2240 disposed in the same cavity of the light emitters and an isolation 2242 that provides an optical barrier between the light sensor and the light emitters. The light emitters 2232a, b,c may be collinearly arranged, or may be offset with respect to each other in any pattern. In some variations, light emitters of a particular wavelength may be located closer to the light sensor than the other light emitters. For example, red and/or infrared light emitters may be in closer proximity to the light sensor than a green light emitter. FIG. 22D is a top view of the cavity 2234 of the device of FIG. 22D. The Fresnel lens 2236 may comprise three optical centers 2237a, b,c that are each located over (e.g., aligned with) a corresponding light emitter 2232a,b,c. The ridge pattern as viewed from above the underside of the device may appear to have three sets of concentric rings, or spirals, or a plurality of concentric and/or merged arcs. In some variations, where the light emitters are not arranged collinearly, the optical centers of the Fresnel lens may be offset with respect to each other. Alternatively, the Fresnel lens may not have any optical centers located over any of the light emitters (and/or light sensors). FIG. 22E depicts an example of a cavity of a wearable device similar to that of FIG. 22D, but where the Fresnel lens does not have an optical center that is located over (e.g., aligned with) a light emitter. The ridge pattern of the Fresnel lens 2250 as viewed from above the underside of the device may appear to have arc-shaped edges. In some variations, a Fresnel lens without any optical centers may have the appearance of a plurality of concentric semicircles, partially truncated circles (e.g., having one, two, three, four or more truncated sides), concentric arcs and the like. The ridge pattern shape, size, edge density, etc. may vary from those depicted in FIGS. 22C and 22D, as may be desirable.

Any number, size, shape/geometry, etc. of the protrusions described above may be applied to any of the devices described herein, as may be desirable.

As discussed above, noise correction can be performed by using a noise reference channel (e.g., including a red or infrared light emitter) to correct or adjust the signal measured by a PPG channel (e.g., including a green light emitter). In some instances, the optical attenuation coefficient associated with the noise reference channel can be smaller than the optical attenuation coefficient associated with the PPG channel. As a result, the light from the noise reference may traverse deeper into the user's tissue compared to the light from the PPG channel, even if the separation distance between the light emitters and light sources are the same. With light traversing deeper, the sensing volume in the user's tissue of the noise reference channel may differ from the sensing volume of the PPG channel, thereby possibly reducing the effectiveness of the noise correction. One way to enhance the effectiveness of the noise correction can be to configure the light emitter and light sensor for the noise reference channel to have a shorter separation distance than the light emitter and light sensor for the PPG channel. In some instances, the differing separation distances can result in the optical components occupying a larger area on the back of the device, which can lead to larger windows.

Figure 23A:
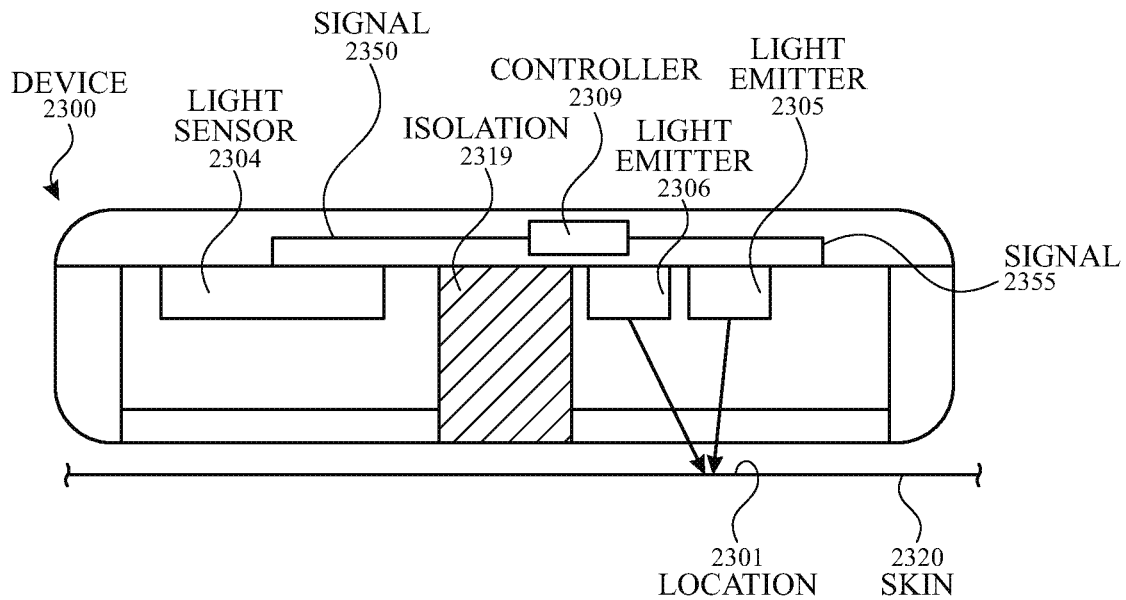
FIGS. 23A-23C illustrate cross-sectional views of exemplary configurations of light emitters for co-localizing the noise reference and PPG channels according to examples of the disclosure.
Figure 23B:
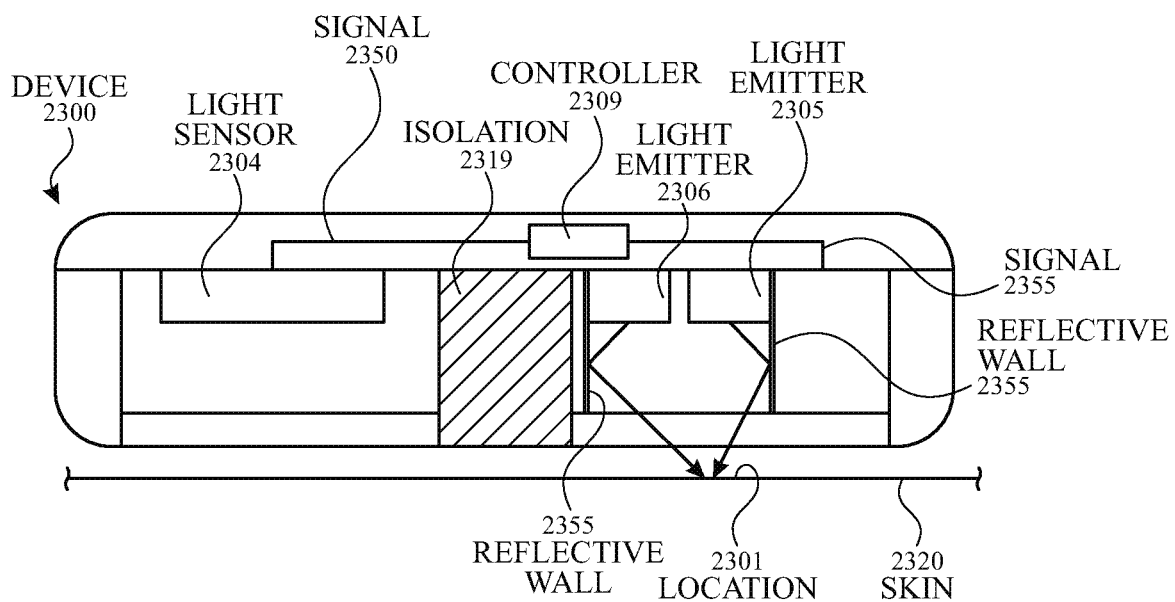
Figure 23C:
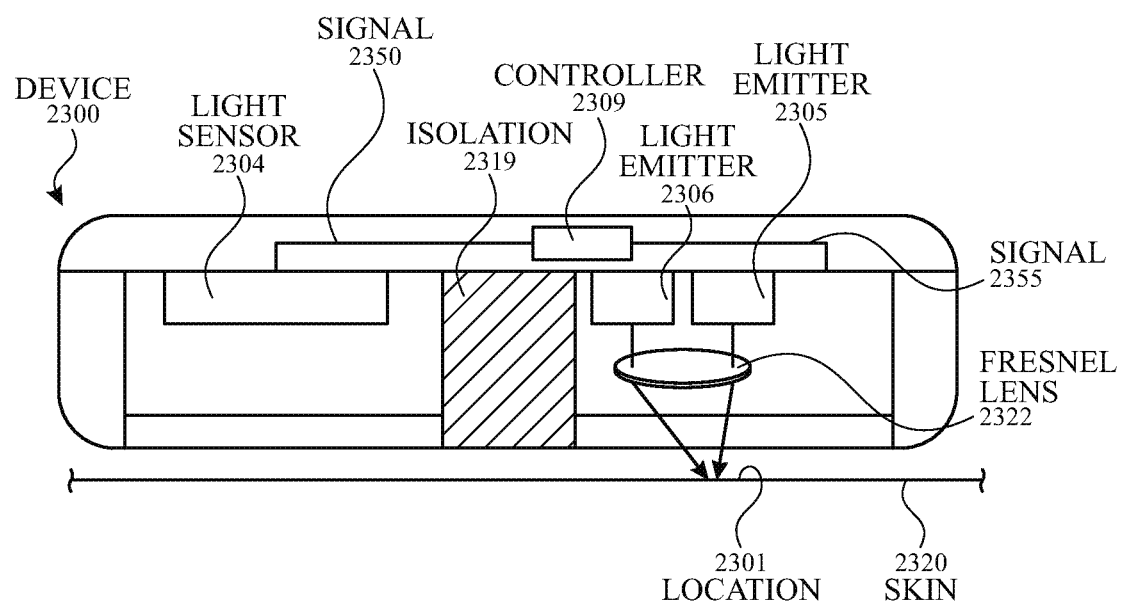

Another way to enhance the effectiveness of the noise correction can be to co-localize the noise reference and PPG channels. FIGS. 23A-23C illustrate cross-sectional views of exemplary configurations of light emitters for co-localizing the noise reference and PPG channels according to examples of the disclosure. In some examples, the light emitters can be configured with different light emission angles, as illustrated in FIG. 23A. Device 2300 can include light emitter 2305, light emitter 2306, and light sensor 2304. Light emitter 2305 and light emitter 2306 can be co-localized such that the separation distance between light emitter 2305 and light sensor 2304 relative to the separation distance between light emitter 2306 and light sensor 2304 can be substantially the same (e.g., within 10% difference). For example, light emitter 2305 can be located in close proximity (e.g., less than or equal to 1 mm away) to light emitter 2306. In some examples, light sensor 2304 can be located in a cavity different from light emitter 2305 and light emitter 2306, separated by isolation 2319. In some examples, one or more light emitter-light sensor sets located in different cavities can be configured to measure pulsatile blood volume changes. In some examples, one or more light emitter-light sensor sets located in the same cavity can be configured to measure non-pulsatile blood volume changes (from shallow tissues structures, deep tissue structures, or both) and/or serve as a noise reference channel. For example, the set comprising light emitter 2306 and light sensor 2304 can be configured to be sensitive to pulsatile blood volume changes. The set comprising light emitter 2305 and light sensor 2304 can be less sensitive to arterial blood volume changes (than the set comprising light emitter 2306 and light sensor 2305) and can be configured to generate a signal indicative of the non-pulsatile blood changes (e.g., noise).

Light emitter 2305 can be configured to emit light towards skin 2320 and in the direction of light sensor 2304, while light emitter 2306 can be configured to emit light towards 2320 and away from the direction of light sensor 2304. In this manner, light emitted by light emitter 2306 can probe deeper into skin 2320, and light emitter by light emitter 2305 can probe shallower into skin 2320. The depth of penetration can be achieved by configuring the angles of light emission from light emitter 2305 and light emitter 2306 to be different, for example. The angles of light emission can be configured such that light from both light emitter 2305 and light emitter 2306 are incident on the same location 2301 and penetrate the same volume of tissue in skin 2320. As a result, device 2300 can include multiple channels configured to measure a similar optical sensing volume even if the attention coefficients of the multiple channels differ and with reduced area constraints. In some variations, the light emitter (e.g., light emitter 2306) included in the PPG channel can be located closer to light sensor 2304 than the light emitter (e.g., light emitter 2305) included in the noise reference channel. Controller 2309 can receive signal 2350 and signal 2355 and can apply one or more algorithms to determine the user's physiological signal. Although the figure illustrates a single light ray emitted by the light emitters, examples of the disclosure can include multiple light rays emitted by the light emitters; a single light ray is illustrated for clarity purposes.

In some examples, the device can include one or more reflective walls for changing the depth of penetration of the different light emitters, as illustrated in FIG. 23B. The device can include reflective walls 2315. At least a portion of light emitted by light emitter 2306 can be directed towards light sensor 2304 and can reflect off a reflective wall 2315. A portion of light emitted by light emitter 2305 can be directed away from light sensor 2304 and can reflect off a reflective wall 2315. Both light rays can be incident on the same location 2301 and/or same volume of tissue in skin 2320.

In some examples, the device can include one or more Fresnel lenses for changing the angles of light emitted by the light emitters, as illustrated in FIG. 23C. The device can include Fresnel lens 2322. In some examples, light emitted by light emitter 2305 and light emitter 2306 can include the same angle of incidence on the surface of Fresnel lens 2322. The Fresnel lens can be configured to change the angle of incidences of the light beams. For example, Fresnel lens 2322 can redirect light emitted by emitter 2306 towards one direction and can redirect light emitted by light emitter 2306 towards another direction. In some examples, the angles of light exiting Fresnel lens 2322 can be between 30-60°. The angles for light originating from light emitter 2306 can be the same or different from light originating from light emitter 2305. Both light rays can be incident on the same location 2301 and/or same volume of tissue in skin 2320.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:

1. A method for determining a physiological signal, the method comprising:
    emitting a first light at a user;
    detecting a first reflection of the first light;
    generating a first signal indicative of the detected first reflection of the first light, the first signal including non-pulsatile blood information;
    detecting an acceleration of the user;
    generating a second signal indicative of the acceleration;
    comparing the second signal to a threshold value;
    in response to the second signal being greater than or equal to the threshold value, emitting a second light at the user;
    detecting a second reflection of the second light;
    generating a third signal indicative of the detected second reflection of the second light, the third signal including pulsatile blood information;
    adjusting the third signal to compensate for information included in the first signal; and
    determining the physiological signal based on the adjusted third signal.

2. The method of claim 1, wherein the first light is emitted at a first portion of the user and the second light is emitted at a second portion, different from the first portion, of the user.

3. The method of claim 1, further comprising:
    determining one or more peaks included in the first and third signals; and determining one or more locations of the one or more peaks, wherein adjusting the third signal includes scaling the third signal at the one or more locations.

4. The method of claim 1, wherein adjusting the third signal further includes using information included in the second signal.

5. An electronic device comprising:
a housing at least partially defining a first cavity and a second cavity separate from the first cavity;
a first light emitter positioned in the first cavity and configured to generate a first light;
a first light sensor positioned in the first cavity and configured to:
 detect a first reflection of the first light; and
 generate a first signal indicative of the first reflection of the first light, the first signal including non-pulsatile blood information;
a second light emitter positioned in the first cavity and configured to generate a second light;
a second light sensor positioned in the second cavity and configured to:
 detect a second reflection of the second light; and
 generate a second signal indicative of the second reflection of the second light, the second signal including pulsatile blood information; and
a controller coupled to the first light sensor and the second light sensor, the controller configured to:
 receive the first signal and the second signal; and
 determine at least a portion of a physiological signal using the first signal and the second signal.

6. The electronic device of claim 5, further comprising an isolation member positioned at least partially within the housing and configured to separate the first cavity and the second cavity.

7. The electronic device of claim 5, further comprising an isolation member positioned between the first light emitter and the first light sensor and configured to optically isolate the first light emitter and the first light sensor.

8. The electronic device of claim 7, wherein:
the electronic device further comprises a window optically coupled to the first light emitter; and
an end of the isolation member extends to an inner surface of the window.

9. The electronic device of claim 7, wherein:
the electronic device further comprises a window optically coupled to the first light emitter; and
an end of the isolation member extends to an outer surface of the window.

10. The electronic device of claim 5, wherein the first light emitter is spaced less than 1 mm from the first light sensor.

11. The electronic device of claim 5, wherein:
the electronic device further comprises one or more third light emitters configured to generate a third light;
at least one of the first light sensor or the second light sensor is, further configured to:
 detect a third reflection of the third light; and
 generate a third signal indicative of the third reflection of the third light; and
the controller is further configured to receive the third signal and include the third signal in the determination of the physiological signal.

12. The electronic device of claim 11, wherein the first light includes light with a wavelength between 570-750 nm, the second light includes light with a wavelength between 495-570 nm, and the third light includes light with a wavelength between 750-1400 nm.

* * * * *